(12) United States Patent
Ho et al.

(10) Patent No.: US 8,314,091 B2
(45) Date of Patent: Nov. 20, 2012

(54) N-BENZYL,N'-ARYLCARBONYLPIPERAZINE DERIVATIVES

(75) Inventors: Koc-Kan Ho, West Windsor, NJ (US); Andrew Laird Roughton, Plainsboro, NJ (US); Irina Neagu, Plainsboro, NJ (US); Jui-Hsiang Chan, West Windsor, NJ (US); Nasrin Ansari, Monmouth Junction, NJ (US); Michelle Lee Morris, Lawrenceville, NJ (US); Yajing Rong, Dayton, NJ (US); Michael Ohlmeyer, Plainsboro, NJ (US); Andrew John Cooke, Newhouse (GB); Andrew Stanley Edwards, Newhouse (GB); David Jonathan Bennett, Newhouse (GB)

(73) Assignees: MSD OSS B.V., Oss (NL); Pharmacopeia, Inc., Cranbury, NJ (US)

( * ) Notice: Subject to any disclaimer, the term of this patent is extended or adjusted under 35 U.S.C. 154(b) by 284 days.

(21) Appl. No.: 12/194,146

(22) Filed: Aug. 19, 2008

(65) Prior Publication Data

US 2009/0264416 A1 Oct. 22, 2009

Related U.S. Application Data

(60) Provisional application No. 60/956,791, filed on Aug. 20, 2007.

(51) Int. Cl.
| | | |
|---|---|---|
| A01N 43/62 | (2006.01) |
| A01N 43/58 | (2006.01) |
| A01N 43/60 | (2006.01) |
| A61K 31/55 | (2006.01) |
| A61K 31/535 | (2006.01) |
| A61K 31/50 | (2006.01) |
| A61K 31/495 | (2006.01) |
| A61K 31/497 | (2006.01) |
| A61K 31/4965 | (2006.01) |
| C07D 243/00 | (2006.01) |
| C07D 487/22 | (2006.01) |
| C07D 491/00 | (2006.01) |
| C07D 498/00 | (2006.01) |
| C07D 243/08 | (2006.01) |
| C07D 413/00 | (2006.01) |
| C07D 239/02 | (2006.01) |
| C07D 241/36 | (2006.01) |
| C07D 271/00 | (2006.01) |
| C07D 487/00 | (2006.01) |
| C07D 495/00 | (2006.01) |
| C07D 497/00 | (2006.01) |
| C07D 513/00 | (2006.01) |
| C07D 417/00 | (2006.01) |
| C07D 419/00 | (2006.01) |
| C07D 241/02 | (2006.01) |
| C07D 403/00 | (2006.01) |
| C07D 411/00 | (2006.01) |
| C07D 295/00 | (2006.01) |

(52) U.S. Cl. .......... 514/218; 514/231.5; 514/235.8; 514/250; 514/252.11; 514/252.13; 514/253.01; 514/254.01; 514/254.05; 514/254.1; 514/2; 514/54.11; 514/254.03; 514/255.01; 514/254.04; 540/555; 540/575; 544/121; 544/306; 544/338; 544/357; 544/367; 544/371; 544/377; 544/379; 544/391; 544/386

(58) Field of Classification Search .......... 514/218, 514/231.5, 235.8, 250, 252, 252.11, 253.01, 514/254.1, 254.03, 254.11, 254.05, 254.04, 514/255.01; 544/338, 357, 367, 121, 360, 544/371, 377, 379, 391; 540/555, 575
See application file for complete search history.

(56) References Cited

U.S. PATENT DOCUMENTS

| | | |
|---|---|---|
| 2006/1074115 | 4/2006 | Dehmlow et al. |
| 2007/0142369 A1 | 6/2007 | Van Heck et al. |
| 2010/0029621 A1 | 2/2010 | Cooke et al. |

FOREIGN PATENT DOCUMENTS

| | | |
|---|---|---|
| EP | 0742208 | 11/1996 |
| WO | WO02/058690 | 8/2002 |
| WO | WO03/015774 A | 2/2003 |
| WO | WO2004/009091 A | 1/2004 |
| WO | WO2006/009741 A | 1/2006 |
| WO | WO2007/051920 | 5/2007 |
| WO | WO2007/092065 A | 8/2007 |
| WO | WO2009/024550 A | 2/2009 |

OTHER PUBLICATIONS

Geyeregger et. al., Cellular & Molecular Life Sciences, 2006, Birkhauser Verlag, vol. 63, pp. 524-539.*

(Continued)

Primary Examiner — Sreeni Padmanabhan
Assistant Examiner — Sarah Pihonak
(74) Attorney, Agent, or Firm — James L. McGinnis; Catherine D. Fitch; Susan Hess

(57) ABSTRACT

The present invention relates to N-benzyl,N'-arylcarbonylpiperazine derivatives having the general formula I Formula I

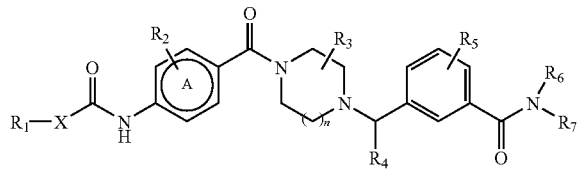

to pharmaceutical compositions comprising the same, and to the use of a these N-benzyl,N'-arylcarbonylpiperazine derivatives for the manufacture of a medicament for treating or preventing atherosclerosis and related disorders associated with cholesterol and bile acids transport and metabolism.

9 Claims, No Drawings

OTHER PUBLICATIONS

Groot et. al., Journal of Lipid Research, 2005, American Society for Biochemistry & Molecular Biology, vol. 46, pp. 2182-2191.*

Hulthe et. al., Arteriosclerosis, Thrombosis, and Vascular Biology, 2000, Lippincott, Williams & Wilkins, vol. 20, pp. 2140-2147.*

International Search Report and Written Opinion for PCT/EP2008/060788 filed Aug. 18, 2008 mailed on Dec. 10, 2008.

International Search Report for PCT/US2009/055035 filed Aug. 26, 2009 mailed on Sep. 11, 2009.

International Search Report for PCT/EP2009/055790 filed on May 14, 2009 mailed on Aug. 11, 2009.

D. J. Bennett; et. al.; "An update on non-steroidal liver X receptor antagonists and their potential use in the treatment of atherosclerosis"; Expert. Opin. Ther. Patents; vol. 16, No. 12, 2006; pp. 1673-1699.

U.S. Appl. No. 13/060,730, dated Sep. 7, 2011, Cooke et al.

* cited by examiner

N-BENZYL,N'-ARYLCARBONYLPIPERAZINE DERIVATIVES

This application is a non-provisional application that claims priority under 35 U.S.C. §119(e) of provisional application U.S. Ser. No. 60/958,791 filed Aug. 20, 2007, the contents of which are hereby incorporated by reference in their entireties.

The present invention relates to N-benzyl, N'arylcarbonylpiperazine derivatives, to pharmaceutical compositions comprising the same and to the use of these N-benzyl, N'arylcarbonylpiperazine derivatives in the treatment of atherosclerosis.

The Liver X Receptors (LXRs) are a family of nuclear receptors that are activated upon binding of the naturally occurring oxysterols inducing transcription of target genes. Two subtypes of LXR ($\alpha$ and $\beta$) have been identified and exhibit 77% homology of both their ligand- and DNA-binding domains. Both subtypes are highly conserved between humans and rodents however their tissue expression patterns differ significantly. The expression of LXR$\alpha$ is restricted to tissues involved in lipid metabolism with highest expression in the liver; there are also significant levels in kidney, spleen, small intestine and adipose tissue. LXR$\beta$ is very widely distributed and has been found in virtually every tissue examined, including liver and brain. Both LXR$\alpha$ and LXR$\beta$ are expressed in macrophages. See Costet et al., *J. Biol. Chem* 275:28240-28245 (2000).

The roles of the LXR receptors are not fully understood, however LXR is well established as a master regulator of lipid metabolism in the liver and peripheral tissues, and as the key inducer of the ATP-binding cassette transporter A1 (ABCA1) gene (Venkateswaran et al., *Proc. Natl. Acad. Set. USA.* 97:12097-12102 (2000)). In the human population, mutations of the ABCA1 gene lead to highly atherogenic lipoprotein profiles (Singaraja et al., *Arterioscler. Thromb. Vasc. Biol.* 23:1322-1332 (2003)) which in the most severe form cause Tangier's Disease and associated premature atherosclerosis, (see Bodzioch et al., *Nat. Genet.* 22:347-351 (1999) and Rust et al., *Nat. Genet.* 22:352-355 (1999)). This rare inherited disorder is characterised by very low levels of high density lipoproteins (HDL), macrophage accumulation of cholesterol esters and significantly increased risk of atherosclerotic disease (Brooks-Wilson et al., *Nat. Genet.* 22:336-345 (1999)).

Evidence has demonstrated that up-regulation of ABCA1 in human macrophages and enterocytes of the small intestine, is mediated by LXR activation (Costet et al., supra). Furthermore, LXR agonists have also been shown to promote cholesterol efflux. See Claudel et al., *Proc. Natl. Acad. Sci. USA.* 98:2610-2615 (2001). LXR receptors therefore play a critical role in cholesterol homeostasis In macrophages, and suppression within the local environment of the advanced atherosclerotic plaque may be a key feature of the pathology of the disease.

The potential utility of LXR agonists in the treatment of atherosclerosis has been increasingly documented over the last few years. See for example Levin et al., *Arterioscler. Thromb. Vasc. Biol.* 25:135-142 (2005). Atherosclerosis is a disease of the arteries that exists for many years without causing symptoms. Advanced atherosclerotic plaques can however become vulnerable to rupture, promoting acute thrombosis and clinical events such as myocardial infarction (MI) and stroke. The primary cell type implicated in rupture of atherosclerotic plaques, and subsequent clinical events, is the macrophage.

The primary mechanism for achieving efficacy in atherosclerosis with an LXR agonist is expected to occur by lowering the cholesterol burden of arteries (via upregulation of ABCA1), to generate more stable lesions and thus reduce the clinical events. Additionally, LXR agonists may increase circulating HDL levels due to the role of ABCA1 in generation of nascent HDL by the liver. There is potential for further anti-atherosclerotic effects of LXR agonists due to suppression of inflammation (Joseph et al., *Nat. Med.* 9:213-219 (2003)) and effects on glucose metabolism. See Latiffe et al., *Proc. Natl. Acad. Sci. USA.* 100:5419-24 (2003).

There is a remaining need for compounds that are effective as LXR modulators.

To this aim the present invention provides N-benzyl,N'-arylcarbonylpiperazine derivatives having the general formula I Formula I

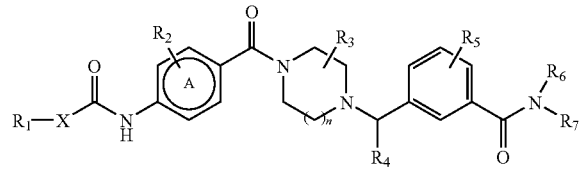

wherein
n is 1 or 2;
A is a 6-membered aromatic ring optionally containing 1 or 2 nitrogen atoms;
X is $NR_8$, O or a bond;
$R_1$ is H, $(C_{1-8})$alkyl [optionally substituted with halogen, $(C_{1-4})$alkyloxy, $(C_{1-4})$alkyoxycarbonyl, $(C_{3-8})$cycloalkyl, OH, $CF_3$, cyano or $NR_9R_{10}$], $(C_{2-6})$alkynyl, $(C_{3-8})$cycloalkyl, phenyl [optionally substituted with $(C_{1-4})$alkyl, $(C_{1-4})$alkyloxy, halogen, CN, $CF_3$, $OCF_3$ or $NO_2$], a 5- or 6-membered saturated heterocyclic group containing 1 or 2 heteroatoms selected from O and S, or a 5- or 6-membered heteroaryl group containing 1-3 heteroatoms selected from O, S and N [optionally substituted with $(C_{1-4})$alkyl, $(C_{1-4})$alkyloxy, halogen or $CF_3$]; or
$R_1$ is $(C_{1-3})$alkyl substituted with phenyl [optionally substituted with $(C_{1-4})$alkyl, $(C_{1-4})$alkyloxy, halogen or with 2 substituents at adjacent positions forming O—$(CH_2)$n-O, wherein n is 1 or 2], a 5- or 6-membered heteroaryl group containing 1-3 heteroatoms selected from O, S and N [optionally substituted with $(C_{1-3})$alkyl, $(C_{1-3})$alkyloxy or halogen], or a 5- or 6-membered saturated heterocyclic group containing 1 or 2 heteroatoms selected from O, S and N [optionally substituted with $(C_{1-4})$alkyl, $(C_{1-4})$alkyloxy, oxo, OH or halogen]; or when X is $NR_8$, $R_1$ may together with $R_8$ and the N to which they are bonded form a 4-8 membered ring optionally containing a further heteroatom selected from O and S [and which ring is optionally substituted with OH, $(C_{1-4})$alkyl, $(C_{1-4})$alkyloxy or halogen];
$R_2$ optionally represents 1-3 substituents independently selected from $(C_{1-4})$alkyl, $(C_{1-4})$ alkyloxy, $CF_3$ and halogen;
$R_3$ optionally represents 1-4 substituents independently selected from $(C_{1-4})$alkyl and $(C_{1-4})$alkyl substituted by OH or 1 or more halogens;
$R_4$ is H or $(C_{1-6})$alkyl;
$R_5$ optionally represents 1-3 substituents independently selected from $(C_{1-3})$alkyl, $(C_{1-3})$alkyloxy and halogen;
$R_6$ is H, $(C_{1-6})$alkyl [optionally substituted with halogen, $CF_3$ or CN], $(C_{3-6})$cycloalkyl [optionally containing a heteroatom selected from O and S, and optionally substituted by CN or phenyl], $(C_{3-6})$cycloalkyl$(C_{1-4})$alkyl, or a 5- or 6-membered (hetero)aryl group, optionally linked through a methylene group, and optionally substituted with $(C_{1-4})$alkyl, $(C_{1-4})$alkyloxy, $(C_{1-4})$-alkylsulfonyl, halogen, CN, $CF_3$, $CF_3O$ or $NO_2$];

$R_7$ is H or $(C_{1-3})$alkyl;

$R_8$, when present, is H or $(C_{1-3})$alkyl; or $R_8$ together with $R_1$ and the N to which they are bonded form a 4-8 membered ring optionally containing a further heteroatom selected from O and S [and which ring is optionally substituted with OH, $(C_{1-3})$alkyl, $(C_{1-3})$alkyloxy or halogen];

$R_9$ and $R_{10}$ are independently selected from H, $(C_{1-3})$alkyl or $(C_{1-3})$alkylcarbonyl; or $R_9$ and $R_{10}$ together with the N to which they are bonded form a 4-8 membered ring optionally containing a further heteroatom selected from O and S;

or a pharmaceutical acceptable salt thereof.

The term $(C_{1-8})$alkyl as used in the definition of Formula I means a branched or unbranched alkyl group having 1-8 carbon atoms, like octyl, hexyl pentyl, isopentyl, butyl, isobutyl, tertiary butyl, propyl, isopropyl, ethyl and methyl.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

Likewise, the term $(C_{1-3})$alkyl used in the definition of Formula I means a branched or unbranched alkyl group having 1-3 carbon atoms, like propyl, isopropyl, ethyl and methyl.

The term $(C_{2-6})$alkenyl means a branched or unbranched alkenyl group having 2-6 carbon atoms, such as ethenyl, propyn-2-yl, 2-methyl-propenyl, penten-4-yl and the like.

The term $(C_{2-6})$alkynyl means a branched or unbranched alkynyl group having 2-6 carbon atoms, such as ethynyl, propyn-2-yl, pentyn-4-yl and the like.

The term $(C_{3-8})$cycloalkyl means a cycloalkyl group having 3-8 carbon atoms, like cycloheptyl, cyclohexyl, cyclopentyl, cyclobutyl and cyclopropyl. In the definition of $R_6$ in Formula I the $(C_{3-8})$cycloalkyl group may contain a heteroatom selected from O and S to form a saturated heteroaromatic ring such as tetrahydrofuranyl, tetrahydrothienyl, tetrahydropyranyl and tetrahydrothiopyranyl.

The term a 5- or 6-membered heteroaryl group containing 1-3 heteroatoms selected from O, S and N, is exemplified by oxazolyl, isoxazolyl, oxadiazolyl, thiadiazolyl, furanyl, pyrrolyl, furazanyl, pyrazolyl, pyrazinyl, pyridinyl, pyrimidinyl, imidazolyl, thiazolyl, thiadiazolyl, thienyl and the like.

The term a 5- 6-membered saturated heterocyclic group containing 1 or 2 heteroatoms selected from O and S is exemplified by tetrahydrofuranyl, tetrahydrothienyl, tetrahydropyranyl and tetrahydrothiopyranyl.

The term a 5- 6-membered saturated heterocyclic group containing 1 or 2 heteroatoms selected from O, S and N is exemplified by tetrahydrofuranyl, tetrahydrothienyl, tetrahydro-pyranyl, tetrahydrothiopyranyl, morpholin-1-yl, thiomorpholin-1-yl, piperidinyl, pyrrolidinyl, imidazolidinyl and the like.

The term halogen means F, Cl, Br or I.

There is a preference for N-benzyl,N'-arylcarbonylpiperazine derivatives of formula wherein X is NH and n is 1.

Further preferred are the N-benzyl,N'-arylcarbonylpiperazine derivatives of formula I, wherein in addition A is phenyl.

More preferred are the compounds of formula I wherein $R_1$ is $(C_{1-8})$alkyl [optionally substituted with $(C_{3-8})$cycloalkyl], $(C_{2-6})$alkenyl, $(C_{3-8})$cycloalkyl or phenyl [optionally substituted with halogen].

Also preferred are the N-benzyl,N'-arylcarbonylpiperazine derivatives of formula I wherein $R_3$ is absent or represents methyl, and wherein $R_5$ is absent or represents halogen.

Especially preferred are the N-benzyl,N'-arylcarbonylpiperazine derivatives of formula I wherein in addition $R_6$ is $(C_{1-5})$alkyl optionally substituted with $CF_3$, and $R_7$ is H.

Particular N-benzyl,N'-arylcarbonylpiperazine derivatives of the invention are:

N-tert-butyl-3-((4-(4-(3-(cyclopropylmethyl)ureido)benzoyl)piperazin-1-yl)methyl)benzamide 2,2,2-trifluoroacetate;

N-tert-butyl-3-((4-(4-(3-neopentylureido)benzoyl)piperazin-1-yl)methyl)benzamide 2,2,2-trifluoroacetate;

N-tert-butyl-3-((4-(3-fluoro-4-(3-neopentylureido)benzoyl)piperazin-1-yl)methyl)benzamide;

N-tert-butyl-3-((4-(3-fluoro-4-(3-cyclobutylureido)benzoyl)piperazin-1-yl)methyl)benzamide;

N-tert-butyl-3-((4-(4-(3-(cyclopropylmethyl)ureido)-3-fluorobenzoyl)piperazin-1-yl)methyl)benzamide;

N-tert-butyl-3-((4-(3-fluoro-4-(3-isobutylureido)benzoyl)piperazin-1-yl)methyl)benzamide;

N-tert-butyl-3((4-(3-fluoro-4-(3-isopentylureido)benzoyl)piperazin-1-yl)methyl)benzamide;

N-tert-butyl-3-((4-(4-(3-(cyclobutylmethyl)ureido)-3-fluorobenzoyl)piperazin-1-yl)methyl)benzamide;

N-tert-butyl-3-((4-(4-(3-butylureido)-3-fluorobenzoyl)piperazin-1-yl)methyl)benzamide;

N-tert-butyl-3-((4-(4-(3-(2-cyclopropylethyl)ureido)-3-fluorobenzoyl)piperazin-1-yl)methyl)benzamide;

3-((4-(4-(3-neopentylureido)benzoyl)piperazin-1-yl)methyl)-N-(1,1,1-trifluoro-2-methylpropan-2-yl)benzamide;

3-((4-(4-(3-butylureido)benzoyl)piperazin-1-yl)methyl)-N-(1,1,1-trifluoro-2-methylpropan-2-yl)benzamide;

3-((4-(4-(3-isobutylureido)benzoyl)piperazin-1-yl)methyl)-N-(1,1,1-trifluoro-2-methylpropan-2-yl)benzamide;

3-((4-(3-fluoro-4-(3-neopentylureido)benzoyl)piperazin-1-yl)methyl)-N-(1,1,1-trifluoro-2-methylpropan-2-yl)benzamide;

3-((4-(4-(3-(cyclopropylmethyl)ureido)-3-fluorobenzoyl)piperazin-1-yl)methyl)-N-(1,1,1-trifluoro-2-methyl-propan-2-yl)benzamide hydrochloride;

N-tert-butyl-3-((4-(3-chloro-4-(3-cyclobutylureido)benzoyl)piperazin-1-yl)methyl)benzamide;

N-tert-butyl-3-((4-(3-chloro-4-(3-(cyclopropylmethyl)ureido)benzoyl)piperazin-1-yl)methyl)benzamide;

N-tert-butyl-3-((4-(3-chloro-4-(3-neopentylureido)benzoyl)piperazin-1-yl)methyl)benzamide;

N-tert-butyl-3-((4-(3-chloro-4-(3-isobutylureido)benzoyl)piperazin-1-yl)methyl)benzamide;

1-(3-(tert-butylcarbamoyl)benzyl)-4-(3-chloro-4-(3-(cyclobutylmethyl)ureido)benzoyl)-piperazine 1-oxide;

N-tert-butyl-3-((4-(4-(3-butylureido)-3-chlorobenzoyl)piperazin-1-yl)methyl)benzamide;

N-tert-butyl-3-((4-(3-chloro-4-(3-isopentylureido)benzoyl)piperazin-1-yl)methyl)benzamide;

N-tert-butyl-3-((4-(2,3-difluoro-4-(3-neopentylureido)benzoyl)piperazin-1-yl)methyl)benzamide;

N-tert-butyl-3-((4-(2,3-difluoro-4-(3-isopentylureido)benzoyl)piperazin-1-yl)methyl)benzamide;

N-tert-butyl-3-((4-(4-(3-butylureido)-2,3-difluorobenzoyl)piperazin-1-yl)methyl)benzamide;

N-tert-butyl-3-((4-(2,3-difluoro-4-(3-isobutylureido)benzoyl)piperazin-1-yl)methyl)benzamide;

N-tert-butyl-3-((4-(4-(3-(cyclopropylmethyl)ureido)-2,3-difluorobenzoyl)piperazin-1-yl)methyl)benzamide;

N-tert-butyl-3-((4-(4-(3-cyclobutylureido)-2,3-difluorobenzoyl)piperazin-1-yl)methyl)benzamide hydrochloride;

N-tert-butyl-3-((4-(3-chloro-4-(3-(cyclopropylmethyl)ureido)-2-fluorobenzoyl)piperazin-1-yl)methyl)benzamide;

N-tert-butyl-3-((4-(3-chloro-2-fluoro-4-(3-isobutylureido)benzoyl)piperazin-1-yl)methyl)benzamide.

N-tert-butyl-3-((4-(4-(3-cyclobutylureido)benzoyl)piperazin-1-yl)methyl)-2-fluorobenzamide;

N-tert-butyl-2-fluoro-3-((4-(4-(3-neopentylureido)benzoyl)piperazin-1-yl)methyl)benzamide;

N-cyclobutyl-3-((4-(3-fluoro-4-(3-neopentylureido)benzoyl)piperazin-1-yl)methyl)benzamide; and (R)—N-sec-butyl-3-((4-(3-fluoro-4-(3-neopentylureido)benzoyl)piperazin-1-yl)methyl)benzamide; or a pharmaceutically acceptable salt thereof.

The N-benzyl,N'arylcarbonylpiperazine derivatives of the invention can be prepared using general synthetic methods known in the art of organic synthesis, for instance by using synthetic routes depicted in Scheme 1.

Those skilled in the art will know that the order of addition of the key building blocks according to Formulas 2-8 can be altered and still give the desired products of Formula 1. Following one such route, a (homo)piperazine intermediate of Formula 2, wherein Y represents an amino protecting group, such as for example a tert-butyloxycarbonyl group (t-Boc), and $R_3$ has the meaning as previously defined, is alkylated with a benzamide derivative of Formula 3, wherein $R_4$, $R_5$, $R_6$ and $R_7$ have the previously defined meaning and wherein L represents a leaving group such as chloro or bromo, in a solvent e.g. dichloromethane or acetonitrile at room or elevated temperature using an organic base e.g. triethylamine or inorganic base e.g. potassium carbonate to give an intermediate N-benzyl(hom)piperazine derivative of Formula 5.

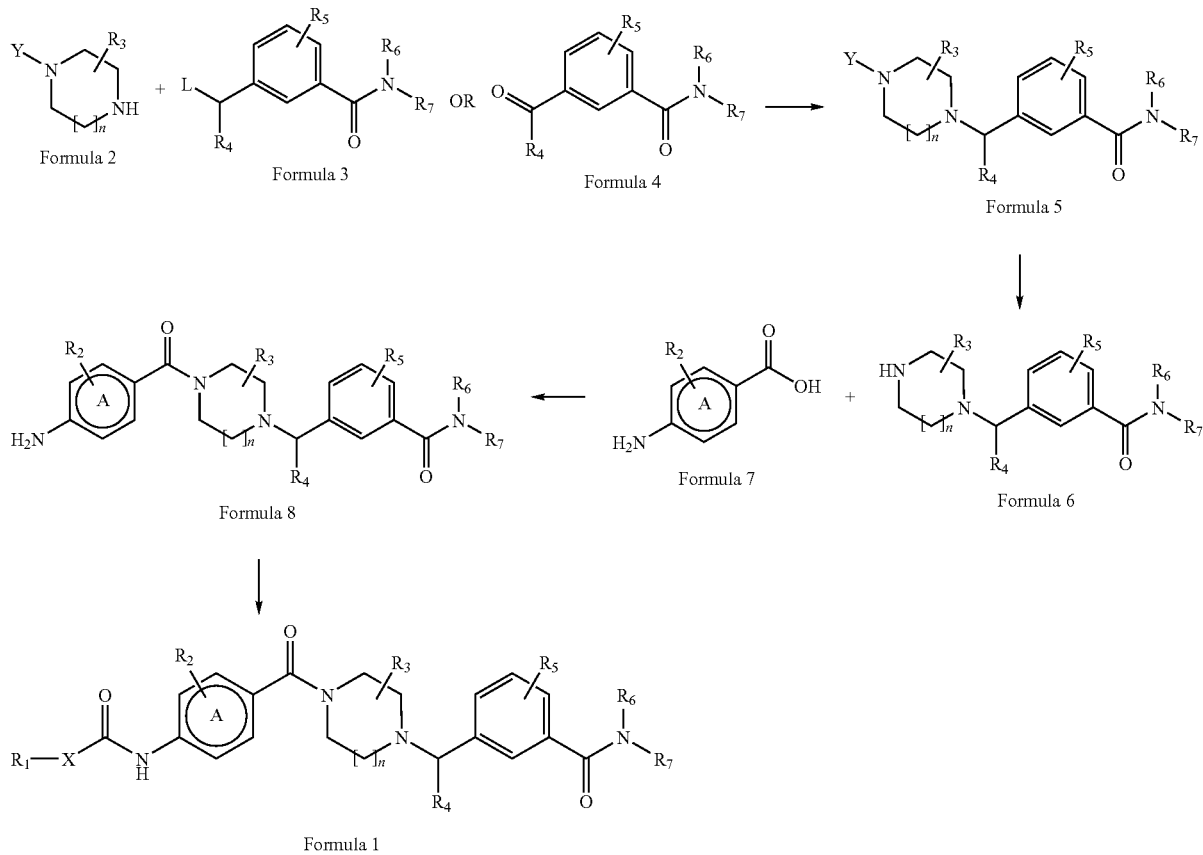

Scheme 1

As an alternative, the intermediates of Formula 5 can be obtained from a reductive amination reaction between the (homo)piperazine intermediate of Formula 2 with the intermediate benzamide derivative of Formula 4, wherein $R_4$, $R_5$, $R_6$ and $R_7$ have the meaning as previously defined, which reaction can be carried out in a solvent e.g. dichloromethane using a reducing agent e.g. sodium triacetoxyborohydride.

Deprotection of the Boc-protected intermediate of Formula 5, e.g. using trifluoroacetic acid and dichloromethane, provides the intermediate piperazine derivatives of Formula 6, which are subsequently coupled with a benzoic acid derivative of Formula 7, wherein $R_2$ has the meaning as previously defined, in a solvent e.g. dichloromethane using a coupling agent e.g. N-(3-dimethylaminopropyl)-N'-ethylcarbodiimide hydrochloride or 1-propanephosphonic acid cyclic anhydride, to give the N-benzyl,N'-benzoylpiperazine intermediate of Formula 8. Compounds of the invention according to Formula I wherein X is $NR_8$, and wherein $R_1$ and $R_8$ have the meaning as previously defined, can be prepared from the intermediates of Formula 8 by reaction with 4-nitrophenylchloroformate or with (bis(trichloromethyl) carbonate (triphosgene) in a solvent e.g. dichloromethane at room or elevated temperature, followed by additions of the desired amine of Formula $R_1, R_8NH$, wherein $R_1$ and $R_8$ have the meaning as previously defined, in the presence of a base e.g. triethylamine.

Compounds of the invention wherein X is NH can also be prepared by reacting a N-benzyl,N'-benzoylpiperazine intermediate of Formula 8 with an isocyanate of formula $R_1$—NCO, wherein $R_1$, has the meaning as previously defined, in solvent e.g. dichloromethane. Compounds of Formula I wherein X is O can be prepared by reaction from an intermediate of Formula 8 with 4-nitrophenylchloroformate or triphosgene in a solvent e.g. dichloromethane at room or elevated temperature, followed by addition of an excess of an alcohol of formula $R_1$—OH, wherein $R_1$ has the meaning as previously defined.

Compounds of the invention wherein X is a bond can be prepared by reacting a N-benzyl,N'-benzoylpiperazine intermediate of Formula 8 with an acid chloride of formula $R_1CO_2Cl$, wherein $R_1$, has the meaning as previously defined, in a solvent e.g. dichloromethane in the presence of an organic base e.g. triethylamine at room or elevated temperatures, or alternatively, by reaction with an acid derivative of formula $R_1COOH$, wherein $R_1$ has the meaning as previously defined, in a solvent e.g. dichloromethane using a coupling reagent e.g. N(3-dimethylaminopropyl)-N'-ethylcarbodiimide hydrochloride or 1-propanephosphonic acid cyclic anhydride and base e.g. triethylamine.

The intermediate piperazine derivative of Formula 2, the benzamide derivatives of Formula 3 and Formula 4, as well as the 4-aminobenzoic acid derivatives of formula 7 are compounds that can be prepared using methods well known in the art from commercially available intermediates.

The term N-protecting group, as used above, means a group commonly used for the protection of an amino group, like the alloxycarbonyl (Alloc) group, the tert-butyloxycarbonyl (Boc) group, the benzyloxycarbonyl (Z) group or the 9-fluorenylmethyloxycarbonyl(Fmoc) group. Removal of these and other protecting groups can take place in different ways, depending on the nature of those protecting groups. An overview of protecting groups and methods for their removal is given in T. W. Greene and P. G. M. Wuts, *"Protective Groups in Organic Synthesis"*, 2nd edition, 1991, John Wiley & Sons, Inc.

The N-benzyl,N'arylcarbonylpiperazine derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers.

Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

Pharmaceutically acceptable salts may be obtained by treating a free base of a compound of formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid, methane sulfonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a N-benzyl, N'arylcarbonylpiperazine derivative having the general Formula I, or a pharmaceutically acceptable salt thereof, in admixture with pharmaceutical acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multidose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., *Remington; The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as filters, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The N-benzyl,N'arylcarbonylpiperazine derivatives of the present invention were found to be modulators of LXRα, especially having agonistic activity thereon, and are as such useful in preventing and reducing the risk of atherosclerosis and related disorders associated with cholesterol and bile acids transport and metabolism, such as hypercholesterolemia (e.g. coronary heart disease), cholesterol gallstones, lipid storage diseases, diabetes and obesity. The compounds of the invention are potentially also useful in further indications such as:

Inflammatory Disease:

Ligand activation of LXR has been shown to inhibit a number of inflammatory pathways e.g. Interleukin1-β, Interleukin-6, cyclooxygenase-2 and most recently shown to directly inhibit C-reactive protein expression. See Blaschke et al., *Circ. Res.* 99:88-99. (2008). Compounds of the invention may have therapeutic utility in suppression of inflammation in inflammatory diseases such as contact dermatitis (see Fowler et al., *J. Invest. Dermatol.* 120:246-55. (2003); neuroinflammatory diseases such as multiple sclerosis (Zhang-Gandhi and Drew. *J. Neuroimmunol.* 183:50-59. (2007)) and autoimmune encephalomyelitis. See Hindinger et al., *J. Neurosci. Res.* 84:1225-1234 (2006).

Proliferative Vascular Disease:

The LXR ligand T0901317 has been shown to inhibit vascular smooth muscle cell proliferation and neointima formation following balloon injury in vitro and in vivo. Compounds of the invention may therefore have therapeutic utility in proliferative vascular diseases. See Blaschke et al., *Circ. Res.* 95:110-123 (2004).

Diabetes/Metabolic Syndrome:

Recent literature has demonstrated efficacy of LXR agonists in animal models of insulin resistance and diabetes and thus compounds of the invention may have potential therapeutic utility in the treatment of diabetes and metabolic syndrome (see Liu et al., *Endocrinology*. 147:5061-5068 (2006); Fernandez-Veledo et al., *Diabetologia*. 49:3038-3048 (2006)).

Cancer:

The LXR agonist T0901317 delayed progression of tumours in an animal model of prostate cancer. Compounds of the invention may be potentially useful for treatment of prostate cancer. See Chuu et al., *Cancer.Res.* 66:6482-6486 (2006).

Neurodegenerative Disease:

Via modulation of cellular cholesterol levels, LXR agonists can reduce the deposition of β-amyloid in the brain. In addition T0901317 has been shown to lower deposition of β-amyloid but also improve memory. See Riddell et al., *Mol. Cell. Neurosci.* 34:621-628 (2007). The agonist derivatives of the present invention may therefore have therapeutic utility in neurodegenerative diseases such as Alzheimers disease.

Combination Therapies:

The compounds of the invention may be combined with another therapeutic agent that is useful in the treatment of other metabolic disorders such as; hypertension, hyperlipidaemias, dyslipidaemias, diabetes, chronic inflammatory disorders, obesity and in any condition where enhancement of reverse cholesterol transport and/or improvement of LDL: HDL ratios would be of potential clinical benefit. Examples of such therapies are: inhibitors of 3-hydroxy-3-methyl-glutaryl-CoA reductase (HMG CoA reductase) (e.g. atorvastatin, pravastatin, simvastatin, lovastatin, rosuvastatin and others), cholesterol absorption inhibitors (e.g. ezetimibe), bile sequestrants (e.g. cholestyramine), microsomal triglyceride transfer protien (MTP) inhibitors, peroxisome proliferator-activated receptor modulators (e.g. muraglitazar, rosiglitazone, fibrates and others), cholesterol ester transfer protien inhibitors, nicotinic acid derivatives (e.g. Niaspan® etc), Acyl coenzyme A: cholesterol acyl transferase (ACAT) inhibitors (e.g. eflucimibe), farnesoid X receptor modulators, therapies used for the treatment of metabolic syndrome or type 2 diabetes e.g. metformin. Compounds of the invention may be combined with anti-inflammatory therapies (e.g. aspirin) and with treatments for neurodegenerative diseases (e.g Aricept®, Exelon®, Reminyl® and Ebixa®).

The compounds of the invention may be administered for humans in a sufficient amount and for a sufficient amount of time to alleviate the symptoms, illustratively, dally dosage levels for humans can be in the range of 0.001-50 mg per kg body weight, preferably in a daily dosage of 0.01-20 mg per kg body weight.

The invention is illustrated by the following Examples.

GENERAL EXPERIMENTAL

High Performance Liquid Chromatography (HPLC)

HPLC purification is used within this experimental section and refers to High Performance Liquid Chromatography. Some examples of general methods that may be used to purify compounds are: acidic reverse phase HPLC (water/acetonitrile/0.1% trifluoroacetic acid) using a standard gradient of 5% acetonitrile/95% water to 100% acetonitrile or basic reverse phase HPLC (water/acetonitrile/0.1% ammonia solution) using a standard gradient of 10% acetonitrile/90% water to 100% acetonitrile. UV detection e.g. 254 nM is used for the collection of fractions from HPLC. This description gives general methods and variations in types of equipment, columns, mobile phase, detection wavelength, solvent gradient and run time may also be used to purify compounds.

Free Base and Salts

After purification by acidic HPLC basic products can either be isolated as the trifluoroacetic acid salt or liberated as the free base by common generic methods e.g. strong cation exchange chromatography eluting with 2M ammonia in methanol or silica carbonate column chromatography or partitioning between an organic solvent e.g. ethyl acetate and aqueous base e.g. sodium hydrogen carbonate, separating the organic layer, drying with inorganic solid e.g. magnesium sulfate, filtering and concentration under reduced pressure. The free base of products can also be converted to hydrochloride salts by standard methods e.g. dissolving the free base in dichloromethane and adding 2M hydrochloric acid in ether and concentrating under reduced pressure to give the hydrochloride salt.

Abbreviations:

Boc: tert-butoxycarbonyl; CDCl$_3$: chloroform-d; CD$_3$OD: methanol-d4; HPLC: high performance liquid chromatography; HOBt: 1H-benzo[d][1,2,3]triazol-1-ol; HATU: O-(7-azabenzotriazol-1-yl)-N,N,N,N-tetramethyl uronium hexafluorophosphate; EDCl: N-(3-dimethylaminopropyl)-N'-ethylcarbodiimide hydrochloride.

Example 1

N-tert-Butyl-3-((4-(4-(3-(cyclopropylmethyl)ureido) benzoyl)piperazin-1-yl)methyl)benzamide 2,2,2-trifluoroacetate

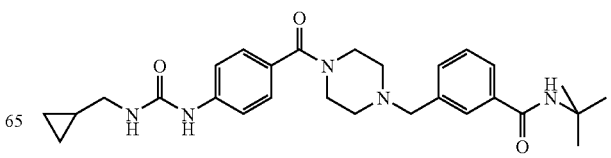

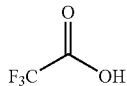

A: N-tert-Butyl-3-(piperazin-1-ylmethyl)benzamide Dihydrochloride

Step 1:
3-(Chloromethyl)benzoyl chloride (2.26 ml, 15.9 mmol) was added to a stirred solution of dichloromethane (50 mL) at −30° C. (cold-bath temperature) under argon. After 10 minutes stirring, a solution of tert-butylamine (1.66 mL, 15.9 mmol) and N-ethyl-N-isopropylpropan-2-amine (5.53 mL, 31.7 mmol) in dichloromethane (5 mL) was added dropwise. Stirring was continued while allowing the cold-bath temperature to slowly increase to −15° C. over 45 minutes. The reaction mixture was concentrated under vacuum to give the intermediate N-tert-butyl-3-(chloromethyl)benzamide as a white solid.

Step 2:
The N-tert-butyl-3-(chloromethyl)benzamide was placed under an argon atmosphere and treated with a solution of tert-butyl 1-piperazine-carboxylate (2.96 g, 15.9 mmol) and N-ethyl-N-isopropylpropan-2-amine (5.53 mL, 31.7 mmol) in dimethyl sulfoxide (15 mL) at room temperature. The reaction mixture was stirred overnight, diluted with ethyl acetate (100 mL) and washed with saturated aqueous sodium chloride (×5). The organic phase was dried on magnesium sulfate, filtered and concentrated under vacuum to give a crude oil. This oil was purified by iterative rounds of silica chromatography (20-70% ethyl acetate in n-hexanes, followed by 0-6% methanol in dichloromethane) to give the intermediate tert-butyl 4-(3-(tert-butylcarbamoyl)benzyl)piperazine-1-carboxylate (5.04 g).

Step 3:
The intermediate tert-butyl 4-(3-(tert-butylcarbamoyl)benzyl)piperazine-1-carboxylate (5 g, 13.3 mmol) was stirred with a 14% wt./wt. solution of dry hydrochloric acid in anhydrous ethanol (20 mL) for 4 hours at room temperature. The solution was then concentrated under vacuum to afford the title compound (4.66 g).
MS (ESI) m/z 276.2 [M+H]$^+$

B: N-tert-Butyl-3-((4-(4-nitrobenzoyl)piperazin-1-yl)methyl)benzamide

N-tert-Butyl-3-(piperazin-1-ylmethyl)benzamide dihydrochloride (0.50 g, 1.44 mmol) was suspended in stirred dichloromethane (20 mL) at 0° C. (ice-bath) under an argon atmosphere. N-ethyl-N-isopropylpropan-2-amine (1.0 mL, 5.75 mmol) was added slowly. After 10 minutes stirring, the resulting solution was treated with a suspension of 4-nitrobenzoyl chloride (0.267 g, 1.44 mmol) In dichloromethane (10 ml). The ice-bath was removed and stirring continued for 1 hour. The solution was diluted with dichloromethane (70 mL) and washed with water (×4). The organic phase was dried on magnesium sulfate, filtered and concentrated under vacuum to give the title compound (0.58 g) as a yellow foam.
MS (ESI) m/z 425 [M+H]$^+$

C: 3-((4-(4-Aminobenzoyl)piperazin-1-yl)methyl)-N-tert-butylbenzamide

N-tert-Butyl-3((4-(4-nitrobenzoyl)piperazin-1-yl)methyl)benzamide (0.56 g, 1.31 mmol) was dissolved In methanol (10 mL) at room temperature. Raney 2800 nickel (~1mL of an aqueous suspension) was added and the grey suspension was stirred vigorously. A balloon of hydrogen was attached to the flask via a three-way stopcock and hydrogen was allowed to slowly flow through the system for 1 minute. The flask was sealed under 1 atmosphere of hydrogen and vigorous stirring continued for 1 hour. The balloon was removed and the flask was flushed with argon. The suspension was gravity-filtered over fluted paper and washed with methanol. The filtrate was concentrated to a crude foam/glass and silica chromatography (70-90% ethyl acetate in n-hexanes with 1-3% methanol, followed by 1-6% methanol in dichloromethane) gave the title compound (0.35 g).
MS (ESI) m/z 395.1 [M+H]$^+$

D: N-tert-Butyl-3-((4-(4-(3-(cyclopropylmethyl)ureido)benzoyl)piperazin-1-yl)methyl)benzamide 2,2,2-trifluoroacetate To a stirred solution of 3-((4-(4-aminobenzoyl)piperazin-1-yl)methyl)-N-tert-butyl-benzamide (30 mg, 0.122 mmol) in dichloromethane (2 mL) at −78° C. was added dropwise a solution of 4-nitrophenyl chloroformate (25 mg, 0.122) in dichloromethane (1 mL). The reaction mixture was allowed to stir at −78° C. for 30 minutes and slowly allowed to warm to room temperature within 2 hours. Cyclopropylmethylamine (100 mg, 1.41 mmol) was added and stirring at room temperature was continued for 18 hours. The reaction was concentrated under vacuum and the resulting residue was purified by acidic reverse phase HPLC to give the title compound (30 mg). MS (ESI) m/z 492.1 [M+H]$^+$ The following compounds were prepared in a similar manner:

1B: N-tert-Butyl-3-((4-(4-(3-neopentylureido)benzoyl)piperazin-1-yl)methyl)benzamide 2,2,2-trifluoroacetate

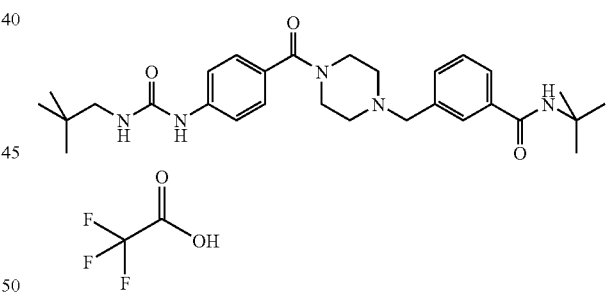

MS (ESI) m/z 508.1 [M+H]$^+$

1C: N-tert-Butyl-3-((4-(4-(3-cyclobutylureido)benzoyl)piperazin-1-yl)methyl)benzamide Hydrochloride

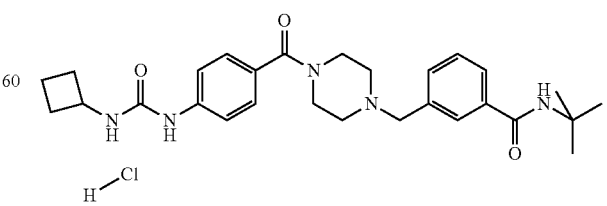

MS (ESI) m/z 492.1 [M+H]$^+$

1D: N-(4-(4-(3-(tert-Butylcarbamoyl)benzyl)piperazine-1-carbonyl)phenyl)piperidine-1-carboxamide 2,2,2-trifluoroacetate

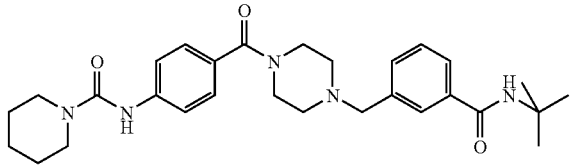

-continued

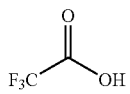

MS (ESI) m/z 506.1 [M+H]+

Example 2

N-tert-Butyl-3-((4-(4-(3-isoxazol-3-ylureido)benzoyl)piperazin-1-yl)methyl)benzamide

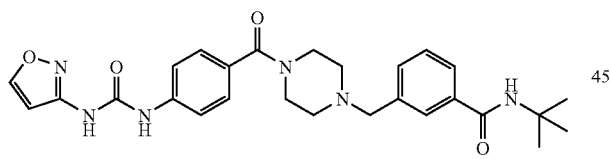

3-((4-(4-Aminobenzoyl)piperazin-1-yl)methyl)-N-tert-butylbenzamide (0.152 mmol, 60 mg) was dissolved in dichloromethane (12 mL) and a solution of 4-nitrophenyl chloroformate (0.152 mmol, 30.7 mg) in dichloromethane (20 mL) was added dropwise. The reaction was stirred for 2 hours at room temperature. Isoxazol-3-amine (1.521 mmol, 128 mg) was added and the resulting mixture was stirred at room temperature overnight. The reaction mixture was concentrated under vacuum and the residue dissolved in dichloromethane. This solution was loaded onto a strong cation exchange column and washed with dichloromethane (20 mL) then methanol (20 mL). The column was then eluted with 2M ammonia in methanol (20 mL) and the eluent was concentrated under vacuum. The residue was purified by acidic reverse phase HPLC and lyophilised to give the title compound (46 mg).

MS (ESI) m/z 505.8 [M+H]+

The following compounds were prepared in a similar manner:

2B: N-tert-Butyl-3-((4-(4-(3-(2,2-difluoroethyl)ureido)benzoyl)piperazin-1-yl)methyl)benzamide
MS (ESI) m/z 502.3 [M+H]+

2C: N-tert-Butyl-3-((4-(4-(3-isopropyl-3-methylureido)benzoyl)piperazin-1-yl)methyl-benzamide
MS (ESI) m/z 494.2 [M+H]+

2D: N-tert-Butyl-3-((4-(4-(3-(tetrahydro-2H-pyran-4-yl)ureido)benzoyl)piperazin-1-yl)methyl)benzamide
MS (ESI) m/z 522.8 [M+H]+

2E: N-(4-(4-(3-(tert-Butylcarbamoyl)benzyl)piperazine-1-carbonyl)phenyl)-4-hydroxy-piperidine-1-carboxamide

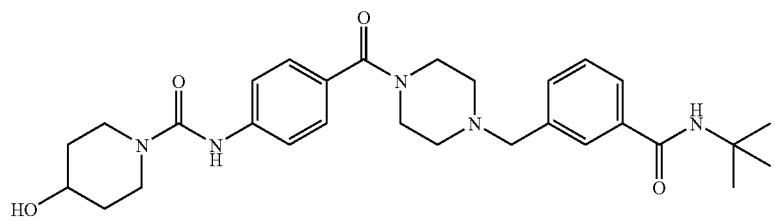

MS (ESI) m/z 522.2 [M+H]+

Example 3

Cyclopropylmethyl 4-(4-(3-(tert-butylcarbamoyl)benzyl)piperazine-1-carbonyl)phenylcarbamate 2,2,2-trifluoroacetate

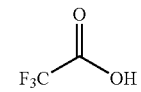

To a stirred solution of 3-((4-(4-aminobenzoyl)piperazin-1-yl)methyl)-N-tert-butylbenzamide (14 mg, 0.036 mmol) in dichloromethane (1 mL) at −78° C. was added dropwise a solution of 4-nitrophenyl chloroformate (7.3 mg, 0.036 mmol) in dichloromethane (1 ml). The mixture was left to stir at −78° C. for 30 minutes, then allowed to gradually warm up to room temperature within 2 hours. An excess of cyclopropyl methanol (~20 equivalents) was added, followed by N,N-dimethylpyridin-4-amine (5 mg), and the reaction mixture was stirred at room temperature for 18 hours. The reaction was concentrating under vacuum and purified by acidic reverse phase HPLC to give the title compound (8.8 mg) as a colorless oil. MS (ESI) m/z 493.1 [M+H]+

The following compound was prepared by a similar manner:

3B: Neopentyl 4-(4-(3-(tert-butylcarbamoyl)benzyl)piperazine-1-carbonyl)phenylcarbamate-2,2,2-trifluoroacetate
MS (ESI) m/z 509.1 [M+H]+

Example 4

N-tert-Butyl-3-((4-(4-(2-cyclobutylacetamido)benzoyl)piperazin-1-yl)methyl)benzamide 2,2,2-trifluoroacetate

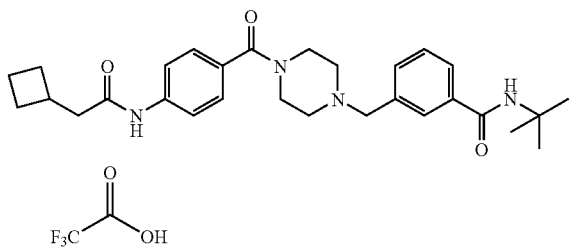

A mixture of 3-((4-(4-aminobenzoyl)piperazin-1-yl)methyl)-N-tert-butylbenzamide (20 mg, 0.05 mmol), cyclobutyl acetic acid (6 mg, 0.05 mmol) and O-(7-azabenzotriazol-1-yl)-N,N,N,N-tetramethyl uranium hexafluorophosphate (19 mg, 0.05 mmol, HATU) in N,N-dimethylformamide (0.5 mL) was stirred at room temperature for 18 hours. The crude mixture was then subjected to acidic reverse phase HPLC purification to afford the title compound (10.4 mg) as a white semi-solid.

MS (ESI) m/z 491 [M+H]$^+$

The following compound were prepared in a similar manner:

4B: N-(4-(4-(3-(tert-Butylcarbamoyl)benzyl)piperazine-1-carbonyl)phenyl)isonicotinamide

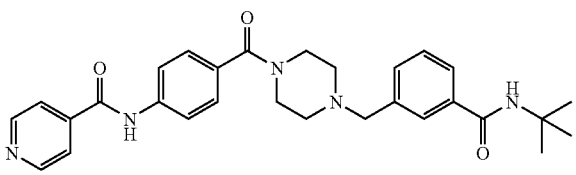

MS (ESI) m/z 498.4 [M−H]$^+$

Example 5

3-((4-(4-Benzamidobenzoyl)piperazin-1-yl)methyl)-N-tert-butylbenzamide

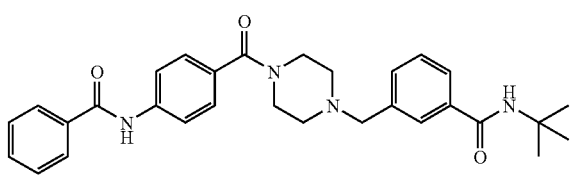

3-((4-(4-Aminobenzoyl)piperazin-1-yl)methyl)-N-tert-butylbenzamide (0.203 mmol, 0.080 g) and triethylamine (1.015 mmol, 0.103 g) were dissolved in dichloromethane (12 mL) and the stirred mixture was cooled to 0° C. Benzoyl chloride (0.305 mmol, 0.043 g) was added and the reaction mixture was allowed to reach room temperature and stir overnight. Water was added to the reaction and the organic layer was then separated, dried (sodium sulfate) and concentrated under vacuum. The residue was purified by silica column chromatography (dichloromethane/methanol (5% to 10%)) and coevaporated with dichloromethane (×3) and diethyl ether (×3) to give the title compound (93 mg). MS (ESI) m/z 499.8 [M+H]$^+$ The following compounds were prepared in a similar manner:

5B; N-(4-(4-(3-(tert-Butylcarbamoyl)benzyl)piperazin-1-carbonyl)phenyl)isoxazole-5-carboxamide

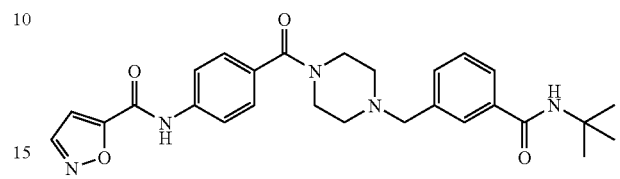

MS (ESI) m/z 490.8 [M+H]$^+$

Example 6

N-tert-Butyl-3-((4-(4-(cyclohexanecarboxamido)-3-fluorobenzoyl)piperazin-1-yl)methyl)-benzamide

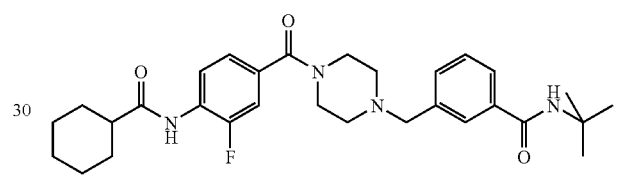

To a stirred solution of 3-((4-(4-amino-3-fluorobenzoyl)piperazin-1-yl)methyl)-N-tert-butylbenzamide (0.121 mmol, 50 mg) and triethylamine (0.485 mmol, 0.068 mL, 49.1 mg) in dichloromethane (1.5 mL) was added cyclohexanecarbonyl chloride (0.133 mmol, 19.55 mg). After 16 hours stirring, the reaction was concentrated under vacuum and purified by acidic reverse phase HPLC to yield the title compound (28 mg).

MS (ESI) m/z 523.5 [M+H]$^+$

The following compound was prepared in a similar manner:

6B: N-tert-Butyl-3-((4-(4-(2-cyclopentylacetamido)-3-fluorobenzoyl)piperazin-1-yl)methyl)benzamide MS (ESI) m/z 523.5 [M+H]$^+$

Example 7

N-tert-Butyl-3-((4-(3-fluoro-4-(3-neopentylureido)benzoyl)piperazin-1-yl)methyl)benzamide

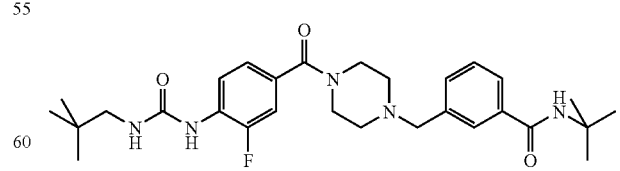

A: N-tert-Butyl-3-(chloromethyl)benzamide 3-(Chloromethyl)benzoyl chloride (20 g, 105.80 mmol) was added to cooled (−30° C.), stirred dichloromethane (60 mL). After 10 minutes stirring, a solution of tert-butylamine (11.1 ml, 105.80 mmol) and N-ethyl-N-Isopropylpropan-2-amine (36.9 mL, 211.60 mmol) in dichloromethane (30 mL) was added dropwise. After complete addition, the reaction was allowed to warm to −15° C. and stir for 90 minutes then was allowed to warm to room temperature. The reaction was concentrated under vacuum and the residue was dissolved in ethyl acetate and washed consecutively with 2M aqueous hydrochloric acid, water (×2) and brine. The organic phase was concentrated under vacuum to give the title compound (19.61 g) as a white solid.

MS (ESI) m/z 226.4 [M+H]$^+$

B: N-tert-Butyl-3-(piperazin-1-ylmethyl)benzamide

N-tert-Butyl-3-(chloromethyl)benzamide (14.71 g, 65.2 mmol), tert-butyl piperazine-1-carboxylate (12.14 g, 65.2 mmol), sodium iodide (1.95 g, 13.0 mmol), triethylamine (27.3 mL, 195.5 mmol) and tetrahydrofuran (125 mL) were stirred together at room temperature for 18 hours. The reaction was then concentrated under vacuum and the residue dissolved in ethyl acetate. The organic mixture was washed consecutively with saturated aqueous sodium hydrogen carbonate solution, water (×2) and brine then concentrated under vacuum. The residue was dissolved in dichloromethane (100 mL), treated with trifluoroacetic acid (25.0 mL, 326.0 mmol) and stirred at 60° C. for 2.5 hours. The reaction was concentrated under vacuum and purified by strong cation exchange (SCX) chromatography, eluting macroporous polystyrene sulfonic acid with 2M ammonia in methanol. The resulting solution was concentrated under vacuum to give the title compound (12.8 g) as a white solid.

MS (ESI) m/z 276.3 [M+H]$^+$

C: 3-((4-(4-Amino-3-fluorobenzoyl)piperazin-1-yl)methyl)-N-tert-butylbenzamide 4-Amino-3-fluorobenzoic acid (500 mg, 3.22 mmol), N-tert-Butyl-3-(piperazin-1-ylmethyl)benzamide (888 mg, 3.22 mmol), N-(3-dimethylaminopropyl)-N'-ethylcarbodiimide hydrochloride (926 mg, 4.83 mmol, EDCl) and triethylamine (984 mg, 898 µl, 6.44 mmol) were combined and stirred in acetonitrile (10 mL) at room temperature overnight (under nitrogen). The reaction was concentrated under reduced pressure. The residue was taken up in dichloromethane (30 mL) and washed with water. The organic phase was dried over sodium sulfate and concentrated under vacuum. The residue was purified by silica chromatography (eluting with a solvent gradient from dichloromethane to 4% methanol/dichloromethane) to give the title compound (355 mg).

MS (ESI) m/z 413.5 [M+H]$^+$

D: N-tert-Butyl-3-((4-(3-fluoro-4-(3-neopentylureido)benzoyl)piperazin-1-yl)methyl)benzamide 3-((4-(4-Amino-3-fluorobenzoyl)piperazin-1-yl)methyl)-N-tert-butylbenzamide (175 mg, 0.424 mmol) and 4-nitrophenylchloroformate (85 mg, 0424 mmol) were stirred in dichloromethane (2 mL) for 30 minutes. Neopentylamine (110 mg, 1.272 mmol) was added and the reaction stirred at room temperature for 2 hours. The reaction was concentrated under vacuum. The resulting residue was purified by acidic reverse phase HPLC to afford the title compound (26 mg).

MS (ESI) m/z 526.5 [M+H]$^+$

The following compounds were prepared in a similar manner:

7B: N-tert-Butyl-3-((4-(3-fluoro-4-(3-cyclobutylureido)benzoyl)piperazin-1-yl)methyl)benzamide; MS (ESI) m/z 510.9 [M+H]$^+$ 7C: N-tert-Butyl-3-((4-(4-(3-(cyclopropylmethyl)ureido)-3-fluorobenzoyl)piperazin-1-yl)methyl)benzamide

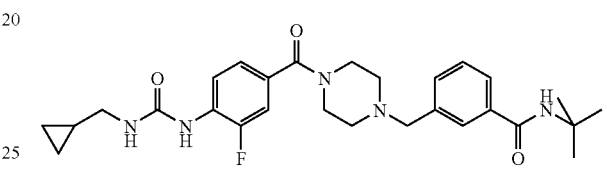

MS (ESI) m/z 510.9 [M+H]$^+$

7D: N-tert-Butyl-3((4-(3-fluoro-4-(3-isobutylureido)benzoyl)piperazin-1-yl)methyl)benzamide

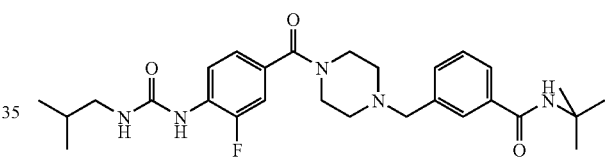

MS (ESI) m/z 512.8 [M+H]$^+$

7E: N-tert-Butyl-3-((4-(3-fluoro-4-(3-isopentylureido)benzoyl)piperazin-1-yl)methyl)benzamide

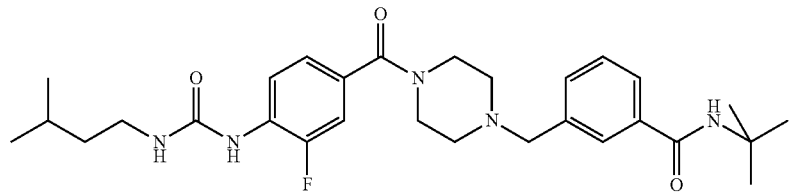

MS (ESI) m/z 526.8 [M+H]$^+$

7F: N-tert-Butyl-3-((4-(4-(3-(cyclobutylmethyl)ureido)-3-fluorobenzoyl)piperazin-1-yl)methyl)benzamide

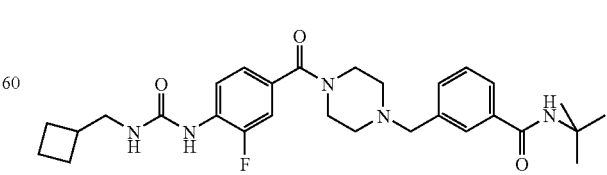

MS (ESI) m/z 524.5 [M+H]$^+$

7G: N-tert-Butyl-3-((4-(4-(3-butylureido)-3-fluorobenzoyl)piperazin-1-yl)methyl)benzamide

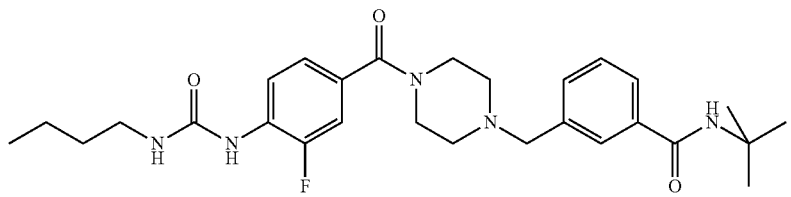

MS (ESI) m/z 512.7 [M+H]+

7H: (S)—N-tert-Butyl-3-((4-(3-fluoro-4-(3-(1,1,1-trifluoropropan-2-yl)ureido)benzoyl)piperazin-1-yl)methyl)benzamide

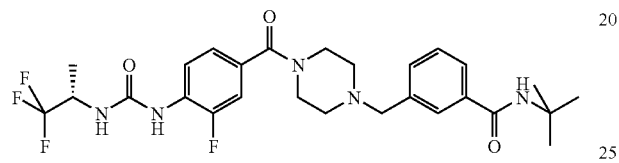

MS (ESI) m/z 552.3 [M+H]+

7I: N-(4-(4-(3-(tert-Butylcarbamoyl)benzyl)piperazine-1-carbonyl)-2-fluorophenyl)-2-isopropylmorpholine-4-carboxamide

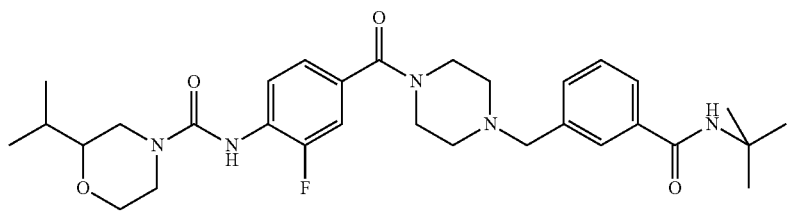

MS (ESI) m/z 568.5 [M+H]+

7J: N-tert-Butyl-3-((4-(3-fluoro-4-(3-(pyridin-2-ylmethyl)ureido)benzoyl)piperazin-1-yl)methyl)benzamide

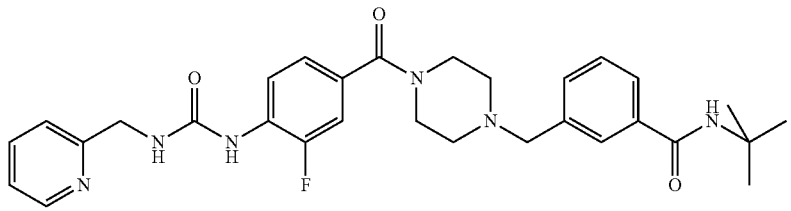

MS (ESI) m/z 547.5 [M+H]+

7K: N-tert-Butyl-3-((4-(4-(3-(3-ethoxypropyl)ureido)-3-fluorobenzoyl)piperazin-1-yl)methyl)benzamide MS (ESI) m/z 542.5 [M+H]+

7L: N-tert-Butyl-3-((4-(3-fluoro-4-(3-(furan-2-ylmethyl)ureido)benzoyl)piperazin-1-yl)methyl)benzamide

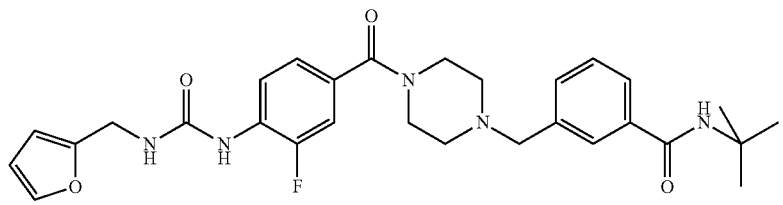

MS (ESI) m/z 538.3 [M+H]+

7M: N-tert-Butyl-3-((4-(3-fluoro-4-(3-phenethylureido)benzoyl)piperazin-1-yl)methyl)benzamide

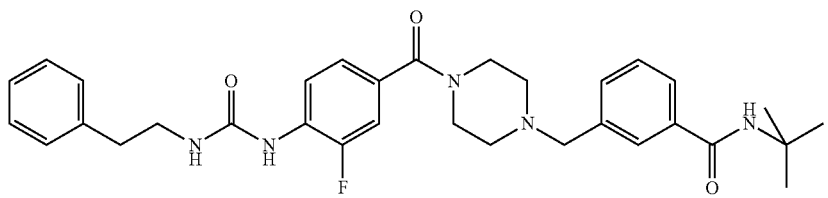

MS (ESI) m/z 560.5 [M+H]+

7N: N-tert-Butyl-3-((4-(3-fluoro-4-(3-(2-(pyridin-2-yl)ethyl)ureido)benzoyl)piperazin-1-yl)methyl)benzamide

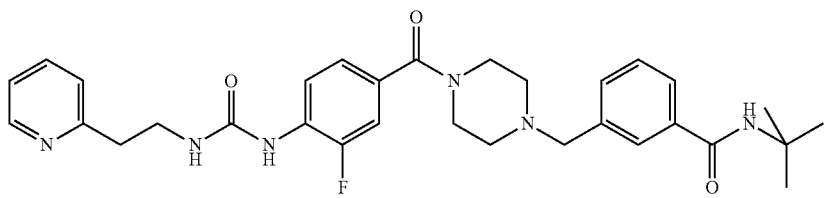

MS (ESI) m/z 561.3 [M+H]+

7O: N-tert-Butyl-3-((4-(3-fluoro-4-(3-(thiophen-2-ylmethyl)ureido)benzoyl)piperazin-1-yl)methyl)benzamide

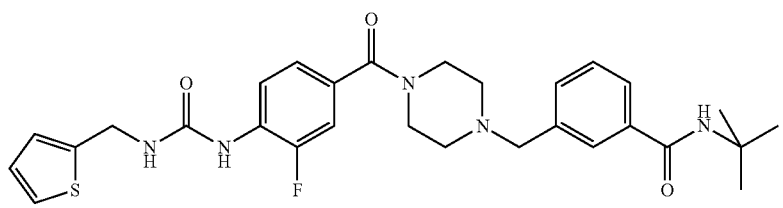

MS (ESI) m/z 552.7 [M+H]+

7P: N-tert-Butyl-3-((4-(3-fluoro-4-(3-(3-methylbut-2-enyl)ureido)benzoyl)piperazin-1-yl)methyl)benzamide

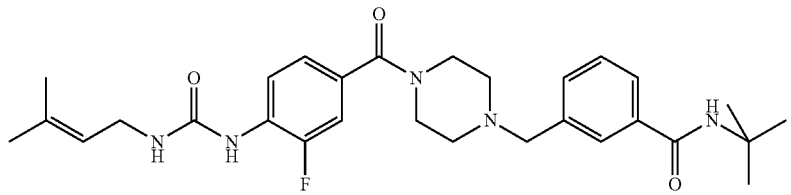

MS (ESI) m/z 524.7 [M+H]+

7Q: N-tert-Butyl-3-((4-(3-fluoro-4-(3-((1,3,5-trimethyl-1H-pyrazol-4-yl)methyl)ureido)benzoyl)piperazin-1-yl)methyl)benzamide

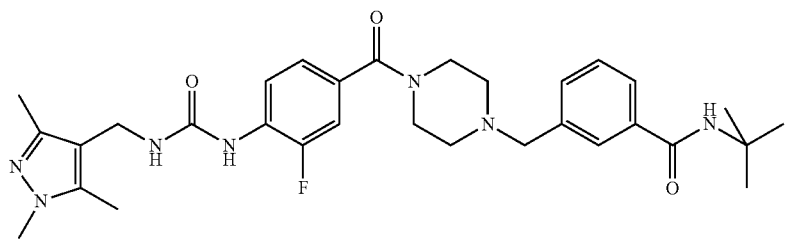

MS (ESI) m/z 578.3 [M+H]+

7R: N-tert-Butyl-3-((4-(3-fluoro-4-(3-(2-(pyrrolidin-1-yl)ethyl)ureido)benzoyl)piperazin-1-yl)methyl)benzamide

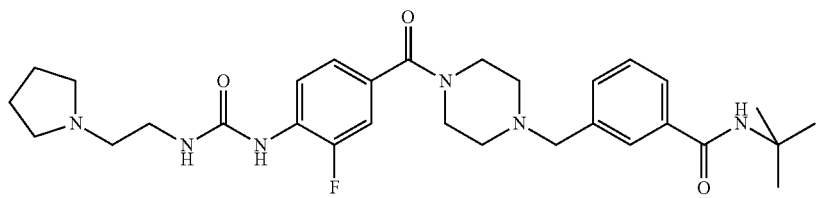

MS (ESI) m/z 553.3 [M+H]+

7S: N-tert-Butyl-3-((4-(3-fluoro-4-(3-((1-hydroxycyclopropyl)methyl)ureido)benzoyl)piperazin-1-yl)methyl)benzamide

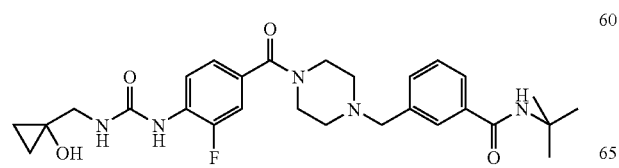

MS (ESI) m/z 526.3 [M+H]+

7T: (R)—N-tert-Butyl-3-((4-(3-fluoro-4-(3-(1-hydroxy-3-phenylpropan-2-yl)ureido)benzoyl)piperazin-1-yl)methyl)benzamide

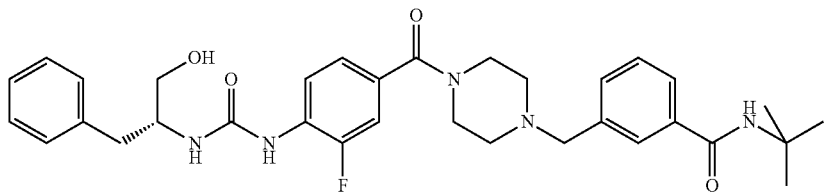

MS (ESI) m/z 590.7 [M+H]⁺

7U: N-tert-Butyl-3-((4-(3-fluoro-4-(3-(2-oxopyrrolidin-1-yl)propyl)ureido)benzoyl)piperazin-1-yl)methyl)benzamide

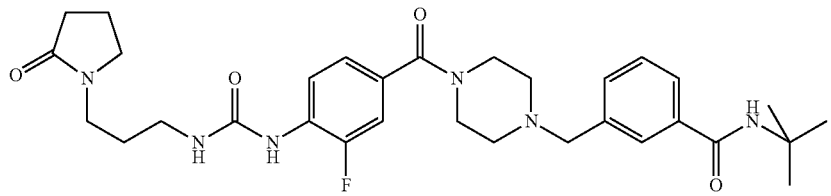

MS (ESI) m/z 581.3 [M+H]⁺

7V: N-tert-Butyl-3-((4-(3-fluoro-4-(3-(3-isopropoxyproply)ureido)benzoyl)piperazin-1-yl)methyl)benzamide

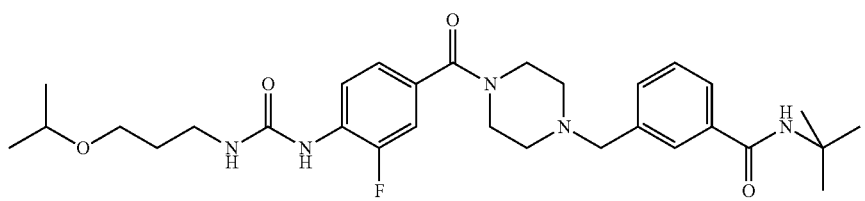

MS (ESI) m/z 556.3 [M+H]⁺

7W: N-tert-Butyl-3-((4-(3-fluoro-4-(3-(2-(1-methylpyrrolidin-2-yl)ethyl)ureido)benzoyl)-piperazin-1-yl)methyl)benzamide

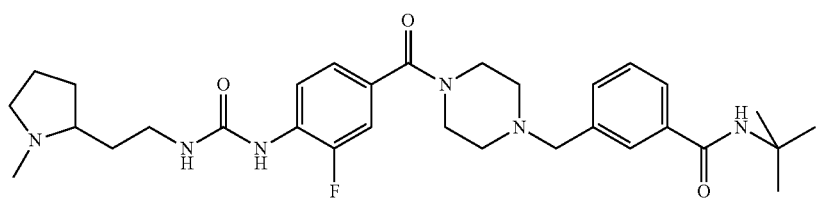

MS (ESI) m/z 567.7 [M+H]⁺

7X: 3-((4-(4-(3-(2-acetamidoethyl)ureido)-3-fluorobenzoyl)piperazin-1-yl)methyl)-N-tert-butylbenzamide

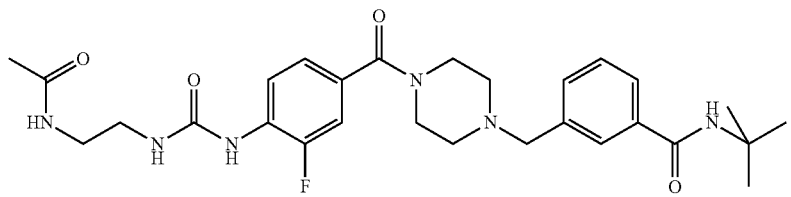

MS (ESI) m/z 541.5 [M+H]+

7Y: N-tert-Butyl-3-((4-(4-(3-(1-(dimethylamino)-2-methyl-propan-2-yl)ureido)-3-fluorobenzoyl)piperazin-1-yl)methyl)benzamide

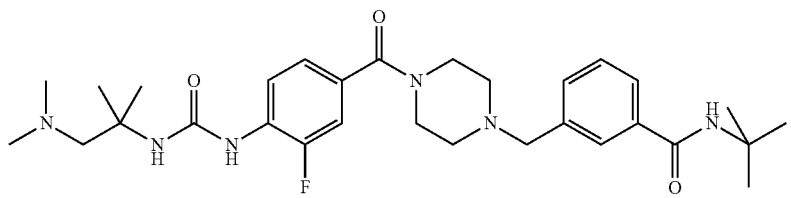

MS (ESI) m/z 555.5 [M+H]+

7Z: N-tert-Butyl-3-((4-(4-(3-(2,6-difluorobenzyl)ureido)-3-fluorobenzoyl)piperazin-1-yl)methyl)benzamide

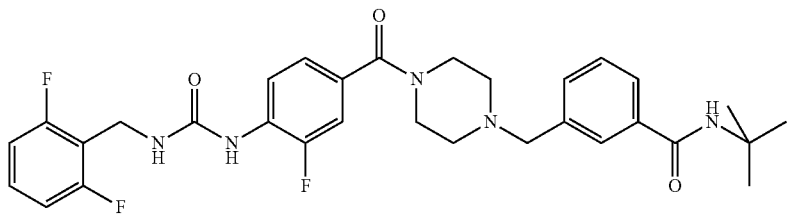

MS (ESI) m/z 582.3 [M+H]+

7AA: 3-((4-(4-(4-(3-(2-(benzo[d][1,3]dioxol-5-yl)ethyl)ureido)-3-fluorobenzoyl)piperazin-1-yl)methyl)-N-tert-butylbenzamide

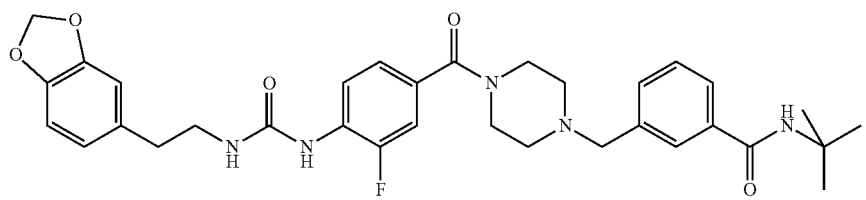

MS (ESI) m/z 604.7 [M+H]+

7AB: N-tert-Butyl-3-((4-(3-fluoro-4-(3-((1-hydroxycyclohexyl)methyl)ureido)benzoyl)piperazin-1-yl) methyl)benzamide

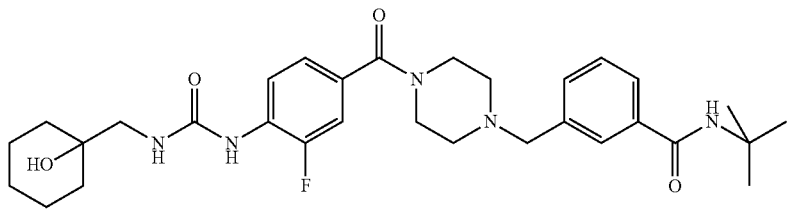

MS (ESI) m/z 568.5 [M+H]+

7AC: N-tert-Butyl-3-((4-(3-fluoro-4-(3-((1S,2S)-2-hydroxycyclopentyl)ureido)benzoyl)-piperazin-1-yl)methyl)benzamide

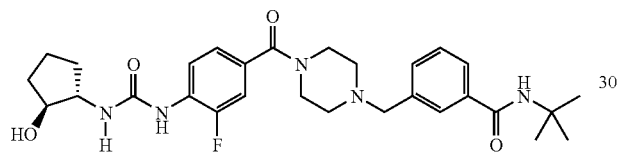

MS (ESI) m/z 540.7 [M+H]+

7AD: N-tert-Butyl-3-((4-(3-fluoro-4-(3-(2-(2-oxoimidazolidin-1-yl)ethyl)ureido)benzoyl)-piperazin-1-yl)methyl)benzamide

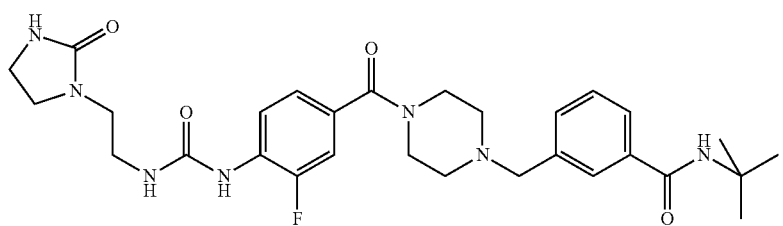

MS (ESI) m/z 568.5 [M+H]+

7AE: N-tert-Butyl-3-((4-(3-fluoro-4-(3-(3,3,3-trifluoro-2-hydroxypropyl)ureido)benzoyl)-piperazin-1-yl)methyl)benzamide

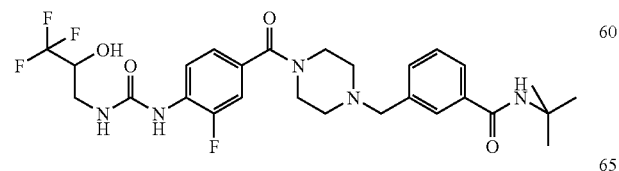

MS (ESI) m/z 568.5 [M+H]+

7AF: R)—N-tert-Butyl-3-((4-(3-fluoro-4-(3-((tetrahydrofuran-2-yl)methyl)ureido)benzoyl)piperazin-1-yl)methyl)benzamide

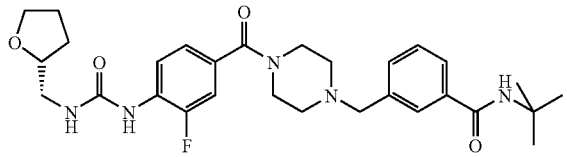

MS (ESI) m/z 540.5 [M+H]$^+$

7AG: N-tert-Butyl-3-((4-(3-fluoro-4-(3-(thiazol-2-ylmethyl)ureido)benzoyl)piperazin-1-yl)methyl)benzamide

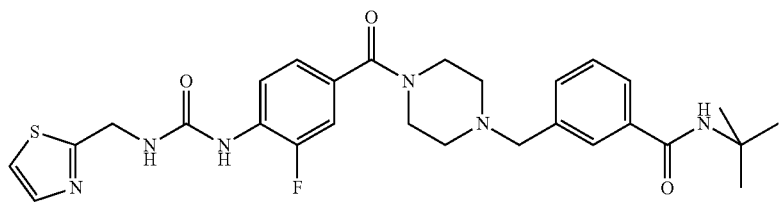

MS (ESI) m/z 553.3 [M+H]$^+$

7AH: N-tert-Butyl-3-((4-(4-(3-((1-cyanocyclopropyl)methyl)ureido)-3-fluorobenzoyl)piperazin-1-yl)methyl)benzamide

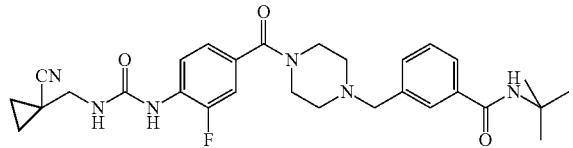

MS (ESI) m/z 535.3 [M+H]$^+$

The 1-(aminomethyl)cyclopropanecarbonitrile, needed in the synthesis was prepared as follows:

Step 1: To a mixture of ethyl 1-cyanocyclopropanecarboxylate (35.9 mmol, 5 g), dimethoxyethane (100 mL) and methanol (10 mL) was added sodium borohydride (287 mmol, 10.87 g) slowly and the mixture stirred at room temperature for 18 hours. The solution was diluted with saturated sodium hydrogen carbonate slowly and then extracted with 10% methanol/dichloromethane (×3). The organic layers were combined, dried over sodium sulphate and concentrated under vacuum to give the intermediate 1-(hydroxymethyl)cyclopropanecarbonitrile (2.36 g).

1H NMR (CDCl$_3$, 400 MHz): δ 0.99 (2H, m), 1.28 (2H, m), 2.5 (1H, br s), 3.62 (2H, s)

Step 2: A stirred mixture of 1-(hydroxymethyl)cyclopropanecarbonitrile (24.30 mmol, 2.36 g) in dichloromethane (30 mL) was treated with triethylamine (48.6 mmol, 6.83 mL, 4.92 g) and portionwise with methanesulfonyl chloride (31.6 mmol, 2.445 mL, 3.62 g) keeping the reaction mixture at 0° C. The solution was allowed to stir for 1 hour then diluted with saturated sodium hydrogencarbonate and extracted with 10% methanol/dichloromethane (×3). The organic layers were combined and concentrated under reduced pressure to give the intermediate (1-cyanocyclopropyl)methyl methanesulfonate (3.77 g).

1H NMR (CDCL$_3$, 400 MHz): δ 1.18 (2H, m), 1.46 (2H, m), 3.14 (3H, s), 4.18 (2H, s)

Step 3: A stirred mixture of (1-cyanocyclopropyl)methyl methanesulfonate (21.52 mmol, 3.77 g) and sodium azide (43.0 mmol, 2.80 g) in N,N-diemethyl formamide (40 mL) was heated to 120° C. for ~18 hours. The mixture was allowed to cool and was diluted with water and ethyl acetate. The organic layer was separated, dried over sodium sulphate and concentrated under reduced pressure to give an oil. This oil was taken up in ether and washed with water, dried and concentrated under reduced pressure to give the intermediate 1-(azidomethyl)cyclopropanecarbonitrile (1.8 g) as an oil.

1H NMR (CDCl$_3$, 400 MHz); δ 1.02 (2H, m), 1.36 (2H, m), 3.38 (2H, s)

Step 4: To a solution of 1-(azidomethyl)cyclopropanecarbonitrile (14.74 mmol, 1.8 g) in methanol (20 mL) was added 10% palladium on carbon (14.74 mmol, 200 mg) containing water (200 μL). The mixture was stirred under hydrogen at 3 bar overnight at room temperature. The catalyst was removed by filtration and the filtrate concentrated under reduced pressure to give the title compound (1,3 g).

1H NMR (CDCl$_3$, 400 MHz): δ 0.87 (2H, m), 1.23 (2H, m), 2.76 (2H, s)

7AI: N-tert-Butyl-3-((4-(4-(3-(2-cyclopropylethyl)ureido)-3-fluorobenzoyl)piperazin-1-yl)methyl)benzamide

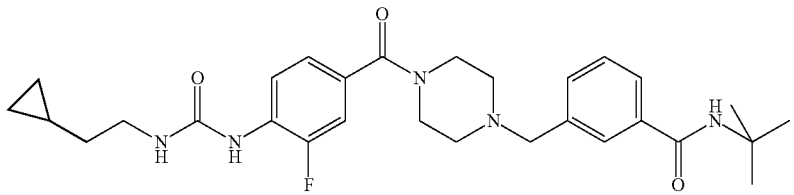

MS (ESI) m/z 524.7 [M+H]$^+$

7AJ: 3-((4-(4-(3-(2-Amino-2-methylpropyl)ureido)-3-fluorobenzoyl)piperazin-1-yl)methyl)-N-tert-butylbenzamide

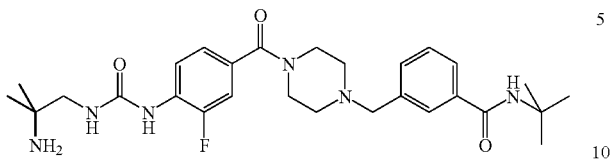

MS (ESI) m/z 527.5 [M+H]+

7AK: N-tert-Butyl-3-((4-(4-(3-(3,3-difluorocyclobutyl)ureido)-3-fluorobenzoyl)piperazin-1-yl)methyl)benzamide

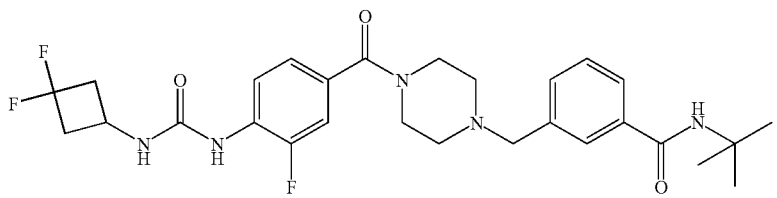

MS (ESI) m/z 546.5 [M+H]+

7AL: N-tert-Butyl-3-(4-{4-[3-(1,1-dioxo-tetrahydro-1☐6-thiophen-3-yl)-ureido]-3-fluoro-benzoyl}-piperazin-1-ylmethyl)-benzamide

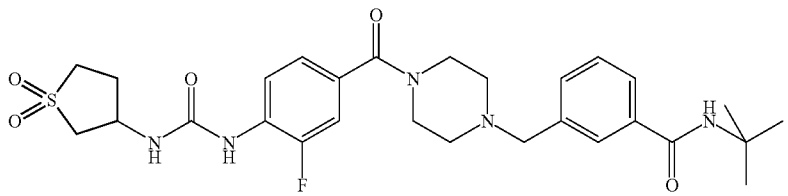

MS (ESI) m/z 574.4 [M+H]+

Example 8

N-tert-Butyl-3-((4-(3-fluoro-4-(3-(2-fluorophenyl)ureido)benzoyl)piperazin-1-yl)methyl)benzamide

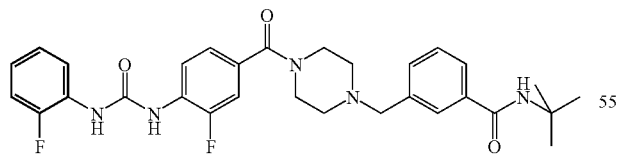

3-((4-(4-Amino-3-fluorobenzoyl)piperazin-1-yl)methyl)-N-tert-butylbenzamide (100 mg, 0.242 mmol) and 2-fluorophenylisocyanate (37 mg, 0.267 mmol) were combined and heated in dichloromethane at 100° C. in the microwave for 10 minutes. The solvent was removed under reduced pressure and the residue purified by acidic reverse phase HPLC to afford the title compound (12 mg).

MS (ESI) m/z 550.5 [M+H]+

The following compounds were prepared in a similar manner:

8B: N-tert-Butyl-3-((4-(3-fluoro-4-(3-pyridin-3-ylureido)benzoyl)piperazin-1-yl)methyl)benzamide

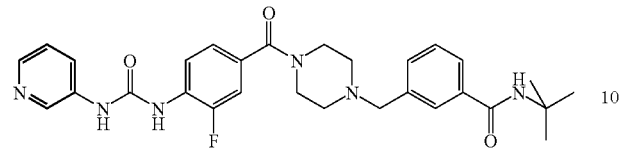

MS (ESI) m/z 533.3 [M+H]+

8C: N-tert-Butyl-3-((4-(3-fluoro-4-(3-(5-methyl-2-(trifluoromethyl)furan-3-yl)ureido)benzoyl)piperazin-1-yl)methyl)benzamide

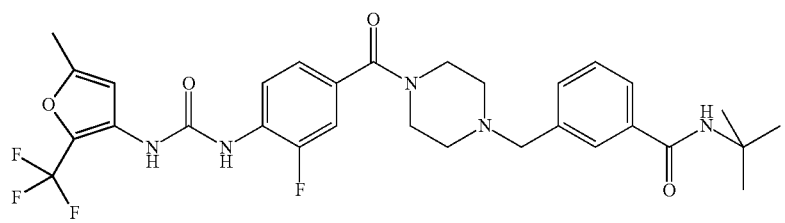

MS (ESI) m/z 604.5 [M+H]+

Example 9

N-tert-Butyl-3-((4-(4-(3-(5-tert-butylisoxazol-3-yl)ureido)-3-fluorobenzoyl)piperazin-1-yl)methyl)benzamide 2,2,2-trifluoroacetate

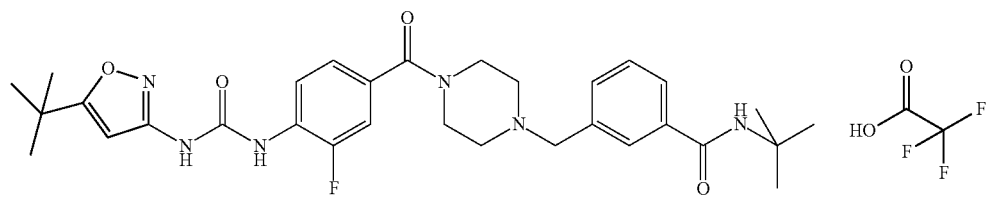

3-((4-(4-Amino-3-fluorobenzoyl)piperazin-1-yl)methyl)-N-tert-butylbenzamide (100 mg, 0.242 mmol), dichloromethane and 4-nitrophenylchloroformate (49 mg, 0.242 mmol) were combined and stirred at room temperature for 30 minutes, 5-tert-Butylisoxazol-3-amine (101 mg, 0.726 mmol) and triethylamine (73 mg, 0.726 mmol) were added and the reaction heated for 10 minutes in the microwave at 120° C. The reaction was concentrated under reduced pressure and the resulting residue purified by acidic reverse phase HPLC to afford the title compound (40 mg).

MS (ESI) m/z 579.5 [M+H]+

The following compound was prepared in a similar manner:

9B: N-tert-Butyl-3-((4-(3-fluoro-4-(3-(4-methylthiazol-2-yl)ureido)benzoyl)piperazin-1-yl)methyl)benzamide

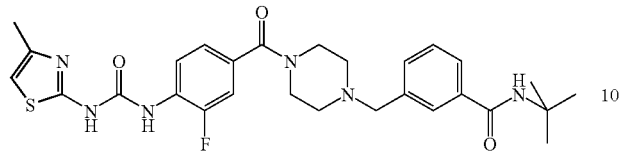

MS (ESI) m/z 553.2 [M+H]⁺

Example 10

N-tert-Butyl-3-((4-(3-fluoro-4-(3-(5-(trifluoromethyl)pyridin-2-yl)ureido)benzoyl)piperazin-1-yl)methyl)benzamide

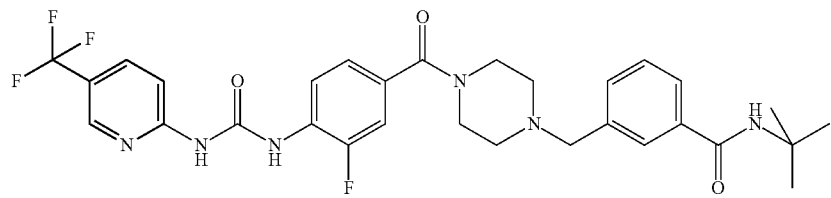

5-(Trifluoromethyl)pyridin-2-amine (0.485 mmol, 0.079 g) and N-ethyl-N-isopropylpropan-2-amine (0.727 mmol, 0.120 mL, 0.094 g) were added to a stirred solution of bis(trichloromethyl) carbonate (0.160 mmol, 0.047 g) in dichloromethane (10 mL). The reaction was stirred for 3 hours at room temperature. 3-((4-(4-Amino-3-fluorobenzoyl)piperazin-1-yl)methyl)-N-tert-butylbenzamide (0.242 mmol, 0.1 g) was added and the reaction stirred for 30 minutes. The reaction was heated in the microwave at 120° C. for 10 minutes. The reaction was concentrated under vacuum and purified by acidic reverse phase HPLC to afford the title compound (50 mg).

MS (ESI) m/z 601.3 [M+H]⁺

The following, compounds were prepared in a similar manner:

10B: N-tert-Butyl-3-((4-(3-(5-tert-butyl-1,3,4-thiadiazol-2-yl)ureido)-3-fluorobenzoyl)piperazin-1-yl)methyl)benzamide

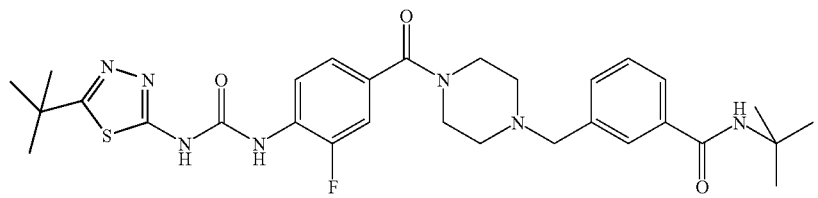

MS (ESI) m/z 596.5 [M+H]⁺

10C: N-tert-Butyl-3-((4-(3-fluoro-4-(3-thiazol-2-ylureido)benzoyl)piperazin-1-yl)methyl)benzamide

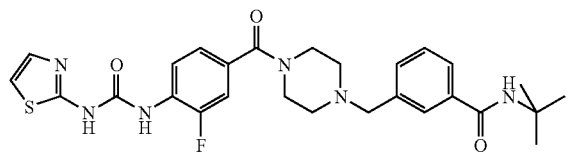

MS (ESI) m/z 539.5 [M+H]+

Example 11

N-tert-Butyl-3-((4-(4-(3-(cyclopropylmethyl)ureido)-3,5-difluorobenzoyl)piperazin-1-yl)methyl)benzamide

A: 3-((4-(4-Amino-3,5-difluorobenzoyl)piperazin-1-yl)methyl)-N-tert-butylbenzamide

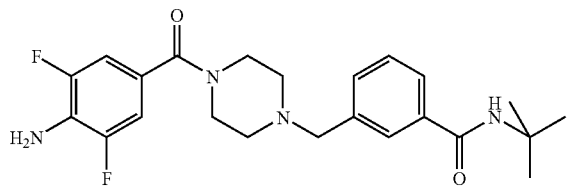

To a stirred solution of 4-ammo-3,5-difluorobenzoic acid (1 g, 5.78 mmoles), N-tert-butyl-3-(piperazin-1-ylmethyl)benzamide (1.59 g, 5.78 mmoles) and triethylamine (4 mL) in dichloromethane (30 mL) was added 1-propanephosphonic acid cyclic anhydride (8 mL, 50% solution in ethyl acetate). After 2 hours stirring, the reaction mixture was diluted with ethyl acetate and washed with sodium carbonate (aqueous) (3×), dried (magnesium sulfate) and concentrated under reduced pressure to give the title compound (2.24 g) as an off-white foam.
MS (ESI) m/z 431.9 [M+H]+

B: N-tert-Butyl-3-((4-(4-(3-cyclopropylmethyl)ureido)-3,5-difluorobenzoyl)piperazin-1-yl)methyl)benzamide To a stirred solution of bis(trichloromethyl) carbonate (0.353 mmol, 105 mg) in dichloromethane (10 mL) was added a solution of 3-((4-(4-amino-3,5-difluorobenzoyl)piperazin-1-yl)methyl)-N-tert-butylbenzamide (0.929 mmol. 400 mg) and N-ethyl-N-iosopropylpropan-2-amine (0.3 mL) in dichloromethane (10 mL) (dropwise). After 2 hours stirring, a solution of cyclopropylmethylamine (1.022 mmol, 0.089 mL, 72.7 mg) and N-ethyl-N-isopropylpropan-2-amine (0.222 mL) in dichloromethane (10 mL) was added. The reaction mixture was stirred for 24 hours. Chromatography on silica (eluting with dichloromethane then dichloromethane/methanol (1% to 5%)) gave the title compound (220 mg). MS (ESI) m/z 528.3 [M+H]+

Example 12

N-tert-Butyl-3-((4-(3-chloro-4-(3-cyclobutylureido)benzoyl)piperazin-1-yl)methyl)benzamide

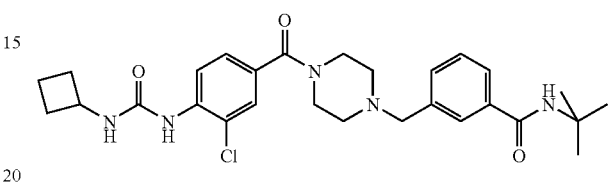

A: 3-((4-(4-Amino-3-chlorobenzoyl)piperazin-1-yl)methyl)-N-tert-butylbenzamide

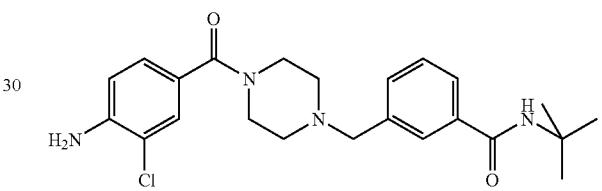

4-Amino-3-chlorobenzoic acid (1.04 g, 6.06 mmol), N-tert-butyl-3-(piperazin-1-ylmethyl)-benzamide (888 mg, 3.22 mmol), N-(3-dimethylaminopropyl)-N'-ethylcarbodiimide hydro-chloride (1.742 g, 9.09 mmol) and triethylamine (1.23 g, 1.69 mL, 12.12 mmol) were combined and stirred in acetonitrile (20 mL) at room temperature overnight (under nitrogen). The reaction was concentrated under reduced pressure and the residue was diluted with dichloromethane (30 mL) and water. The organic layer was separated, dried over sodium sulfate and concentrated under vacuum. The resulting residue was purified by silica chromatography (eluting with a solvent gradient from dichloromethane to 4% methanol/dichloromethane) to afford the title compound (1.3 g).
MS (ESI) m/z 429.7 [M+H]+

B: N-tert-Butyl-3-((4-(3-chloro-4-(3-cyclobutylureido)benzoyl)piperazin-1-yl)methyl)benzamide 3-((4-(4-Amino-3-chlorobenzoyl)piperazin-1-yl)methyl)-N-tert-butylbenzamide (200 mg, 0.466 mmol) and 4-nitrophenylchloroformate (94 mg, 0.466 mmol) were heated to reflux in dichloromethane (10 ml) for 2 hours. Cyclobutylamine (99 mg, 1.398 mmol) was added and the reaction stirred overnight. The reaction mixture was washed with water, dried over sodium sulfate and concentrated under vacuum. The resulting residue was purified by acidic reverse phase HPLC to afford the title compound (20 mg).
MS (ESI) m/z 527.3 [M+H]+
The following compounds were prepared in a similar way:
12B: N-tert-Butyl-3-((4-(3-chloro-4-(3-(cyclopropylmethyl)ureido)benzoyl)piperazin-1-yl)methyl)benzamide
MS (ESI) m/z 526.5 [M+H]+

12C: N-tert-Butyl-3-((4-(3-chloro-4-(3-neopentylureido)benzoyl)piperazin-1-yl)methyl)benzamide
MS (ESI) m/z 542.8 [M+H]$^+$ 12D: N-tert-Butyl-3-((4-(3-chloro-4-(3-isobutylureido)benzoyl)piperazin-1-yl)methyl)benzamide
MS (ESI) m/z 528.5 [M+H]$^+$ 12E: 1-(3-(tert-Butylcarbamoyl)benzyl)-4-(3-chloro-4-(3-(cyclobutylmethyl)ureido)benzoyl)piperazine-1-oxide
MS (ESI) m/z 540.5 [M+H]$^+$ 12F: N-tert-Butyl-3-((4-(4-(3-butylureido)-3-chlorobenzoyl)piperazin-1-yl)methyl)benzamide
MS (ESI) m/z 528.2 [M+H]$^+$ 12G: N-tert-Butyl-3-((4-(3-chloro-4-(3-isopentylureido)benzoyl)piperazin-1-yl)methyl)benzamide
MS (ESI) m/z 542.5 [M+H]$^+$ Example 13

N-tert-butyl-3-((4-(2-methyl-4-(3-neopentylureido)benzoyl)piperazin-1-yl)methyl)benzamide

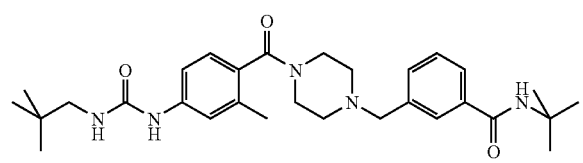

A: 3-((4-(4-Amino-2-methylbenzoyl)piperazin-1-yl)methyl)-N-tert-butylbenzamide

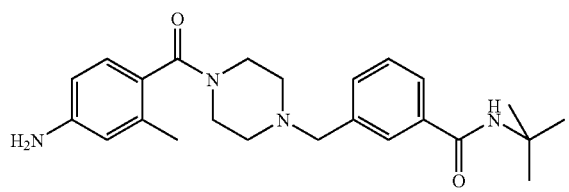

4-Amino-2-methylbenzoic acid (1 g, 6.62 mmol) and triethylamine (4 mL) were stirred in dichloromethane. 1-Propanephosphonic acid cyclic anhydride (8 mL 50% solution in ethyl acetate) was added dropwise and the reaction stirred at room temperature for 2 hours. The reaction was concentrated under reduced pressure and the residue taken up in ethyl acetate. The organic solution was washed with saturated sodium hydrogen carbonate solution, dried over sodium sulfate and concentrated under vacuum to afford the title compound (902 mg).
MS (ESI) m/z 409.7 [M+H]$^+$ B: N-tert-butyl-3-((4-(2-methyl-4-(3-neopentylureido)benzoyl)piperazin-1-yl)methyl)benzamide 3-((4-(4-Amino-2-methylbenzoyl)piperazin-1-yl)methyl)-N-tert-butylbenzamide (100 mg, 0.24 mmol) and 4-nitrophenylchloroformate (49 mg, 0.24 mmol) were stirred in dichloromethane (2 mL) for 30 minutes. Neopentylamine (64 mg, 0.73 mmol) was added and the reaction stirred at room temperature for 2 hours. The reaction was concentrated under vacuum. The resulting residue was purified by acidic reverse phase HPLC to afford the title compound (31 mg). MS (ESI) m/z 522.7 [M+H]$^+$ Example 14

N-tert-Butyl-3-((4-(4-(3-(cyclopropylmethyl)ureido)-2-fluorobenzoyl)piperazin-1-yl)methyl)benzamide

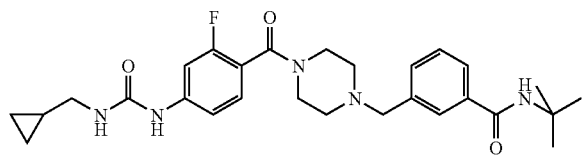

A: N-tert-Butyl-3-((4-(2-fluoro-4-nitrobenzoyl)piperazin-1-yl)methyl)benzamide

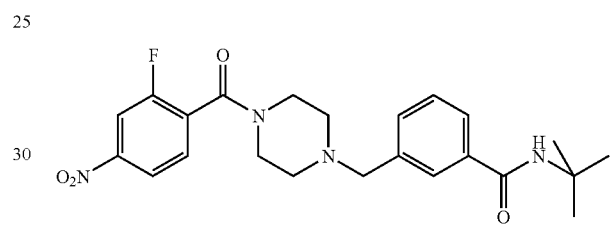

2-Fluoro-4-nitrobenzoic acid (5 g, 27.01 mmol) was dissolved in acetonitrile (150 mL) and triethylamine (7.53 mL, 54.02 mmol). N-(3-dimethylaminopropyl)-N'-ethylcarbodiimide hydrochloride (7.8 g, 40.52 mmol) was added, followed by N-tert-butyl-3(piperazin-1-ylmethyl)benzamide (7.44 g, 27.01 mmol). The reaction was stirred at room temperature for 18 hours and concentrated under vacuum. The residue was dissolved in ethyl acetate, filtered through dicalite, washed consecutively with water (×2) and brine and concentrated under vacuum. The product was purified by strong cation exchange chromatography, eluting macroporous polystyrene sulfonic acid with 2M ammonia in methanol. The resulting solution was concentrated under vacuum to afford the title compound as a pale yellow oil (2.6 g). MS (ESI) m/z 443.7 [M+H]$^+$ B: 3-((4-(4-Amino-2-fluorobenzoyl)piperazin-1-yl)methyl)-N-tert-butylbenzamide

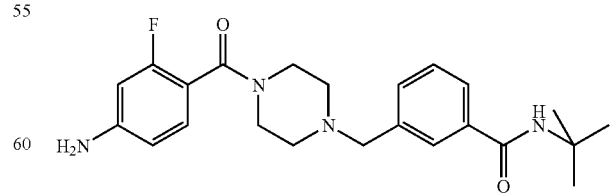

To a suspension of iron (O) powder (3.3 g, 58.76 mmol) and N-tert butyl-3-((4-(2-fluoro-4-nitrobenzoyl)piperazin-1-yl)methyl)benzamide (2.6 g, 5.88 mmol) in propan-2-ol (75 mL) was added 1M aqueous hydrochloric acid (8.8 mL, 8.1 mmol). The reaction was stirred at room temperature for 2.5 hours, filtered through dicalite and concentrated under vacuum. The residue was dissolved in methanol and purified by strong cation exchange chromatography, eluting macroporous polystyrene sulfonic acid with 2M ammonia in methanol. The resulting solution was concentrated under vacuum to afford the title compound as a viscous orange oil (2.2 g).

MS (ESI) m/z 413.5 [M+H]$^+$

C: N-tert-Butyl-3-((4-(4-(3-(cyclopropylmethyl)ureido)-2-fluorobenzoyl)piperazin-1-yl)methyl)benzamide 4-Nitrophenyl chloroformate (59 mg, 0.29 mmol) was added to a solution of 3-((4-(4-amino-2-fluorobenzoyl)piperazin-1-yl)methyl)-N-tertbutylbenzamide (100 mg, 0.24 mmol) in acetonitrile (10 mL). After stirring at room temperature for 1 hour, cyclopropylmethylamine (126 µL, 1.21 mmol) was added. After 2 hours stirring, the reaction was purified by strong cation exchange chromatography, eluting macroporous polystyrene sulfonic acid with 2N ammonia in methanol. The resulting solution was concentrated under vacuum and purified by basic reverse phase HPLC to afford the title compound as a white solid (10 mg).

MS (ESI) m/z 510.9 [M+H]$^+$

Example 15

N-tert-Butyl-3-((4-(2-chloro-4-(3-isobutylureido)benzoyl)piperazin-1-yl)methyl)benzamide

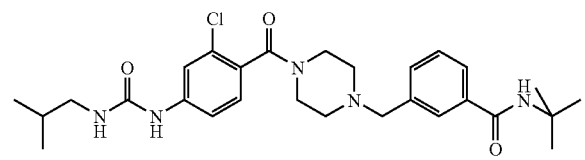

A: N-tert-Butyl-3-((4-(2-chloro-4-nitrobenzoyl)piperazin-1-yl)methyl)benzamide

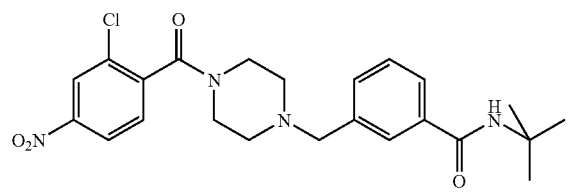

1-Propanephosphonic acid cyclic anhydride (3.16 g, 92 mmol, 2.95 mL) was added dropwise to a solution of 2-chloro-4-nitrobenzoic acid (1 g, 4.9 mmol), N-tert-butyl-3-(piperazin-1-ylmethyl)benzamide (1.4169 g, 5.1 mmol) and triethylamine (1.4979 g, 14.7 mmol, 2 mL) in dichloromethane. The reaction was concentrated under reduced pressure and the residue was taken up in ethyl acetate, washed with water, sodium hydrogen carbonate and brine. The organic phase was concentrated under vacuum to afford the title compound (2.06 g).

MS (ESI) m/z 459.7 [M+H]$^+$

B: 3-((4(4-Amino-2-chlorobenzoyl)piperazin-1-yl)methyl)-N-tert-butylbenzamide

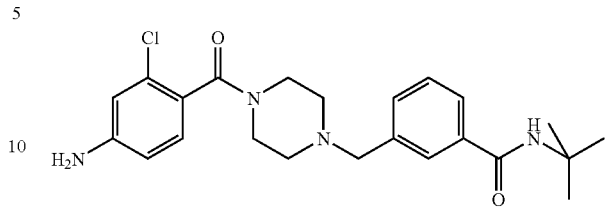

N-tert-Butyl-3-((4-(2-chloro-4-nitrobenzoyl)piperazin-1-yl)methyl)benzamide (1.9483 g, 4.2 mmol) was added to a suspension of reduced iron powder (2.3623 g, 42 mmol) and 1M hydrochloric acid (6 mL) in isopropanol. The reaction was stirred at room temperature for 2 hours. The reaction was concentrated under reduced pressure and the remaining residue was taken up in dichloromethane and washed with water. The organic phase was dried over magnesium sulphate and concentrated under vacuum to afford the title compound (1.57 g).

MS (ESI) m/z 429.5 [M+H]$^+$

C: N-tert-Butyl-3-((4-(2-chloro-4-(3-isobutylureido)benzoyl)piperazin-1-yl)methyl)benzamide 3-((4-(4-Amino-2-chlorobenzoyl)piperazin-1-yl)methyl)-N-tert-butylbenzamide (250 mg, 0.625 mmol) and 4-nitrophenol chloroformate (126 mg, 0.625 mmol) were combined and stirred in dichloromethane for 1 hour. Isobutylamine (87.8 mg, 1.2 mol, 0.12 mL) was added and the reaction was stirred for 30 minutes. The reaction mixture was diluted with water and flushed through a hydrophobic frit. The reaction was concentrated under reduced pressure to give a residue, which was purified by silica chromatography (eluting with a solvent gradient from dichloromethane to 4% methanol/dichloromethane) to afford the title compound (178.1 mg).

MS (ESI) m/z 528.3 [M+H]$^+$

Example 16

N-tert-Butyl-3-((4-(4-(3-cyclobutylureido)-2,5-difluorobenzoyl)piperazin-1-yl)methyl)benzamide

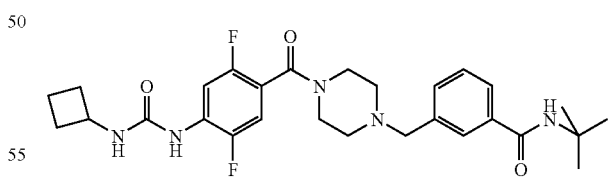

A: 4-Amino-2,5-difluorobenzoic Acid 2,5-Difluoro-4-nitrobenzoic acid (1 g, 4.9 mmol) was dissolved in ethanol. 10% Palladium on carbon (500 mg) was added and reaction stirred under a hydrogen balloon overnight. The catalyst was filtered off and the filtrate was concentrated under reduced pressure to afford the title compound (0.79 g).

MS (ESI) m/z 172.3 [M–H]$^+$

B: 19: 3-((4-(4-Amino-2,5-difluorobenzoyl)piperazin-1-yl)methyl)-N-tert-butylbenzamide A: 3-((4-(4-amino-5-chloro-2-methoxybenzoyl)piperazin-1-yl)methyl)-N-tert-butylbenzamide

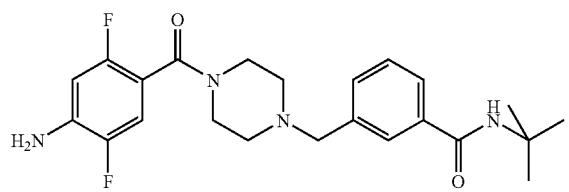

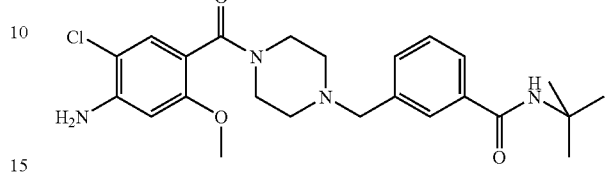

1-Propanephosphonic acid cyclic anhydride (2.91 g, 9.2 mmol, 2.73 mL) was added dropwise to a solution of 4-amino-2,5-difluorobenzoic acid (792.9 mg, 4.6 mmol), N-tert-butyl-3-(piperazin-1-ylmethyl)benzamide (1.3878 g, 5 mmol) and triethylamine (1.39 g, 13.9 mmol, 1.91 mL) in dichloromethane. The reaction mixture was stirred at room temperature for 1 hour. The reaction was concentrated under reduced pressure and the residue was taken up with ethyl acetate, washed with water, sodium hydrogen carbonate and brine. The organic phase was concentrated under vacuum to afford the title compound (1.52 g). MS (ESI) m/z 431.9 [M+H]$^+$ 1-Propanephosphonic acid cyclic anhydride (6.31 g, 9.92 mmol, 5.91 ml) was added dropwise to a solution of 4-amino-5-chloro-2-methoxybenzoic acid (1 g, 5 mmol), N-tert-butyl-3-(piperazin-1-ylmethyl)benzamide (1.5150 g, 5,5 mol) and triethylamine (1.508 g, 14.88 mmol, 2.068 mL) in dichloromethane. The reaction was stirred at room temperature for 1 hour. The reaction was concentrated under reduced pressure and the residue was taken up with ethyl acetate, washed with water, sodium hydrogen carbonate and brine. The organic phase was concentrated under vacuum to afford the title compound (1.71 g). MS (ESI) m/z 459.7 [M+H]$^+$ C: N-tert-Butyl-3-((4-(4-(3-cyclobutylureido)-2,5-difluorobenzoyl)piperazin-1-yl)methyl)-benzamide 3-((4-(4-Amino-2,5-difluorobenzoyl)piperazin-1-yl)methyl)-N-tert-butylbenzamide (1 g, 0.023 mol) and 4-nitrophenol chloroformate (0.4636 g, 0.0023 mol) were combined and stirred in dichloromethane for 1 hour at room temperature. Cyclobutylamine (0.8969 g, 0.0017 mol, 0.108 mL) was added and the reaction was stirred for 30 minutes. The reaction mixture was diluted with water and flushed through a hydrophobic frit. The organic phase was concentrated under vacuum and purified by acidic reverse phase HPLC to afford the title compound (21 mg).

MS (ESI) m/z 528.3 [M+H]$^+$

B: N-tert-Butyl-3-((4-(5-chloro-4-(3-isobutylureido)-2-methoxybenzoyl)piperazin-1-yl)methyl)-benzamide 3-((4-(4-Amino-5-chloro-2-methoxybenzoyl)piperazin-1-yl)methyl)-N-tert-butylbenzamide (1.712 g, 0.0037 mol) and 4-nitrophenol chloroformate (0.7518 g, 0.0037 mol) were combined and stirred at room temperature in dichloromethane for 1 hour. Isobutylamine (0.1536 g 0.208 mol) was added and the reaction was stirred for a further 30 minutes. The reaction mixture was diluted with water and flushed through a hydrophobic frit. The organic phase was concentrated under vacuum and purified by acidic reverse phase HPLC affording the title compound (37 mg).

MS (ESI) m/z 558.3 [M+H]$^+$

Example 17

N-tert-Butyl-3-((4-(5-chloro-4-(3-isobutylureido)-2-methoxybenzoyl)piperazin-1-yl)methyl)benzamide Example 18

N-tert-Butyl-3-((4-(4-(3-isobutylureido)-2-methoxybenzoyl)piperazin-1-yl)methyl)benzamide

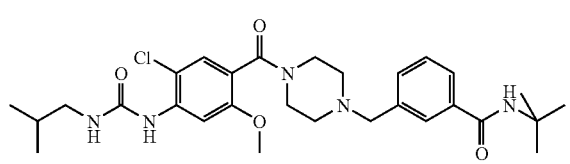

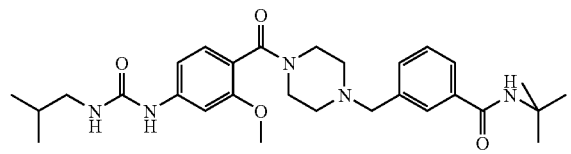

A: 3-((4-(4-Amino-2-methoxybenzoyl)piperazin-1-yl)methyl)-N-tert-butylbenzamide

A: 3-((4-(4-Amino-3-(trifluoromethoxy)benzoyl)piperazin-1-yl)methyl)-N-tert-butylbenzamide

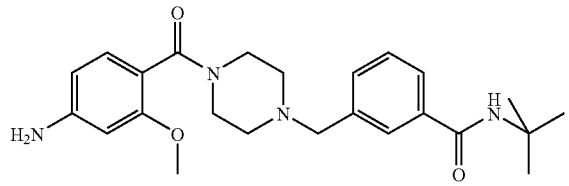

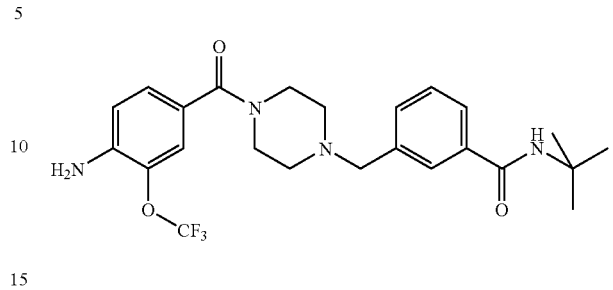

1-Propanephosphonic acid cyclic anhydride (12.91 g, 20.2 mmol, 12.91 mL) was added dropwise to a solution of 4-amino-2-methoxybenzoic acid (1.70 g, 10.1 mmol), N-tert-butyl-3-(piperazin-1-ylmethyl)benzamide (3.07 g, 11.2 mmol) and triethylamine (3.08 g, 30.3 mmol, 4.23 mL) in dichloromethane. The reaction was stirred at room temperature for 1 hour. The reaction was concentrated under reduced pressure and the residue was taken up with ethyl acetate, washed with water, sodium hydrogen carbonate and brine. The organic phase was concentrated under vacuum to afford the title compound (1.39 g). MS (ESI) m/z 425.4 [M+H]+

1-Propanephosphonic acid cyclic anhydride (5.76 g, 92 mmol, 5.38 mL) was added dropwise to a solution of 4-amino-3-(trifluoromethoxy)benzoic acid (1 g, 4.6 mmol), N-tert-butyl-3-(piperazin-1-ylmethyl)benzamide (1.3952 g, 5.1 mmol) and triethylamine (1.37 g, 13.8 mmol, 1.886 mL) in dichloromethane. The reaction was stirred at room temperature for 1 hour. The reaction was concentrated under reduced pressure and the residue was taken up with ethyl acetate, washed with water, sodium hydrogen carbonate and brine. The organic phase was concentrated under vacuum to afford the title compound (1.36 g).

MS (ESI) m/z 479.3 [M+H]+

B: N-tert-Butyl-3-((4-(4-(3-isobutylureido)-2-methoxybenzoyl)piperazin-1-yl)methyl)benzamide 3-((4-(4-Amino-2-methoxybenzoyl)piperazin-1-yl)methyl)-N-tert-butylbenzamide (200 mg, 0.48 mmol) and 4-nitrophenol chloroformate (475 mg, 0.48 mmol) were combined and stirred in dichloromethane for 1 hour. Isobutylamine (102.4 mg, 1.4 mmol, 0.14 mL) was added and the reaction mixture was stirred for 30 minutes. The reaction mixture was diluted with water and flushed through a hydrophobic fret. The organic phase was concentrated under reduced pressure and purified by acidic reverse phase HPLC to afford the title compound (67 mg). MS (ESI) m/z 524.5 [M+H]+

B: N-tert-Butyl-3-((4-(4-(3-isobutylureido)-3-(trifluoromethoxy)benzoyl)piperazin-1-yl)methyl)benzamide 3-((4-(4-Amino-3-(trifluoromethoxy)benzoyl)piperazin-1-yl)methyl)—N-tert-butyl-benzamide (250 mg, 0.525 mmol) and 4-nitrophenol chloroformate (106 mg, 0.525 mmol) were combined and stirred in dichloromethane for 1 hour. Isobutylamine (0.115 g, 1.6 mmol, 0.156 mL) was added and the reaction mixture was stirred for 30 minutes. The reaction mixture was diluted with water and flushed through a hydrophobic frit. The organic phase was concentrated under vacuum and purified by basic reverse phase HPLC to afford the title compound (20 mg), MS (ESI) m/z 578.5 [M+H]+

Example 19

N-tert-Butyl-3-((4-(4-(3-isobutylureido)-3-(trifluoromethoxy)benzoyl)piperazin-1-yl)methyl)benzamide

Example 20

N-tert-Butyl-3-((4-(5-chloro-4-(3-(cyclopropylmethyl)ureido)-2-ethoxybenzoyl)piperazin-1-yl)methyl)benzamide

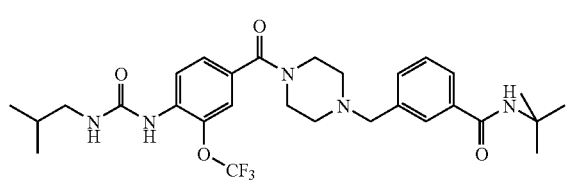

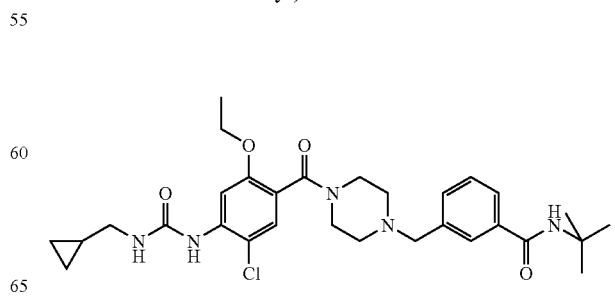

49

A: 3-((4-(4-Amino-5-chloro-2-ethoxybenzoyl)piperazin-1-yl)methyl)-N-tert-butylbenzamide

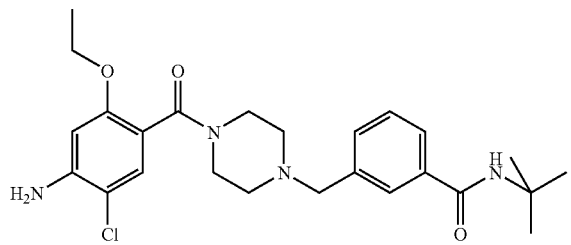

1-Propanephosphonic acid cyclic anhydride (5.90 g, 9.2 mmol, 5.52 mL) was added dropwise to a solution of 4-ammo-5-chloro-2-ethoxy benzoic acid (1 g, 4.6 mmol), N-tert-butyl-3-(piperazin-1-ylmethyl)benzamide (1.40 g, 5.1 mmol) and triethylamine (1.401 g, 13.8 mmol, 1.93 mL) in dichloromethane. The reaction mixture was stirred at room temperature for 2 hours. The reaction was concentrated under reduced pressure and the residue was taken up in ethyl acetate, washed with water, sodium hydrogen carbonate and brine. The organic phase was concentrated under vacuum to afford the title compound (2.08 g).

MS (ESI) m/z 474.1 [M+H]$^+$

B: N-tert-Butyl-3-((4-(5-chloro-4-(3-(cyclopropylmethyl)ureido)-2-ethoxybenzoyl)piperazin-1-yl)methyl)benzamide 3-((4-(4-Amino-5-chloro-2-ethoxybenzoyl)piperazin-1-yl)methyl)-N-tert-butylbenzamide (250 mg, 0.525 mmol) and 4-nitrophenol chloroformate (425.7 mg, 0.525 mmol) were combined and stirred in dichloromethane for 1 hour. Cyclopropylmethylamine (0.114 g, 1.6 mmol, 0.139 mL) was added and the reaction was stirred for 30 minutes. The reaction mixture was diluted with water and flushed through a hydrophobic frit. The organic phase was concentrated under reduced pressure and purified by basic reverse phase HPLC to give the title compound (9.1 mg).

MS (ESI) m/z 570.5 [M+H]$^+$

Example 21

N-tert-Butyl-3-((4-(3-methyl-4-(3-neopentylureido)benzoyl)piperazin-1-yl)methyl)benzamide

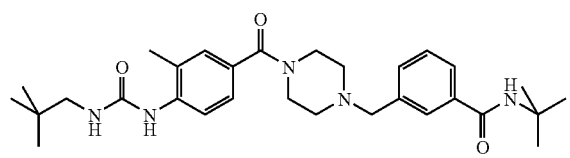

50

A: 3-((4-(4-Amino-3-methylbenzoyl)piperazin-1-yl)methyl)-N-tert-butylbenzamide

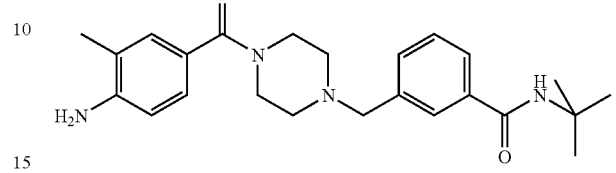

To a stirred solution, of. 4-amino-3-methylbenzoic acid (3.31 mmol, 0.50 g), N-tert-butyl-3-(piperazin-1-ylmethyl)benzamide (3.45 mmol, 0.95 g) and triethylamine (14.35 mmol, 2.00 mL, 1.452 g) in dichloromethane (10 mL) was added 1-propanephosphonic acid cyclic anhydride (6.75 mmol, 4 mL, 4.30 g, 50% in ethyl acetate) dropwise. The mixture was allowed to stir for 1 hour. After this time ethyl acetate was added and the organic mixture was washed with saturated sodium hydrogen carbonate (×2), water (×2) and finally brine. The organic layer was dried with sodium sulfate and concentrated under vacuum to yield the title compound (0.60 g).

MS (ESI) m/z 409.3 [M+H]$^+$

B: N-tert-Butyl-3-((4-(3-methyl-4-(3-neopentylureido)benzoyl)piperazin-1-yl)methyl)benzamide To a stirred solution of 3-((4-(4-amino-3-methylbenzoyl)piperazin-1-yl)methyl)-N-tert-butylbenzamide (0.153 mmols 62.5 mg) in dichloromethane (2 mL) was added 4-nitrophenylchloroformate (0,153 mmol, 30.8 mg). After 1 hour stirring, 2,2-dimethylpropan-1-amine (0.306 mmol, 26.7 mg) was added and stirring continued for 1 hour. The reaction was concentrated under vacuum and the residue dissolved in methanol (1 mL). Purification by basic reverse phase HPLC gave the title compound (11.5 mg).

MS (ESI) m/z 522.7 [M+H]$^+$

Example 22

N-tert-Butyl-3-((4-(3-methoxy-4-(3-neopentylureido)benzoyl)piperazin-1-yl)methyl)benzamide

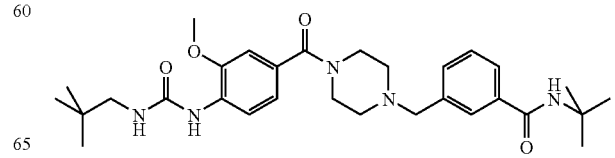

A: 3-((4-(4-Amino-3-methoxybenzoyl)piperazin-t-yl)methyl)-N-tert-butylbenzamide

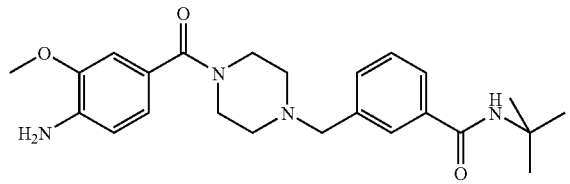

To a stirred solution of 4-amino-3-methoxybenzoic acid (5.98 mmol, 1 g), N-tert-butyl-3-(piperazin-1-ylmethyl)benzamide (5,99 mmol, 1.65 g) and triethylamine (28.7 mmol, 4 mL, 2.90 g) in dichloromethane (20 mL) was added 1-propanephosphonic acid cyclic anhydride (13.50 mmol, 8 mL, 8.59 g, 50% solution in ethyl acetate) dropwise. After 1 hour stirring, ethyl acetate was added and the organic mixture was washed with saturated sodium hydrogen carbonate (×2), water (×2) and finally brine. The organic phase was dried with sodium sulfate and concentrated under vacuum to yield the title compound (1.2 g). MS (ESI) m/z 425.3[M+H]⁺

B: N-tert-Butyl-3-((4-(3-methoxy-4-(3-neopentylureido)benzoyl)piperazin-1-yl)methyl)benzamide To a stirred solution of 3-((4-(4-amino-3-methoxybenzoyl)piperazin-1-y)methyl)-N-tert-butylbenzamide (0.155 mmol, 66 mg) in dichloromethane (2 mL) was added 4-nitrophenylchloroformate (0.155 mmol, 31.3 mg). After 1 hour stirring, 2,2-dimethylpropan-1-amine (0.311 mmol, 27.1 mg) was added and stirring continued for 1 hour. The reaction was concentrated under vacuum and the residue dissolved in methanol (1 mL). Purification by basic reverse phase HPLC gave the title compound (35 mg). MS (ESI) m/z 539.0 [M+H]⁺

Example 23

N-tert-Butyl-3-((4-(4-(3-neopentylureido)-2-(trifluoromethyl)benzoyl)piperazin-1-yl)methyl)benzamide

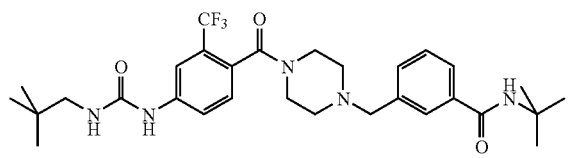

A: 3-((4-(4-Amine-2-(trifluoromethyl)benzoyl)piperazin-1-yl)methyl)-N-tert-butylbenzamide

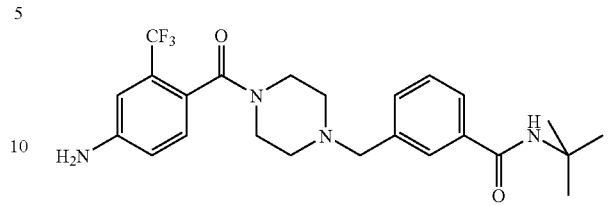

Step 1: To a stirred solution of N-tert-butyl-3-(piperazin-1-ylmethyl)benzamide (3.99 mmol, 1.1 g), 4-nitro-2-(trifluoromethyl)benzoic acid (3.83 mmol. 0.9 g) and triethylamine (28.7 mmol, 4 mL. 2.90 g) in dichloromethane (20 mL) was added 1-propanephosphonic acid cyclic anhydride (8.94 mmol, 5.3 mL, 5.69 g, 50% solution in ethyl acetate) dropwise. After 1 hour stirring, ethyl acetate was added and the organic mixture was washed with saturated sodium hydrogen carbonate (×2), water (×2) and finally brine. The organic mixture was dried with sodium sulfate and concentrated under vacuum to give the intermediate N-tert-butyl-3-((4-(4-nitro-2(trifluoromethyl)benzoyl)piperazin-1-yl)methyl)benzamide.

Step 2: To a stirred mixture of N-tert-butyl-3-((4-(4-nitro-2-(trifluoromethyl)benzoyl)piperazin-1-y)methyl)benzamide (2.234 mmol, 1.1 g) and iron powder (22.38 mmol, 1.25 g) in isopropanol (10 mL) was added 1M hydrochloric acid (3.00 mmol, 3 mL). The reaction was allowed to stir for 12 hours and was then concentrated under vacuum. Dichloromethane was added and the organic mixture was washed with water, dried with sodium sulfate, filtered and concentrated under vacuum to yield the title compound (0.86 g). MS (ESI) m/z 463.5 [M+H]⁺

B: N-tert-Butyl-3-((4-(4-(3-neopentylureido)-2-(trifluoromethyl)benzoyl)piperazin-1-yl)methyl)benzamide To a stirred solution of 3-((4-(4-amino-2-(trifluoromethyl)benzoyl)piperazin-1-yl)methyl)-N-tert-butylbenzamide (0.123 mmol, 57 mg) in dichloromethane (2 mL) was added 4-nitrophenylchloroformate (0.123 mmol, 24.84 mg). After 1 hour stirring, 2,2-dimethylpropan-1-amine (0.123 mmol, 10.74 mg) was added and stirring was continued for 1 hour. The reaction was concentrated under reduced pressure and the residue dissolved in methanol (1 mL). Purification by basic reverse phase HPLC gave the title compound (27 mg). MS (ESI) m/z 577.0 [M+H]⁺

Example 24

N-tert-Butyl-3-((4-(2,3-difluoro-4-(3-neopentylureido)benzoyl)piperazin-1-yl)methyl)benzamide

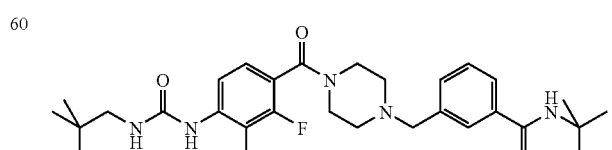

A: 3-((4-(4-Amino-2,3-difluorobenzoyl)piperazin-1-yl)methyl)-N-tert-butylbenzamide

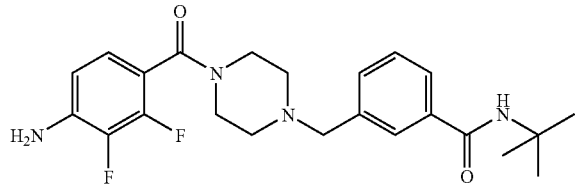

To 4-amino-2,3-difluorobenzoic acid (4.19 mmol, 725 mg) and N-tert-butyl-3-(piperazin-1-ylmethyl)benzamide (2.54 mmol, 700 mg) and triethylamine (10.76 mmol, 1.5 mL, 1089 mg) in dichloromethane (30 mL) was added 1-propanephosphonic acid cyclic anhydride (6.75 mmol, 4 mL, 4296 mg, 50% solution in ethyl acetate) dropwise. The mixture was allowed to stir for 2 hours and then ethyl acetate was added, The organic mixture was washed with saturated sodium hydrogen carbonate, water, and saturated sodium chloride. The organic phase was dried with sodium sulfate, filtered and concentrated under reduced pressure to give the title compound (1.28 g), MS (ESI) m/z 431.6 [M+H]+

B: N-tert-Butyl-3-((4-(2,3-difluoro-4-(3-neopentylureido)benzoyl)piperazin-1-yl)methyl)benzamide To a stirred solution of 3-((4-(4-amino-2,3-difluorobenzoyl)piperazin-1-yl)methyl)-N-tert-butylbenzamide (0.077 mmol, 33 mg) in dichloromethane (1 mL) was added 4-nitrophenylchloroformate (0.080 mmol, 16.22 mg). After 1 hour stirring, 2,2-dimethylpropan-1-amine (0.077 mmol, 150 μl, 6.68 mg) was added and stirring continued for 1 hour. The reaction was concentrated under reduced pressure and the residue dissolved in methanol (1 mL), Purification by acidic reverse phase HPLC and strong cation exchange column chromatography gave the title compound (7 mg), MS (ES) m/z 544.3 [M+H]+

The following compounds below were prepared in a similar manner:

24B: N-tert-Butyl-3-((4-(2,3-difluoro-4-(3-isopentylureido)benzoyl)piperazin-1-yl)methyl)benzamide
MS (ESI) m/z 544.3 [M+H]+

24C: N-tert-butyl-3-((4-(4-(3-Butylureido)-2,3-difluorobenzoyl)piperazin-1-yl)methyl)benzamide
MS (ESI) m/z 530.3 [M+H]+

24D: N-tert-Butyl-3-((4-(2,3-difluoro-4-(3-isobutylureido)benzoyl)piperazin-1-yl)methyl)benzamide
MS (ESI) m/z 530.3 [M+H]+

24E: N-tert-Butyl-3-((4-(4-(3-(cyclopropylmethyl)ureido)-2,3-difluorobenzoyl)piperazin-1-yl)methyl)benzamide
MS (ES) m/z 528.3 [M+H]+

Example 25

N-tert-Butyl-3-((4-(4-(3-cyclobutylureido)-2,3-difluorobenzoyl)piperazin-1-yl)methyl)benzamide Hydrochloride

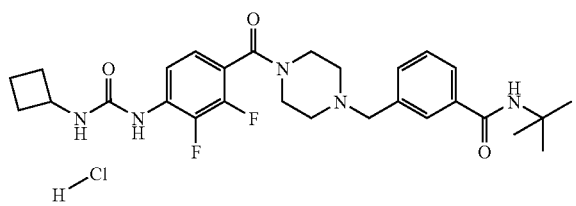

To a stirred solution of bis(trichloromethyl) carbonate (0.26 mmol, 76 mg) in dichloromethane (3 mL) was added a mixture of 3-((4-(4-amino-2,3-difluorobenzoyl)piperazin-1-yl)methyl)-N-tert-butylbenzamide (0.6 mmol, 257 mg) and N-ethyl-N-isopropylpropan-2-amine (0.11 mL) in dichloromethane (2 mL) dropwise over 2 minutes. After 30 minutes stirring, a mixture of cyclobutylamine (1.192 mmol, 0.113 mL, 85 mg) and N-ethyl-N-isopropylpropan-2-amine (0.22 mL) was added. After 2 hours stirring, the reaction mixture was diluted with dichloromethane and water. The organic layer separated, dried with sodium sulfate and purified by basic reverse phase HPLC. The water/acetonitrile fractions were concentrated under vacuum. The residue was taken up in dichloromethane (1 mL) and 2M hydrochloric acid (2 mL) in ether was added. The volatiles were removed under reduced pressure. Drying in a vacuum oven over night at 50° C. gave the title compound (170 mg). MS (ESI) m/z 528.5[M+H]+

Example 26

N-tert-Butyl-3-((4-(2-chloro-4-(3-(cyclopropylmethyl)ureido)-3-fluorobenzoyl)piperazin-1-yl)methyl)benzamide

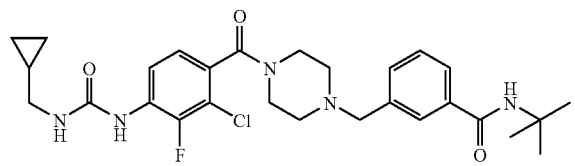

A: 4-Amino-2-chloro-3-fluorobenzoic Acid

4-Amino-2-chloro-3-fluorobenzonitrile (500 mg, 2.93 mmol) and sodium hydroxide (4M, 18 mL) were mixed with ethanol (8 mL) and heated to reflux for 18 hours. After this time the mixture was allowed to cool to room temperature and 1M hydrochloric acid was added until pH 1 was achieved. Ethyl acetate was added and the organic layer was separated and washed with water and brine. The organic phase was dried with sodium sulfate, filtered and concentrated under vacuum to give the title compound (500 mg), MS (ESI) m/z 188.1 [M–H]+

B: 3-((4-(4-Amino-2-chloro-3-fluorobenzoyl)piperazin-1-yl)methyl)-N-tert-butylbenzamide A: 3-((4-(4-Amino-3-chloro-2-fluorobenzoyl)piperazin-1-yl)methyl)-N-tert-butylbenzamide

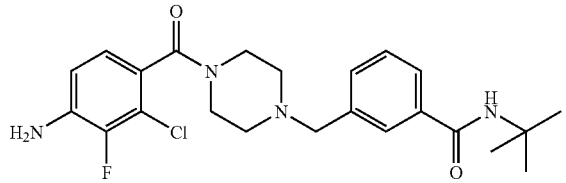

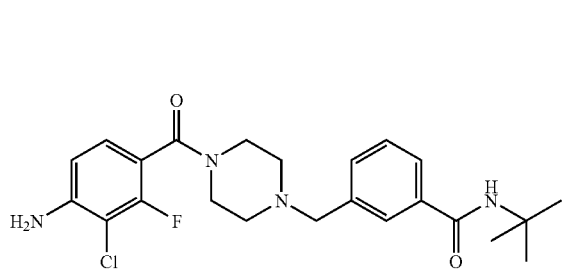

To 4-amino-2-chloro-3-fluorobenzoic acid (2.64 mmol, 500 mg) and N-tert-butyl-3-(piperazin-1-ylmethyl)benzamide (2.54 mmol, 700 mg) and triethylamine (10.76 mmol, 1.5 mL, 1089 mg) in dichloromethane (30 mL) was added 1-propanephosphonic acid cyclic anhydride (6.75 mmol, 4 mL, 4296 mg, 50% solution in ethyl acetate). After 2 hours stirring, ethyl acetate was added. The organic mixture was washed with saturated sodium hydrogen carbonate, water, and saturated sodium chloride. The organic mixture was dried sodium sulfate, filtered and concentrated under reduced pressure. The crude residue was purified by silica chromatography (eluting with 5% methanol in dichloromethane) to yield the title compound (325 mg). MS (ESI) m/z 447.1 [M+H]$^+$ To 4-amino-3-chloro-2-fluorobenzoic acid (0.754 mmol, 143 mg), N-tert-butyl-3-(piperazin-1-ylmethyl)benzamide (0.754 mmol, 208 mg) and triethylamine (3.02 mmol, 0.421 ml, 305 mg) in dichloromethane (8 mL) was added 1-propanephosphonic acid cyclic anhydride (1.886 mmol, 1.117 mL, 1200 mg, 50% solution in ethyl acetate). After 2 hours stirring, ethyl acetate was added. The organic solution was washed with saturated sodium hydrogen carbonate, water, and saturated sodium chloride. The organic phase was dried with sodium sulfate, filtered and concentrated. The residue was purified by silica chromatography to yield the title compound (155 mg).

MS (ESI) m/z 447.3 [M+H]$^+$

C: N-tert-Butyl-3-((4-(2-chloro-4-(3-(cyclopropylmethyl)ureido)-3-fluorobenzoyl)piperazin-1-yl)methyl)benzamide To a stirred solution of bis(trichloromethyl) carbonate (0.076 mmol, 22.60 mg) in dichloromethane (3 mL) was added triethylamine (40 mL) and 3-((4-(4-amino-2-chloro-3-fluorobenzoyl)piperazin-1-yl)methyl)-N-tert-butylbenzamide (0.206 mmol, 92 mg) in dichloromethane (3 mL). The reaction mixture was heated to reflux for 2 hours. After this time the reaction was allowed to cool to room temperature and cyclopropylmethylamine (35 µl, 0.412 mmol) and triethylamine (35 µl) were added. After 30 minutes stirring, the volatiles were removed under reduced pressure and the crude residue was purified by silica chromatography (eluting with 5% methanol in dichloromethane) to yield the title compound (80 mg).

MS (ESI) m/z 544.3 [M+H]$^+$

B: N-tert-Butyl-3-((4-(3-chloro-4-(3-(cyclopropylmethyl)ureido)-2-fluorobenzoyl)piperazin-1-yl)methyl)benzamide To a stirred solution of bis(trichloromethyl) carbonate (0.128 mmol, 38.1 mg) in dichloromethane (6 mL) was added a mixture of triethylamine (0.867 mmol, 0.121 mL, 88 mg) and 3-((4-(4-amino-3-chloro-2-fluorobenzoyl)piperazin-1-yl)methyl)-N-tert-butylbenzamide (0.347 mmol, 155 mg) in dichloromethane (6 mL). The mixture was heated to reflux for 2 hours before being cooled to room temperature. Cyclopropylmethylamine (0.694 mmol, 0.060 mL, 49.3 mg) was added and the mixture stirred for 2 hours. After this time the reaction was concentrated under reduced pressure and purified by silica chromatography to yield the title compound (17 mg).

MS (ESI) m/z 544.3 [M+H]$^+$

The following compound was prepared in a similar manner:

27B: N-tert-Butyl-3-((4-(3-chloro-2-fluoro-4-(3-isobutylureido)benzoyl)piperazin-1-yl)methyl)benzamide Example 27

N-tert-Butyl-3-((4-(3-chloro-4-(3-(cyclopropylmethyl)ureido)-2-fluorobenzoyl)piperazin-1-yl)methyl)benzamide

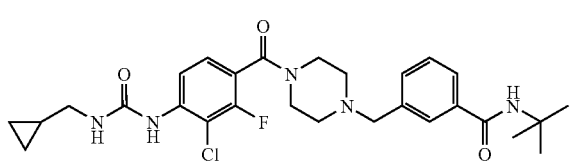

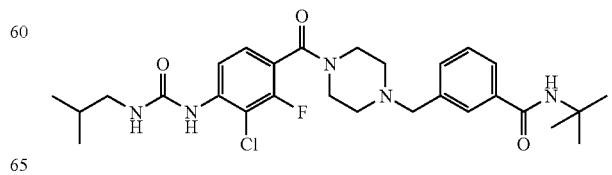

MS (ESI) m/z 546.5 [M+H]$^+$

Example 28

N-tert-Butyl-3-((4-(6-(3-phenylureido)nicotinoyl)piperazin-1-yl)methyl)benzamide 2,2,2-trifluoroacetate

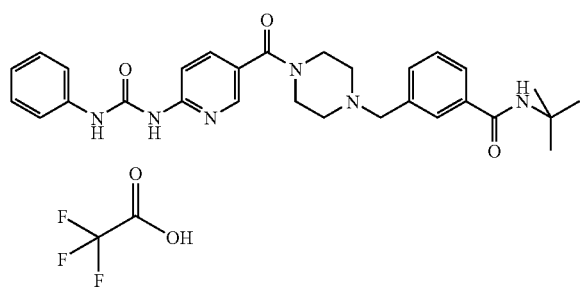

A: Methyl 6-(3-phenylureido)nicotinate

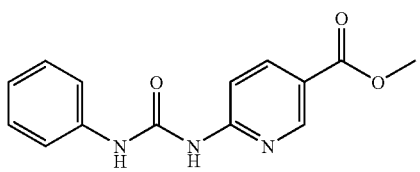

To a solution of methyl 6-aminonicotinate (500 mg, 3.29 mmol) in N,N-diemthylformamide (5 mL) was added phenyl isocyanate (358 μL, 3.29 mmol). The mixture was heated to 100° C. for 2 hours and was then concentrated under vacuum to give the title compound (928 mg).
MS (ESI) m/z 272.1 [M+H]$^+$

B: 6-(3-Phenylureido)nicotinic Acid

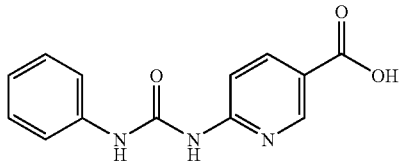

Methyl 6-(3-phenylureido)nicotinate (200 mg, 0.43 mmol) was dissolved in methanol (2 mL) at room temperature. Lithium hydroxide (100 mg, 4.17 mmol) was added, followed by water (10.5 mL). The mixture was heated to 50° C. and stirred overnight. The mixture was brought to pH 4-5 by addition of concentrated hydrochloric acid. The solid that had formed was then filtered and dried under vacuum to give the title compound (69 mg). MS (ESI) m/z 258.1[M+H]$^+$

C: N-tert-Butyl-3-((4-(6-(3-phenylureido)nicotinoyl)piperazin-1-yl)methyl)benzamide 2,2,2-trifluoroacetate To a mixture of N-tert-butyl-3-(piperazin-1-ylmethyl)benzamide dihydrochloride (16 mg, 46 μmol) and N-ethyl-N-isopropylpropan-2-amine (20.4 μl, 117 μmol) in N,N-diemthylformamide (3 mL) was added 6-(3-phenylureido)nicotinic acid (10 mg, 39 μmol), followed by O-(7-azabenzotriazol-1-yl)-N,N,N,N-tetramethyl uronium hexafluorophosphate (18 mg, 47.3 μmol, HATU). The solution was stirred at room temperature for 16 hours. The reaction mixture was concentrated under vacuum and was partitioned between dichloromethane (10 mL) and water (10 mL). The aqueous layer was extracted with of dichloromethane (×3). The combined organic layers were dried and concentrated under vacuum. The resulting residue was dissolved in methanol and purified by acidic reverse phase HPLC yielding the title compound (19.9 mg).
MS (ESI) m/z 515.1 [M+H]$^+$

Example 29

N-tert-Butyl-3-((4-(5-(3-phenylureido)pyrazine-2-carbonyl)piperazin-1-yl)methyl)benzamide 2,2,2-trifluoroacetate

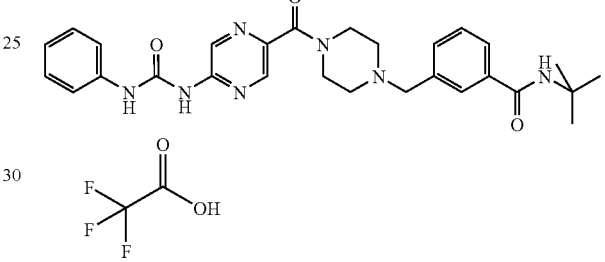

A: Diethyl pyrazine-2,5-dicarboxylate

A mixture of pyrazine-2,5-dicarboxylic acid (4.00 g, 23.79 mmol) and hydrochloric acid (1M in ethanol) was sealed in a pressure vessel and heated to 80° C. for 48 hours. The cloudy mixture was filtered through a short pad of celite and the filtrate was concentrated under vacuum. The residue was partitioned between ethyl acetate and saturated aqueous sodium hydrogen carbonate. The organic layer was separated, washed with brine, dried over magnesium sulfate and concentrated under vacuum to obtain the title compound (1.84 g).
MS (ESI) m/z 225.0 [M+H]$^+$

B: Ethyl 5-(hydrazinecarbonyl)pyrazine-2-carboxylate

A mixture of diethyl pyrazine-2,5-dicarboxylate (1.75 g, 7.81 mmol) and ethanol (15 mL) was heated to 75° C. to obtain a homogeneous solution. After cooling to room temperature, a solution of hydrazine monohydrate (0.281 g, 7.03 mmol) in ethanol (3.5 mL) was added to the solution dropwise over 4 hours. After stirring at room temperature overnight, a solid had precipitated out of the reaction mixture. The solid was collected by filtration and dried under vacuum to give the title compound (1.05 g).
MS (ESI) m/z 211.1 [M+H]$^+$

C: Ethyl 5-(azidocarbonyl)pyrazine-2-carboxylate

A mixture of ethyl 5-(hydrazinecarbonyl)pyrazine-2-carboxylate (1.00 g, 4.76 mmol), sodium nitrite (1.76 g, 25.5 mmol), water (18 mL) and dichloromethane (18 mL) was cooled to 0 to 5° C. (ice-bath) under vigorous stirring. 6M hydrochloric acid (7.4 mL) was added drop-wise over 30 minutes, keeping the temperature under 10° C. After stirring for a further 30 minutes, the organic layer was separated, dried over magnesium sulfate and concentrated under vacuum to afford the title compound (1.01 g).

MS (ESI) m/z 222.2 [M+H]$^+$

D: Ethyl 5-(tert-butoxycarbonyl)pyrazine-2-carboxylate

A mixture of ethyl 5-(azidocarbonyl)pyrazine-2-carboxylate (1.00 g, 4.52 mmol), tert-butanol (1.5 mL, 20.2 mmol) and toluene (15 mL) was heated to reflux for 1 hour. After cooling to room temperature, the solid precipitate was collected to afford the title compound (0.75 g).

MS (ESI) m/z 268.3 [M+H]$^+$

E: 5-(tert-Butoxycarbonyl)pyrazine-2-carboxylic Acid

To a mixture of ethyl 5(tert-butoxycarbonyl)pyrazine-2-carboxylate (0.742 g, 2.78 mmol) and methanol (20 mL) was added potassium hydroxide (0.23 g, 4.1 mmol) in wafer (2 mL) and the reaction was stirred at room temperature overnight. The solvent was removed under vacuum and the residue was dissolved in wafer (5 mL) and acidified to pH 2 with 1M hydrochloric acid. The solid precipitate was collected by filtration to afford the title compound (0.61 g). MS (ESI) m/z 240.2 [M+H]$^+$

F: tert-Butyl 5-(4-(3-(tert-butylcarbamoyl)benzyl)piperazine-1:carbonyl)pyrazin-2-ylcarbamate

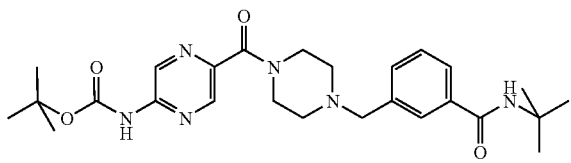

A mixture of 5-(tert-butoxycarbonyl)pyrazine-2-carboxylic acid (68.5 mg, 0.286 mmol), O-(7-azabenzotriazol-1-yl)-N,N,N,N-tetramethyl uranium hexafluorophosphate (114 mg, 0.03 mmol), N-ethyl-N-isopropylpropan-2-amine (330 mg, 2.58 mmol) and N,N-dimethylformamide (1 mL) was stirred at room temperature for 30 minutes. N-tert-butyl-3-(piperazin-1-ylmethyl)benzamide dihydrochloride (100 mg, 0.286 mmol) was added and the mixture was stirred at room temperature overnight. The reaction was concentrated under reduced pressure and the residue was partitioned between ethyl acetate and water. The organic layer was separated, washed with water and brine, dried over magnesium sulfate and concentrated under vacuum to afford the title compound (0.12 g). MS (ESI) m/z 497.3 [M+H]$^+$

G: 3-((4-(2-Aminopyrazine-5-carbonyl)piperazin-1-yl)methyl)-N-tert-butylbenzamide

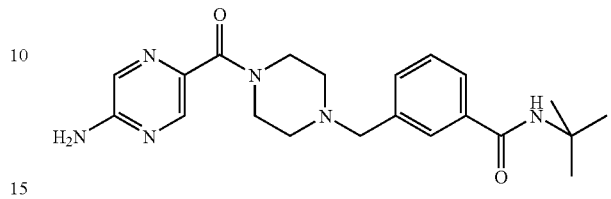

A mixture of tert-butyl 5-(1-(3-(tert-butylcarbamoyl)benzyl)piperazine-4-carbonyl)pyrazin-2-ylcarbamate (Example 30; 120 mg, 0.242 mmol), dichloromethane (2 mL) and trifluoroacetic acid (2 mL) was stirred at room temperature for 3 hours and was then concentrated under vacuum. The residue was triturated with diethyl ether and then gravity filtered over fluted paper. The collected solid was partitioned between ethyl acetate and saturated aqueous sodium hydrogen carbonate. The aqueous layer was separated and extracted with ethyl acetate. The combined organic layers were dried over magnesium sulfate, filtered and concentrated under vacuum to afford the title compound (89 mg). MS (ESI) m/z 397.2 [M-+H]$^+$

H: N-tert-Butyl-3-((4-(5-(3-phenylureido)pyrazine-2-carbonyl)piperazin-1-yl)methyl)benzamide 2,2,2-trifluoroacetate A mixture of 3-((4-(2-aminopyrazine-5-carbonyl)piperazin-1-yl)methyl)-N-tert-butylbenzamide (15 mg, 0.038 mmol), phenyl isocyanate (0.01 mL, 0.092 mmol) and dioxane (0.5 mL) was stirred at 70° C. overnight. The reaction was concentrated under reduced pressure and purified by acidic reverse phase HPLC to afford the title compound (3 mg). MS (ESI) m/z 516.3 [M+H]$^+$ Example 30

N-tert-Butyl-3-((4-(4-(3-cyclobutylureido)benzoyl)-1,4-diazepan-1-yl)methyl)benzamide 2,2,2-trifluoroacetate

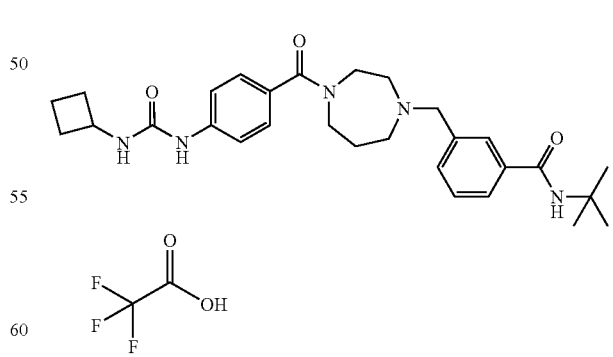

A: Ethyl 4-(3-cyclobutylureido)benzoate

Cyclobutylamine (27.91 g, 392.4 mmol, 33.5 mL) was added dropwise to a stirred solution of ethyl 4-isocyanatobenzoate (25 g, 130.8 mmol) in dichloromethane. After 40 minutes stirring, the solid precipitate that had formed was filtered off and dried to afford the title compound (30.28 g). MS (ESI) m/z 263.1 [M+H]$^+$ B: 4-(3-Cyclobutylureido)benzoic Acid Ethyl 4-(3-cyclobutylureido)benzoate (49.9 mmol, 13.1 g) was suspended in ethanol (400 m) and treated with sodium hydroxide (300 mmol, 74.9 ml). The mixture was then stirred at reflux for 18 hours. The reaction was allowed to cool, diluted with toluene (100 mL) and concentrated under vacuum. Acidification to pH 3 with 5M aqueous hydrochloric acid produced a white solid. The solid was collected by vacuum filtration, washed with cold ethanol and dried under vacuum to give the title compound as a white powder (11.0 g).

$^1$H NMR (CD$_3$OD, 400 MHz): δ 1.73 (2 H, m), 1.92 (2 H, m), 2.32 (2 H, m), 4.22 (1 H, m), 7.45 (2 H, d), 7.90 (2 H, d).

C: tert-Butyl 4-(3-(tert-butylcarbamoyl)benzyl)-1,4-diazepane-1-carboxylate

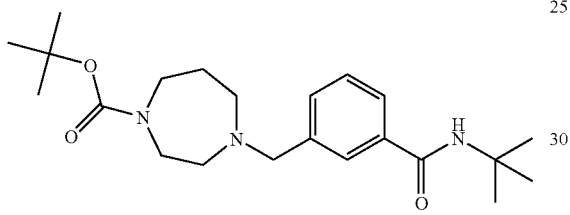

To a solution of tert-butyl-1-homopiperazine carboxylate (0.25 g, 1.25 mmol) and N-tert-butyl-3-(chloromethyl)benzamide (0.470 g, 1.25 mmol) in tetrahydrofuran (4 mL) was added N-ethyl-N-isopropylpropan-2-amine (0.33 mL, 1.88 mmol). The resultant mixture was stirred at 80° C. for 16 hours. The mixture was cooled to room temperature, diluted with dichloromethane (50 mL) and washed with saturated ammonium chloride (aqueous) and brine. The organic phase was dried (sodium sulfate), filtered and concentrated under vacuum. The residue was purified by column chromatography on silica (using a solvent gradient of dichloromethane/methanol) to afford the title compound (0.435 g) as a white solid. MS (ESI) m/z 389.9 [M+H]$^+$ D: 3-((1,4-Diazepan-1-yl)methyl)-N-tert-butylbenzamide Hydrochloride

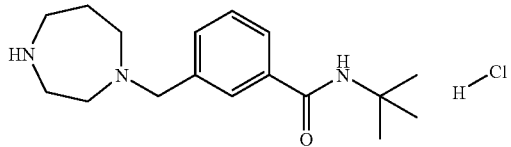

tert-Butyl 4-(3-(tert-butylcarbamoyl)benzyl)-1,4-diazepane-1-carboxylate (0.53 g, 1.36 mmol) was treated with an ethanolic solution of hydrochloric acid (3 mL, 14.5 wt % hydrochloric acid in ethanol). The resultant mixture was stirred at room temperature for 2 hours. The mixture was concentrated under vacuum, azeotroped with dichloromethane (×2) and dried under vacuum to afford the title compound (0.394 g) as a white foamy solid. MS (ES) m/z 290.1[M+H]$^+$ E: N-tert-Butyl-3-((4-(4-(3-cyclobutylureido)benzoyl)-1,4-diazepan-1-yl)methyl)benzamide 2,2,2-trifluoroacetate To a solution of 3-((1,4-diazepan-1-yl)methyl)-N-tert-butylbenzamide hydrochloride (0.04 g, 0.138 mmol) in N,N-dimethylformamide (1.5 mL) was added O-(7-azabenzotriazol-1-yl)-N,N,N,N-tetramethyl uronium hexafluorophosphate (0.052 g, 0.138 mmol, HATU), 4-(3-cyclobutylureido)benzoic acid (0.032 g, 0.138 mmol) and N-ethyl-N-isopropylpropan-2-amine (0.060 mL, 0.345 mmol). The reaction mixture was stirred at room temperature for 20 hours and concentrated under vacuum. The residue was diluted with dichloromethane (10 mL) and washed with saturated ammonium chloride (aqueous) and brine. The organic phase was dried (sodium sulfate), filtered and concentrated under vacuum. HPLC purification provided the title compound (0.049 g). MS (ESI) m/z 506.1 [M+H]$^+$ Example 31

(S)—N-tert-Butyl-3-((4-(4-(3-cyclobutylureido)benzoyl)-3-methylpiperazin-1-yl)methyl)benzamide 2,2,2-trifluoroacetate

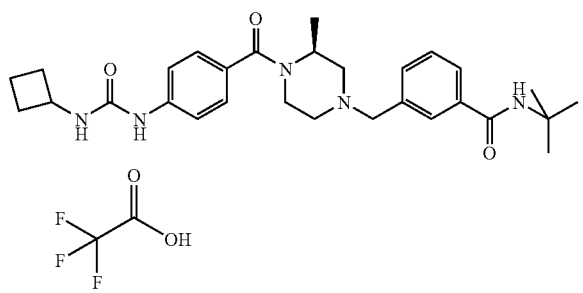

A: (S)-tert-Butyl 4-(4-(3-cyclobutylureido)benzoyl)-3-methylpiperazine-1-carboxylate

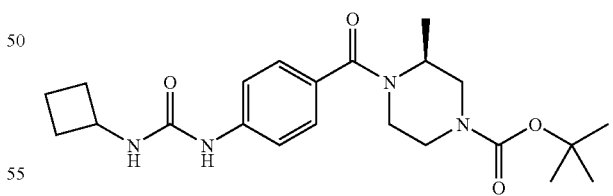

To a solution of (S)-tert-butyl 3-methylpiperazine-1-carboxylate (0.10 g, 0.50 mmol) in N,N-dimethylformamide (5 mL) was added O-(7-azabenzotriazol-1-yl)-N,N,N,N-tetramethyl uronium hexafluorophosphate (0.190 g, 0.50 mmol, HATU), 4-(3-cyclobutylureido)benzoic acid (0.117 g, 0.50 mmol) and N-ethyl-N-isopropylpropan-2-amine (0.13 mL, 0.75 mmol). The reaction mixture was stirred at room temperature for 20 hours and concentrated under vacuum. The residue was diluted with dichloromethane (15 mL) and washed with saturated ammonium chloride (aqueous) and brine. The organic layer was dried (sodium sulfate), filtered and concentrated under vacuum. The crude material was purified by column chromatography on silica (using a solvent gradient of dichloromethane/methanol) to afford the title compound (0.145 g) as a white solid.

MS (ESI) m/z 416.8 [M+H]+

B: (S)-1-Cyclobutyl 3-(4-(2-methylpiperazine-1-carbonyl)phenyl)urea hydrochloride

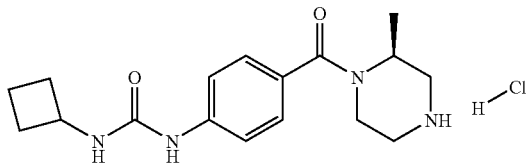

tert-Butyl 4-(4-(3-cyclobutylureido)benzoyl)-3-methylpiperazine-1-carboxylate (0.20 g, 0.48 mmol) was treated with an ethanolic solution of hydrochloric acid (2 mL, 14.5 wt % hydrochloric acid in ethanol). The resultant mixture was stirred at room temperature for 2 hours. The mixture was concentrated under vacuum, azeotroped with dichloromethane (×2) and dried under vacuum to afford the title compound (0.152 g) as a white foamy solid. MS (ESI) m/z 317.0 [M+H]+

C: (S)—N-tert-Butyl-3-((4-(4-(3-cyclobutylureido)benzoyl)-3-methylpiperazin-1-yl)methyl)benzamide 2,2,2-trifluoroacetate To (S)-1-cyclobutyl-3-(4-(2-methylpiperazine-1-carbonyl)phenyl)urea hydrochloride (0.02 g, 0.063 mmol) and N-tert-butyl-3-(chloromethyl)benzamide (0.014 g, 0.063 mmol) in tetrahydrofuran (1 mL) was added N-ethyl-N-isopropylpropan-2-amine (0.028 mL, 0.158 mmol). The resultant mixture was stirred at 80° C. for 16 hours. The mixture was cooled to room temperature, diluted with dichloromethane (50 mL) and washed with saturated ammonium chloride (aqueous) and brine. The organic phase was dried (sodium sulfate), filtered and concentrated under vacuum. HPLC purification provided the title compound (0.003 g). MS (ESI) m/z 506.1 [M+H]+

Example 32

N-tert-Butyl-3-(((2S,6R)-4-(4-(3-cyclobutylureido)benzoyl)-2,6-dimethylpiperazin-1-yl)methyl)benzamide 2,2,2-trifluoroacetate

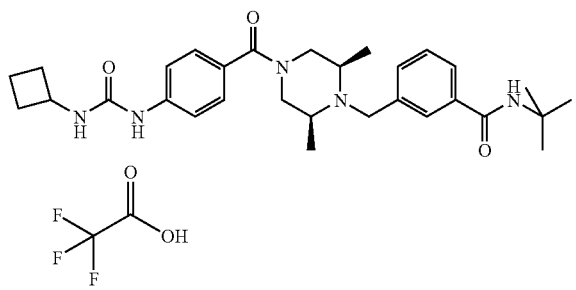

A: (3S,5R)-tert-Butyl 3,5-dimethylpiperazine-1-carboxylate

To a stirring solution of 2,6-cis-dimethylpiperazine (1.0 g, 8.76 mmol) in dichloromethane (19 mL) cooled to 0° C. was added a solution of di-tert-butyl-dicarbonate (1.87 g, 8.58 mmol) in dichloromethane (5 mL). The reaction mixture was slowly warmed to room temperature and stirred for 20 hours. The mixture was diluted with dichloromethane (15 mL) and washed with saturated potassium carbonate (aqueous) and brine. The organic phase was dried (sodium sulfate), filtered and concentrated under vacuum to give the title compound (1.29 g) as a white solid.

MS (ESI) m/z 215.4 [M+H]+

B: (3S,5R)-tert-Butyl 4-(3-(tert-butylcarbamoyl)benzyl)-3,5-dimethylpiperazine-1-carboxylate

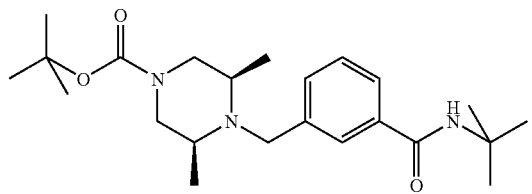

To a solution of (3S,5R)-tert-butyl 3,5-dimethylpiperazine-1-carboxylate (0.05 g, 0.23 mmol) and N-tert-butyl-3-(chloromethyl)benzamide (0.052 g, 0.23 mmol) in tetrahydrofuran (2 mL) was added N-ethyl-N-isopropylpropan-2-amine (0.080 mL, 0.46 mmol). The resultant mixture was stirred at 80° C. for 16 hours. The mixture was cooled to room temperature, diluted with dichloromethane (50 mL) and washed with saturated ammonium chloride (aqueous) and brine. The organic phase was dried (sodium sulfate), filtered and concentrated under vacuum. The crude material was purified by column chromatography on silica (using a solvent gradient of dichloromethane/ethyl acetate) to afford the title compound (0.070 g) as a white solid.

MS (ESI) m/z 404.4 [M+H]+

C: N-tert-Butyl-3-(((2S,6R)-2,6-dimethylpiperazin-1-yl)methyl)benzamide Hydrochloride

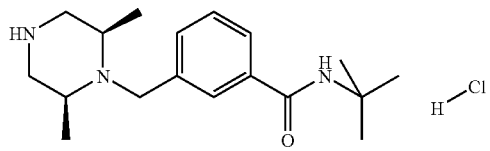

(3S,5R)-tert-Butyl 4-(3-(tert-butylcarbamoyl)benzyl)-3,5-dimethylpiperazine-1-carboxylate (0.07 g, 0.17 mmol) was treated with an ethanolic solution of hydrochloric acid (2 mL, 14.5 wt % hydrochloric acid in ethanol). The resultant mixture was stirred at room temperature for 2 hours. The mixture was concentrated under vacuum, azeotroped with dichloromethane (×2) and dried under vacuum to afford the title compound (0.052 g) as a white foamy solid. MS (ESI) m/z 304.4 [M+H]+

D: N-tert-Butyl-3-(((2S,6R)-4-(4-(3-cyclobutylureido)benzoyl)-2,6-dimethylpiperazin-1-yl)methyl)benzamide 2,2,2-trifluoroacetate To a solution of N-tert-butyl-3-(((2S,6R)-2,6-dimethylpiperazin-1-yl)methyl)benzamide hydrochloride (0.025 g, 0.083 mmol) in N,N-dimethylformamide (2 mL) was added O-(7-azabenzotriazol-1-yl)-N,N,N,N-tetramethyl uronium hexafluorophosphate (0.032 g, 0.083 mmol, HATU), 4-(3-cyclobutylureido)benzoic acid (0.019 g, 0.083 mmol) and N-ethyl-N-isopropylpropan-2-amine (0.036 mL, 0.21 mmol). The reaction mixture was stirred at room temperature for 20 hours and concentrated under vacuum. The residue was diluted with dichloromethane (10 mL) and washed with saturated ammonium chloride (aqueous) and brine. The organic phase was dried (sodium sulfate), filtered and concentrated under vacuum. Acidic reverse phase HPLC purification provided the title compound (0.0039 g). MS (ESI) m/z 520.2 [M+H]$^+$ Example 33

(R)—N-tert-Butyl-3-((4-(4-(3-(cyclopropylmethyl)ureido)-3-fluorobenzoyl)-2-methylpiperazin-1-yl)methyl)benzamide

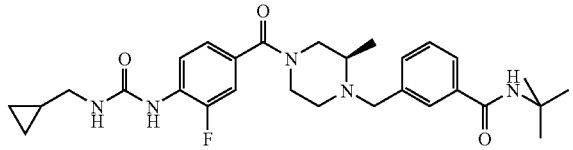

A: (R)-tert-Butyl 4-(3(tert-butylcarbamoyl)benzyl)-3-methylpiperazine-1-carboxylate

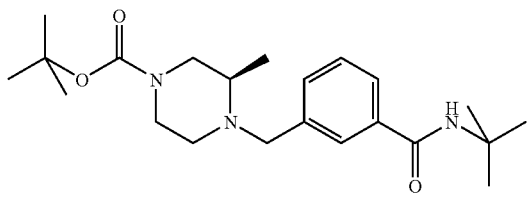

(R)-tert-Butyl 3-methylpiperazine-1-carboxylate was added to a solution containing N-tert-butyl-3-(chloromethyl)benzamide (3.38 g, 14.9 mmol), potassium carbonate (4.11 g, 29.8 mmol) and sodium iodide (catalytic amount) in acetonitrile. The reaction was stirred under reflux for 2 hours. The acetonitrile was removed under reduced pressure. The resulting residue was taken up in dichloromethane and filtered. The filtrate was concentrated under vacuum to afford the title compound (5.82 g).

MS (ESI) m/z 390.5 [M+H]$^+$

B: (R)—N-tert-Butyl-3-((2-methylpiperazin-1-yl)methyl)benzamide

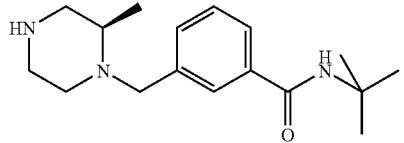

(R)-tert-Butyl 4-(3-(tert-butylcarbamoyl)benzyl)-3-methylpiperazine-1-carboxylate (8.03 g, 20.61 mmol) was stirred in a mixture of dichloromethane:trifluoroacetic acid (1:1) for 2 hours. The reaction mixture was concentrated under vacuum and purified by strong cation exchange column chromatography to afford the title compound (3.06 g).

MS (ESI) m/z 290.3 [M+H]$^+$

C: (R)-3-((4-(4-Amino-3-fluorobenzoyl)-2-methylpiperazin-1-yl)methyl)-N-tert-butylbenzamide

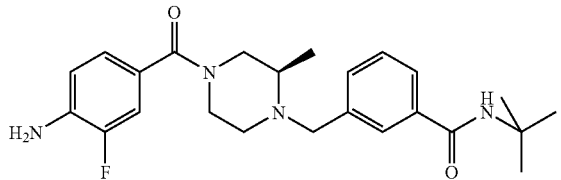

1-Propanephosphonic acid cyclic anhydride (1.967 g, 3 mmol, 1.840 mL, 50% solution in ethyl acetate) was added dropwise to a solution of (R)N-tert-butyl-3-((2-methylpiperazin-1-yl)methyl)benzamide (500 mg, 1.7 mmol), 4-amino-3-fluorobenzoic acid (239.7 mg, 1.5 mmol) and triethylamine (469 mg, 4.5 mmol, 1.84 mL) in dichloromethane. The reaction was stirred at room temperature for 2 hours. The dichloromethane was removed under reduced pressure and the residue was taken up in ethyl acetate, washed with water, sodium hydrogen carbonate and brine. The organic layer was concentrated under vacuum to afford the title compound (476.3 mg).

MS (ESI) m/z 427.4 [M+H]$^+$

D: (R)—N-tert-Butyl-3-((4-(4-(3-(cyclopropylmethyl)ureido)-3-fluorobenzoyl)-2-methylpiperazin-1-yl)methyl)benzamide (R)-3-((4-(4-Amino-3-fluorobenzoyl)-2-methylpiperazin-1-yl)methyl)-N-tert-butylbenzamide (119 mg, 0.275 mmol) and 4-nitrophenol chloroformate (56 mg, 0.275 mmol) were combined and stirred in dichloromethane for 1 hour. Cyclopropanemethylamine (56.8 mg, 0.8 mmol, 0.0694 mL) was added and the reaction was stirred for a further 30 minutes. Water was added and the reaction mixture was flushed through a hydrophobic frit. The organic phase was concentrated under reduced pressure and purified by basic reverse phase HPLC to afford the title compound (19.8 mg). MS (ES) m/z 524.7 [M+H]+

Example 34

(S)—N-tert-Butyl-3-((4-(3-fluoro-4-(3-isobutylureido)benzoyl)-2-isopropylpiperazin-1-yl)methyl)benzamide

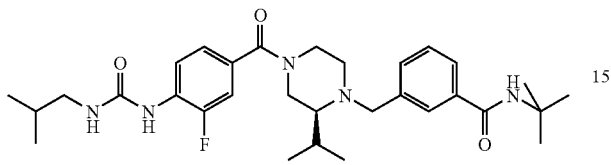

A: (S)-(4-Amino-3-fluorophenyl)(3-isopropylpiperazin-1-yl)methanone

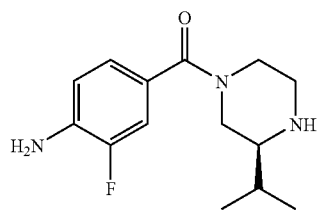

1-Propanephosphonic acid cyclic anhydride (1.752 mmol. 1.043 ml, 1115 mg) was added to a solution of (S)-tert-butyl 2-isopropylpiperazine-1-carboxylate (0.876 mmol, 200 mg), 4-amino-3-fluorobenzoic acid (0.876 mmol, 136 mg) and triethylamine (1.752 mmol, 0.244 ml, 177 mg) in dichloromethane and stirred at room temperature for 2 hours. After this time, ethyl acetate (100 mL) was then added to the reaction. The organic mixture was washed with saturated sodium hydrogen carbonate, water, dried over sodium sulphate and concentrated under vacuum. The residue was then dissolved in dichloromethane (5 ml) and trifluoroacetic acid (17.52 mmol, 1997 mg) added. The resultant solution was allowed to stand at room temperature overnight. The reaction was concentrated under vacuum and purified by strong cation exchange chromatography to give the title compound (200 mg) as a clear oil. MS (ESI) m/z 266.3 [M+H]+

B: (S)-3-((4-(4-Amino-3-fluorobenzoyl)-2-isopropylpiperazin-1-yl)methyl)-N-tert-butylbenzamide

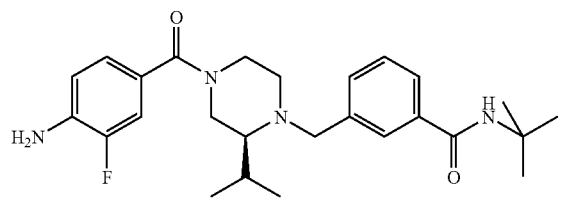

(S)-(4-Amino-3-fluorophenyl)(3-isopropylpiperazin-1-yl)methanone (0.754 mmol, 200 mg), N-tert-butyl-3-(chloromethyl)benzamide (0,754 mmol, 170 mg), potassium carbonate (1.508 mmol, 208 mg) and sodium iodide (0.075 mmol, 11.30 mg) were dissolved in acetonitrile (20 mL) and heated at reflux for 3 hours. The reaction was concentrated under vacuum and the crude material dissolved in ethyl acetate and washed with water, dried over sodium sulphate and concentration under vacuum. The crude residue was then purified by column chromatography (eluting with dichloromethane to dichloromethane/methanol (1% to 5%)) to give the title compound (160 mg) as an off white solid. MS (ESI) m/z 456.4 [M+H]+

C: (S)—N-tert-Butyl-3-((4-(3-fluoro-4-(3-isobutylureido)benzoyl)-2-isopropylpiperazin-1-yl)methyl)benzamide To a stirred solution of (S)-3-((4-(4-amino-3-fluorobenzoyl)-2-isopropylpiperazin-1-yl)methyl)-N-tert-butylbenzamide (40 mg, 0.088 mmol) in dichloromethane (2 mL) at room temperature was added 4-nitrophenyl chloroformate (18.62 mg, 0.092 mmol). The reaction mixture was stirred for 1 hour before the addition of isobutylamine (6.44 mg, 0.088 mmol). After 2 hours stirring, the reaction mixture was applied to a silica carbonate column (2 g). The eluant was concentrated under vacuum and redissolved in methanol. Purification by HPLC gave the title compound (3 mg). MS (ESI) m/z 554.3 [M+H]+

Example 35

N-tert-Butyl-3-((4-(4-(3-(cyclopropylmethyl)ureido)-3-fluorobenzoyl)-2-(fluoromethyl)piperazin-1-y)methyl)benzamide

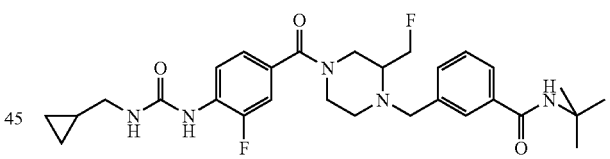

A: (3-Fluoro-4-nitrophenyl)(3-(fluoromethyl)piperazin-1-yl)methanone

A stirred suspension of 3-fluoro-4-nitrobenzoic acid (2 g, 10.8 mmol) in dichloromethane (30 mL) was cooled to 0° C. (ice/water bath). Oxalylchloride (1.648 g, 12.97 mmol) was added followed by N-methylpyrrolidinone (1 mL) to achieve a solution. The reaction mixture was stirred at 0° C. for 1 hour and then was concentrated under reduced pressure. The residue was azeotroped with dichloromethane (×3). The residue was redissolved in dichloromethane (20 mL) and cooled to 0° C. before the addition of triethylamine (64.8 mmol, 6.56 g) and 1-(fluoromethyl)piperazine dihydrochloride (10.8 mmol, 2.064 g). The reaction mixture was allowed to warm to room temperature and stir for 1 hour before being applied to a strong cation exchange column. The crude product was released from the column using 2M ammonia in methanol and purified using silica chromatography (4% methanol/dichloromethane) to give the title compound (444 mg). MS (ESI) m/z 286.4 [M+H]+

B: N-tert-Butyl-3-((4-(3-fluoro-4-nitrobenzoyl)-2-(fluoromethyl)piperazin-1-yl)methyl)benzamide

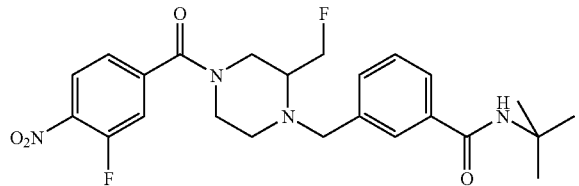

A stirred mixture of (3-fluoro-4-nitrophenyl)(3-(fluoromethyl)piperazin-1-yl)methanone (456 mg, 1.6 mmol), N-tert-butyl-3-(chloromethyl)benzamide (361 mg, 1.6 mmol), triethylamine (3.1 mmol, 341 mg) and sodium iodide (1.6 mmol, 240 mg) in acetonitrile (10 mL) was heated to 60° C. for several hours. The reaction was concentrated under reduced pressure. The residue was then dissolved in dichloromethane and extracted with water (×3). The organic phase was dried (sodium sulfate) and concentrated under vacuum. The crude material was purified using silica chromatography to give the title compound (435 mg). MS (ESI) m/z 475.7[M+H]+

C: 3-((4-(4-Amino-3-fluorobenzoyl)-2-(fluoromethyl)piperazin-1-yl)methyl)-N-tert-butylbenzamide

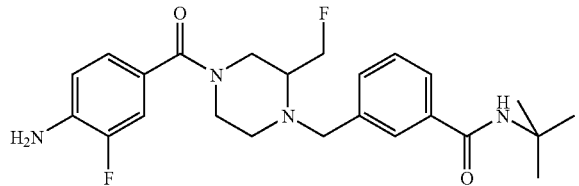

N-tert-butyl-3-((4-(3-fluoro-4-nitrobenzoyl)-2-(fluoromethyl)piperazin-1-yl)methyl)benzamide (435 mg, 0.92 mmol), iron powder (558 mg, 10 mmol) and 1M hydrochloric acid (1.5 mL, 1.5 mmol) were stirred in isopropyl alcohol (30 mL) for 1 hour. The reaction was concentrated under reduced pressure and the residue partitioned between dichloromethane and water. The organic layer was separated, dried (sodium sulfate) and concentrated under reduced pressure. The crude product was purified using silica chromatography to give the title compound (150 mg). MS (ESI) m/z 445.6 [M+H]+

D: N-tert-Butyl-3-((4-(4-(3-(cyclopropylmethyl)ureido)-3-fluorobenzoyl)-2-(fluoromethyl)piperazin-1-yl) methyl)benzamide To a solution of 3-((4-(4-amino-3-fluorobenzoyl)-2-(fluoromethyl)piperazin-1-yl)-methyl)-N-tert-butylbenzamide (150 mg, 0.34 mmol) in dichloromethane (4 mL) at room temperature was added 4-nitrophenyl chloroformate (71.4 mg, 0.354 mmol). The reaction mixture was stirred at room temperature for 1 hour before the addition of cyclopropanemethylamine (150 μL). The mixture was stirred at room temperature overnight before being applied to a silica carbonate column. The eluant was concentrated under reduced pressure and redissolved in methanol. Purification by basic reverse phase HPLC gave the title compound (2 mg), MS (ESI) m/z 542.5 [M+H]+

Example 36

N-tert-Butyl-3-((4-(4-(3-cyclobutylureido)-3-fluorobenzoyl)-2,2-dimethylpiperazin-1-yl)methyl)benzamide

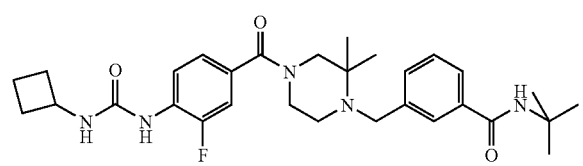

A: (4-Amino-3-fluorophenyl)(3,3-dimethylpiperazin-1-yl)methanone

Step 1: To tert-butyl 2,2-dimethylpiperazine-1-carboxylate (0.902 mmol, 0.193 g) in dichloro-methane (5 mL) was added 4-amino-3-fluorobenzoic acid (0.902 mmol, 0.14 g), and triethylamine (1.805 mmol, 0.252 mL, 0.183 g). To this mixture was added 1-propanephosphonic acid cyclic anhydride (1.805 mmol, 1.074 mL, 1.149 g, 50% solution in ethyl acetate). After 2 hours stirring, ethyl acetate was added and the organic mixture was washed with saturated sodium hydrogen carbonate, water, and saturated sodium chloride. The organic layer was dried with sodium sulfate, filtered and concentrated under vacuum to give the intermediate tert-butyl 4-(4-amino-3-fluorobenzoyl)-2,2-dimethylpiperazine-1-carboxylate (264 mg).

Step 2: To a stirred mixture of tert-butyl 4-(4-amino-3-fluorobenzoyl)-2,2-dimethylpiperazine-1-carboxylate (0.569 mmol, 200 mg) in dichloromethane (2 mL) was added trifluoroacetic acid (10.10 mmol, 0.75 mL, 1151 mg). After 1 hour stirring, the reaction was concentrated under reduced pressure. The residue was taken up in dichloromethane/methanol and loaded on to strong cation exchange column (5 g) which was washed with dichloromethane/methanol. The product was eluted from the column with 2M ammonia in methanol. The organic phase was concentrated under vacuum to yield the title compound (131 mg). MS (ESI) m/z 252.3 [M+H]+

B: 3-((4-(4-Amino-3-fluorobenzoyl)-2,2-dimethylpiperazin-1-yl)methyl)-N-tert-butylbenzamide

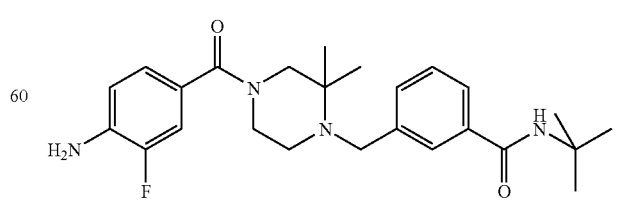

To (4-amino-3-fluorophenyl)(3,3-dimethylpiperazin-1-yl)methanone (0.521 mmol, 131 mg) in acetonitrile (5.213 mL)

was added N-tert-butyl-3-(chloromethyl)benzamide (0.573 mmol, 129 mg), and triethylamine (1.040 mmol, 145 µl, 105 mg). A catalytic amount of sodium iodide was added. The mixture was heated to reflux for 3 hours. The mixture was allowed to cool and ethyl acetate was added. The organic mixture was washed with water, dried with sodium sulfate, filtered and concentrated under vacuum. The residue was purified by silica chromatography (eluting with 5% methanol in dichloromethane) to yield the title compound (90 mg). MS (ESI) m/z 441.4 [M+H]$^+$ C: N-tert-Butyl-3-((4-(4-(3-cyclobutylureido)-3-fluorobenzoyl)-2,2-dimethylpiperazin-1-yl)methyl) benzamide To 3-((4-(4-amino-3-fluorobenzoyl)-2,2-dimethylpiperazin-1-yl)methyl)-N-tert-butylbenzamide (0.1 mmol, 45 mg) in dichloromethane (1.5 mL) was added 4-nitrophenyl chloroformate (0.11 mmol, 23 mg). The mixture was allowed to stir for 2 hours before the addition of cyclobutylamine (1.757 mmol, 125 mg, 150 µl). The mixture was allowed to stir for a further 16 hours before being concentrated under vacuum and purified by acidic reverse phase HPLC. The free base of the product was obtained using strong cation exchange column chromatography. This material was lyophilised to yield the title compound (16 mg).
MS (ESI) m/z 538.7 [M+H]$^+$ Example 37

N-tert-Butyl-3-(1-(4-(4-(3-cyclobutylureido)-3-fluorobenzoyl)piperazin-1-yl)-2-methylpropyl)benzamide

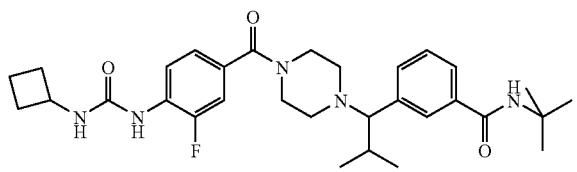

A: 3-(1-Hydroxy-2-methylpropyl)benzonitrile

15% Isopropyl magnesium bromide in diethyl ether (23.5 mL, 24.0 mmol) was added to a stirred solution of 3-formylbenzonitrile (2.62 mg, 20.0 mmol) in dry tetrahydrofuran (18 mL), at 0° C. under a nitrogen atmosphere. After stirring at 0° C. for 1 hour, then at room temperature for 2 hours, the mixture was partitioned between ethyl acetate and 1M hydrochloric acid. The aqueous layer was extracted with ethyl acetate and the combined organic layers were washed with brine, dried over sodium sulfate and concentrated under vacuum. The residue was purified with silica column chromatography (eluting with 9% to 25% ethyl acetate in heptane) to afford the title compound (1.164 g).
$^1$H NMR (CDCl$_3$, 400 MHz): δ 0.85 (3H, d), 0.95 (3H, d), 1.95 (1H, septet), 4.44-4.49 (1H, m), 7.44 (1H, t), 7.53-7.58 (2H, m), 7.63 (1H, s).

B: 3-(1Hydroxy-2-methylpropyl)benzoic Acid

A mixture of 3-(1-hydroxy-2-methylpropyl)benzonitrile (1.16 g, 6.62 mmol) and 10M potassium hydroxide (2.40 mL) in ethanol (10.0 mL) was subjected to microwave irradiation at 160° C. for 10 minutes. The mixture was concentrated under vacuum and partitioned between diethyl ether and water. The aqueous layer was acidified with 5M hydrochloric acid and extracted with dichloromethane. The combined dichloromethane extracts were washed with brine, dried over sodium sulfate and concentrated under vacuum to afford the title compound (1.072 g).
$^1$H NMR (CDCl$_3$, 400 MHz): δ 0.84 (3H, d), 0.99 (3H, d), 1.99 (1H, septet), 4.48 (1H, d), 7.46 (1H, t), 7.59 (1H, d), 8.01 (1H, d), 8.05 (1H, s).

C: N-tert-Butyl-3-(1-hydroxy-2-methylpropyl)benzamide

A mixture of 3-(1-hydroxy-2-methylpropyl)benzoic acid (677 mg, 3.49 mmol), O-(7-azabenzotriazol-1-yl)-N,N,N,N-tetramethyl uronium hexafluorophosphate (1.73 g, 4.54 mmol), N-ethyl-N-isopropylpropan-2-amine (1.21 mL, 6.97 mmol) and tert-butylamine (510 mg, 6.97 mmol) in N,N-dimethylformamide (12.0 mL) was subjected to microwave irradiation at 100° C. for 10 minutes. The reaction mixture was concentrated under vacuum and purified with silica column chromatography (eluting with 9% to 33% ethyl acetate in heptane) to afford the title compound (718 mg). MS (ESI) m/z 250.4 [M+H]$^+$ D: tert-Butyl 4-(1-(3-(tert-butylcarbamoyl)phenyl)-2-methylpropyl)piperazine-1-carboxylate

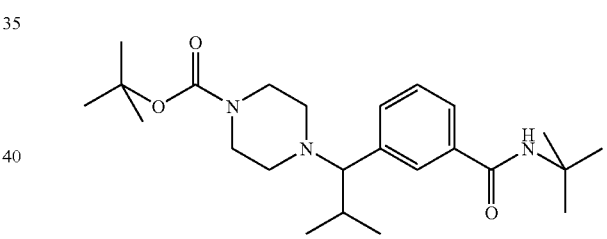

Step 1: A solution of methanesulfonyl chloride (165 mg, 1.44 mmol) in dichloromethane (2.0 mL) was added to a stirred solution of N-tert-butyl-3-(1-hydroxy-2-methylpropyl)benzamide (300 mg, 1.20 mmol) in dichloromethane (8.0 mL). After 1.5 hours stirring, the mixture was partitioned between dichloromethane and aqueous sodium hydrogen carbonate solution. The aqueous layer was extracted with dichloromethane and the combined organic layers were washed with brine, dried over sodium sulfate and concentrated under vacuum to afford the intermediate 1-(3-(tert-butylcarbamoyl) phenyl)propyl methanesulfonate.

Step 2: A solution of 1-(3-(tert-butylcarbamoyl)phenyl) propyl methanesulfonate, tert-butyl piperazine-1-carboxylate (447 mg, 2.40 mmol) and N-ethyl-N-isopropylpropan-2-amine (0.623 mL, 3.60 mmol) in N,N-dimethylformamide (8.0 mL) was stirred at 70° C. for 4 hours, then subjected to microwave Irradiation at 160° C. for 10 minutes. The reaction mixture was concentrated under vacuum, treated with strong cation exchange column chromatography and purified with silica column chromatography (eluting with 20% to 66% ethyl acetate in heptane) to afford the title compound (16 mg).
MS (ESI) m/z 418.5 [M+H]$^+$

E: N-tert-Butyl-3-(2-methyl-1-(piperazin-1-yl)propyl)benzamide

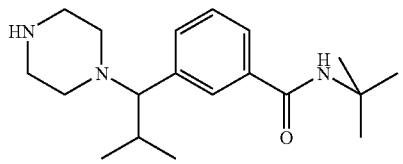

A mixture of tert-butyl 4-(1-(3-(tert-butylcarbamoyl)phenyl)-2-methylpropyl)piperazine-1-carboxylate (24 mg, 0,057 mmol) and 5M hydrochloric acid (0.20 mL) in 1,4-dioxane (2.0 mL) was stirred at 80° C. for 30 minutes. The reaction mixture was concentrated under vacuum and treated with strong cation exchange column chromatography to afford the title compound (13.6 mg).

MS (ESI) m/z 318.3 [M+H]+

F: 3-(1-(4-(4-Amino-3-fluorobenzoyl)piperazin-1-yl)-2-methylpropyl)-N-tert-butylbenzamide

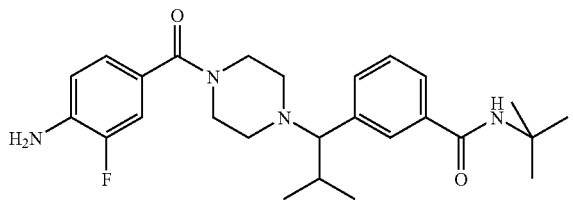

A mixture of N-tert-butyl-3-(2-methyl-1-(piperazin-1-yl)propyl)benzamide (13.6 mg, 0.043 mmol), 4-amino-3-fluorobenzoic acid (10 mg, 0.065 mmol), N-ethyl-N-isopropylpropan-2-amine (11 mg, 0.086 mmol) and 1-propanephosphonic acid cyclic anhydride (55 mg, 0.086 mmol, 50% solution in ethyl acetate) in dichloromethane (2.0 mL) was stirred at room temperature for 2 hours. The mixture was treated with strong cation exchange column chromatography and purified with silica column chromatography (eluting with 33% ethyl acetate in heptane then 66% ethyl acetate in heptane) to afford the title compound (11.8 mg).

MS (ESI) m/z 455.5 [M+H]+

G: N-tert-Butyl-3-(1-(4-(4-(3-cyclobutylureido)3-fluorobenzoyl)piperazin-1-yl)-2-methylpropyl)benzamide A mixture of 3-(1-(4-(4-amino-3-fluorobenzoyl)piperazin-1-yl)-2-methylpropyl)-N-tert-butylbenzamide (3.0 mg, 0.0066 mmol) and 4-nitrophenylchloroformate (1.5 mg, 0.0073 mmol) in dichloromethane (1.0 mL) was stirred at room temperature for 1 hour. Cycloprobutylamine (1.0 mg, 0.013 mmol) was added and the mixture was stirred at room temperature for 2 hours. The mixture was treated with strong cation exchange column chromatography and purified by HPLC to afford the title compound (1,6 mg).

MS (ESI) m/z 552.8 [M+H]+

Example 38

1-(4-(1-(5-(tert-Butylcarbamoyl)-2-methoxybenzyl)piperazine-4-carbonyl)phenyl)-3-phenylurea 2,2,2-trifluoroacetate

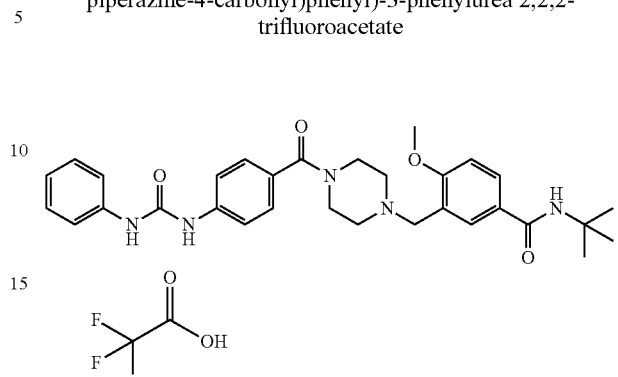

A: tert-Butyl 4-(4-(3-phenylureido)benzoyl)piperazine-1-carboxylate

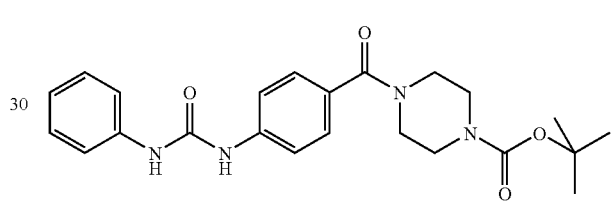

To a solution of 4-(3-phenylureido)benzoic acid (13.5 g, 52.68 mmol) in acetonitrile (250 mL) at room temperature was added tert-butyl piperazine-1-carboxylate (11.8 g, 63.22 mmol), 1H-benzo[d][1,2,3]triazol-1-ol (21.1 g, 156.5 mmol, HOBT) and 1-ethyl-3-(3-dimethylaminopropyl)carbodiimide hydrochloride (30 g, 156.5 mmol, EDCl). The mixture was stirred at reflux temperature for 16 hours and was then concentrated under vacuum. The residue was submitted to silica chromatography (0-5% ethyl acetate in n-hexanes as eluant) to give the title compound (15.0 g). MS (ESI) m/z 425.1 [M+H]+

B: 1-Phenyl-3-(4-(piperazine-1-carbonyl)phenyl) urea 2,2,2-trifluoroacetate

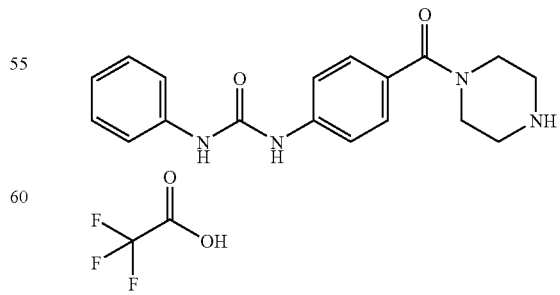

tert-Butyl 4-(4-(3-phenylureido)benzoyl)piperazine-1-carboxylate (15.0 g, 35.34 mmol) was stirred with 50% trifluoroacetic acid in dichloromethane (200 ml) at room temperature for 1 hour. The reaction was concentrated under vacuum and then dryed overnight on high vacuum to afford the title compound (15.5 g). MS (ESI) m/z 325.0 [M+H]$^+$ C; Methyl 4-methoxy-3-((4-(4-(3-phenylureido)benzoyl)piperazin-1-yl)methyl)benzoate

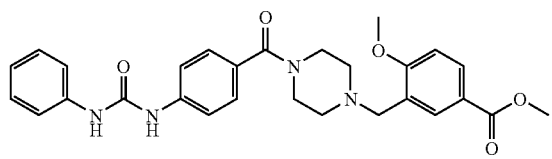

1-Phenyl-3-(4-(piperazin-1-carbonyl)phenyl)urea (439 mg, 1.0 mmol) was stirred in acetonitrile (8 mL) at room temperature for 1 hour, N-Ethyl-N-isopropylpropan-2-amine (697 µl, 4 mmol) was added, followed by a solution of methyl 3-(chloromethyl)4-methoxy-benzoate (215 mg, 1.0 mmol) in acetonitrile (5 mL). The mixture was heated to 45° C. and stirred overnight. The mixture was concentrated under vacuum, diluted with dichloromethane (40 mL) and washed with saturated aqueous ammonium chloride (25 mL) and saturated aqueous sodium chloride (25 mL). The organic phase was dried on magnesium sulfate, filtered and concentrated under vacuum. The residue was submitted to silica chromatography (0-10% methanol in dichloromethane as eluant) to give the title compound (216 mg). MS (ESI) m/z 503.1 [M+H]$^+$ D: 4-Methoxy-3-((4-(4-(3-phenylureido)benzoyl)piperazin-1-yl)methyl)benzoic Acid

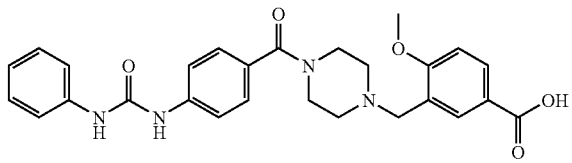

Methyl 4-methoxy-3-((4-(4-(3-phenylureido)benzoyl)piperazin-1-yl)methyl)benzoate (216 mg, 0.43 mmol) was dissolved in methanol (20 mL) at room temperature. Lithium hydroxide (51.5 mg, 2.15 mmol) was added, followed by water (1 mL). The mixture was stirred at 45° C. overnight and concentrated under vacuum. The residue was dissolved in water (15 mL) and brought to pH ~3 with 1M aqueous hydrochloric acid. The mixture was extracted with ethyl acetate (×2) and with dichloromethane (×2). The combined organic phases were dried on magnesium sulfate, filtered and concentrated under vacuum. The residue was submitted to silica chromatography (0-10% methanol in dichloromethane as eluant) to give the title compound (78 mg). MS (ESI) m/z 489.1 [M+H]$^+$ E: 1-(4-(1-(5-(tert-Butylcarbamoyl)-2-methoxybenzyl)piperazine-4-carbonyl)phenyl)-3-phenylurea 2,2,2-trifluoroacetate 4-Methoxy-3-((4-(4-(3-phenylureido)benzoyl)piperazin-1-yl)methyl)benzoic acid (10 mg, 20.5 µmol) was dissolved in N,N-dimethylformamide (1 mL) at room temperature. Tert-Butylamine (10.8 µL, 102 µmol) was added, followed by O-(7-azabenzotriazol-1-yl)-N,N,N,N-tetramethyl uronium hexafluorophosphate (10 mg, 26.3 µmol, HATU). The mixture was stirred at room temperature overnight and was then concentrated under vacuum. The residue was diluted with dichloromethane (15 mL), washed with saturated aqueous ammonium chloride and saturated aqueous sodium chloride. The organic phase was dried on magnesium sulfate, filtered and concentrated under vacuum. The resulting residue was purified on acidic reverse phase HPLC to give the title compound (10.2 mg), MS (ESI) m/z 544.1 [M+H]$^+$ Example 39

N-tert-Butyl-3-((4-(4-(3-cyclobutylureido)benzoyl)piperazin-1-yl)methyl)-2-fluorobenzamide

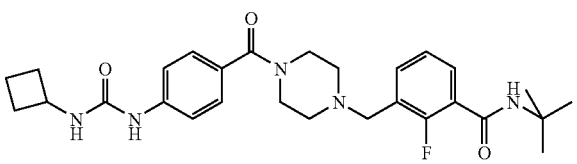

A: N-tert-Butyl-2-fluoro-3-methylbenzamide

To a stirred solution of 2-fluoro-3-methylbenzoic acid (8.76 mmol, 1.35 g), 2-methylpropan-2-amine (9.43 mmol, 1 mL, 0.690 g) and triethylamine (28.7 mmol, 4 mL, 2.90 g) in dichloromethane (20 mL) was added 1-propanephosphonic acid cyclic anhydride (13.50 mmol, 8 mL, 8.59 g, 50% solution in ethyl acetate). The reaction was stirred for 2 hours and diluted with dichloromethane and aqueous sodium hydrogen carbonate. The organic layer was separated, dried and concentrated under reduced pressure to yield the title compound (1 g).
MS (ESI) m/z 210.1 [M+H]$^+$ B: 3-(Bromomethyl)-N-tert-butyl-2:fluorobenzamide Benzoyl peroxide (0.048 mmol, 11.58 mg), N-bromosuccinimide (5.02 mmol, 893 mg) and N-tert-butyl-2-fluoro-3-methylbenzamide (4.78 mmol, 1000 mg) were stirred together in benzene (12 mL) at reflux for 16 hours. After this time the reaction was allowed to cool and the reaction was concentrated under reduced pressure. Dichloromethane was added and the solution was extracted with a saturated ammonium chloride solution. The organic phase was dried with sodium sulfate and the volatiles were removed under reduced pressure. Purification by silica chromatography gave the title compound (105 mg).
$^1$H NMR (CD$_3$OD, 400 MHz): δ 1.44 (9H, s), 4.60 (2H, s), 7.20 (1H, m), 7.55 (2H, m).

C: N-tert-Butyl-3-((4-(4-(3-cyclobutylureido)benzoyl)piperazin-1-yl)methyl)-2-fluorobenzamide A stirred mixture of 3-(bromomethyl)-N-tert-butyl-2-fluorobenzamide (0.36 mmol, 105 mg), 1-cyclobutyl-3-(4-(piperazine-1-carbonyl)phenyl)urea (0.33 mmol, 620 mg) and triethylamine (2.5 mmol, 0.35 mL, 253 mg) in tetrahydrofuran (2 mL) was heated to 70° C. for 16 hours. After this time the volatiles were removed under vacuum. The residue was purified by strong cation exchange chromatography and basic reverse phase HPLC to yield the title compound (74 mg). MS (ESI) m/z 510.6 [M+H]+

Example 40

N-tert-Butyl-2-fluoro-3-((4-(4-(3-neopentylureido)benzoyl)piperazin-1-yl)methyl)benzamide

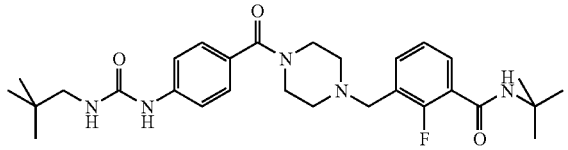

A: tert-Butyl 4-(3-(tert-butylcarbamoyl)-2-fluorobenzyl)piperazine-1-carboxylate

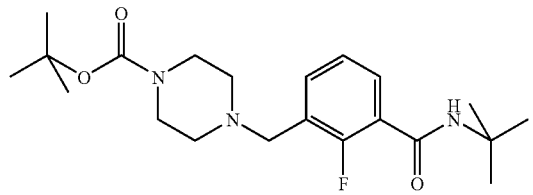

To a stirred mixture of tert-butyl piperazine-1-carboxylate (3.53 mmol, 658 mg) in acetonitrile (30 mL) was added 3-(bromomethyl)-N-tert-butyl-2-fluorobenzamide (3.21 mmol, 925 mg), sodium iodide (0.321 mmol, 48.1 mg) and triethylamine (4.82 mmol, 0.671 ml, 487 mg). The reaction mixture was stirred at reflux for 4 hours and then was diluted with water and ethyl acetate. The organic layer was separated, dried and concentrated under reduced pressure. Purification by silica chromatography (eluting with 5% methanol/dichloromethane) gave the title compound (1 g). MS (ESI) m/z 394.1 [M+H]+

B: N-tert-Butyl-2-fluoro-3-(piperazin-1-ylmethyl)benzamide

To a stirred mixture of tert-butyl 4-(3-(tert-butylcarbamoyl)-2-fluorobenzyl)piperazine-1-carboxylate (2.54 mmol, 1 g) in dichloromethane at room temperature was added trifluoro-acetic acid (53.9 mmol, 4 mL, 6.14 g). After 3 hours stirring the reaction was concentrated under reduced pressure. The residue was taken up in dichloromethane/methanol and loaded on to strong cation exchange column (10 g) and washed with dichloromethane/methanol. Elution of the column with 2M ammonia in methanol gave the title compound (636 mg). MS (ESI) m/z 294.4 [M+H]+

C: 3-((4-(4-Aminobenzoyl)piperazin-1-yl)methyl)-N-tert-butyl-2-fluorobenzamide

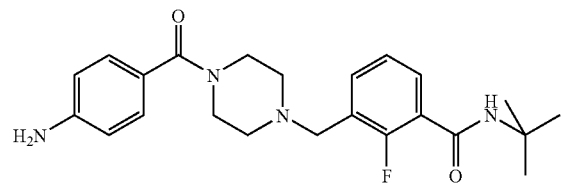

N-tert-butyl-2-fluoro-3-(piperazin-1-ylmethyl)benzamide (0.648 mmol, 190 mg). 4-amino-benzoic acid (0.648 mmol, 89 mg) and triethylamine (2.59 mmol, 0.361 mL, 262 mg) were dissolved in dichloromethane (6.476 mL). 1-Propanephosphonic acid cyclic anhydride (1.295 mmol, 0.767 mL, 824 mg, 50% solution in ethyl acetate) was added and the reaction mixture was stirred for 2 hours. Ethyl acetate was added and the organic phase was washed with water, sodium hydrogen carbonate, brine and dried with sodium sulfate. The organic phase was concentrated under reduced pressure to yield the title compound (146 mg). MS (ESI) m/z 413.4 [M+H]+

D: N-tert-Butyl-2-fluoro-3-((r-(4-(3-neopentylureido)benzoyl)piperazin-1-yl)methyl)benzamide 3-((4-(4-Aminobenzoyl)piperazin-1-yl)methyl)-N-tert-butyl-2-fluorobenzamide (0.109 mmol, 45 mg) and 4-nitrophenyl chloroformate (0.120 mmol, 24.19 mg) were combined in dichloromethane (1 ml). The reaction mixture was stirred for 1 hour before the addition of 2,2-dimethylpropan-1-amine (0.855 mmol, 100 µl, 74.5 mg). After 30 minutes stirring, the reaction was concentrated under vacuum. The residue was taken up in dichloromethane/methanol and loaded on to strong cation exchange column (2 g) and washed with dichloromethane/methanol. Elution of the column with 2M ammonia in methanol gave the title compound (52 mg). MS (ESI) m/z 526.2 [M+H]+

Example 41

N-tert-Butyl-3-((4-(4-(3-cyclobutylureido)benzoyl)piperazin-1-yl)methyl)-2,6-difluorobenzamide

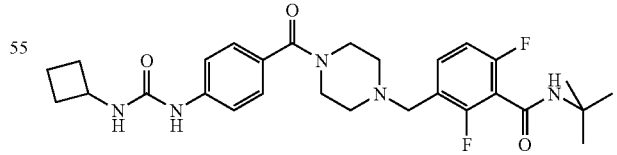

A: N-tert-Butyl-2,6-difluoro-3-methylbenzamide

To a stirred solution of 2,6-difluoro-3-methylbenzoic acid (8.75 mmol, 1.5 g), 2-methylpropan-2-amine (9.43 mmol, 1 mL, 0.690 g) and triethylamine (28.7 mmol, 4 mL, 2.90 g) in dichloromethane (20 mL) was added 1-propanephosphonic acid cyclic anhydride (13.50 mmol, 8 mL, 8.59 g, 50% solution In ethyl acetate). The reaction was stirred for 2 hours before being diluted with dichloromethane and aqueous sodium hydrogen carbonate. The organic layer was separated, dried and concentrated under vacuum to yield the title compound (1.1 g). MS (ESI) m/z 228.4 [M+H]+

B: 3-(Bromomethyl)-N-tert-butyl-2,6-difluorobenzamide

Benzoyl peroxide (0.048 mmol, 11.58 mg), N-bromosuccinimide (5.02 mmol, 893 mg) and N-tert-butyl-2-fluoro-3-methylbenzamide (4.78 mmol, 1,1 g) were stirred together in benzene (12 mL) at reflux for 16 hours. After this time the reaction was allowed to cool and was concentrated under reduced pressure. Dichloromethane was added and the solution was extracted with a saturated ammonium chloride solution. The organic phase was dried with sodium sulfate and the reaction was concentrated under reduced pressure. Purification by silica chromatography gave the title compound (111 mg).

$^1$H NMR (CD$_3$OD, 400 MHz): δ 1.43 (9H, s), 4.60 (2H, s), 7.00 (1H, m), 7.50 (1H, m).

C: N-tert-Butyl-3-((4-(4-(3-cyclobutylureido)benzoyl)piperazin-1-yl)methyl)-2,6-difluorobenzamide A stirred mixture of 3-(romomethyl)-N-tert-butyl-2,6-difluorobenzamide (0.36 mmol, 111 mg), 1-cyclobutyl-3-(4-(piperazine-1-carbonyl)phenyl)urea (0.33 mmol, 620 mg) and triethylamine (2.5 mmol, 0.35 ml, 253 mg) in tetrahydrofuran (2 mL) was heated at 70° C. for 16 hours. After this time the reaction was concentrated under vacuum. The residue was purified by strong cation exchange column chromatography and basic reverse phase HPLC to yield the title compound (60 mg).
MS (ESI) m/z 528.3 [M+H]+

Example 42

3((4-(4(3-(Cyclopropylmethyl)ureido)-3-fluorobenzoyl)piperazin-1-yl)methyl)-N-(furan-2-ylmethyl)benzamide 2,2,2-trifluoroacetate

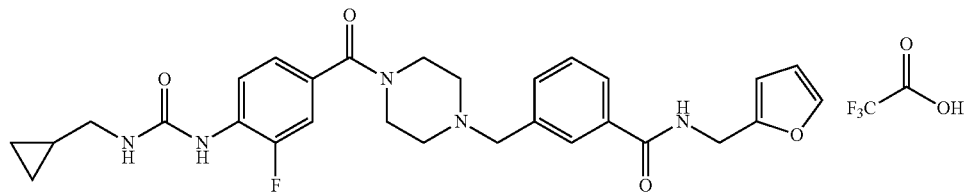

A mixture of 3-((4-(4-(3-(cyclopropylmethyl)ureido)-3-fluorobenzoyl)piperazin-1-yl)methyl)benzoic acid hydrochloride (300 mg, 0.434 mmol), furan-2-ylmethylamine (84 mg, 0.87 mmol), N-ethyl-N-isopropylpropan-2-amine (112 mg, 0.87 mmol) and O-(7-azabenzotriazol-1-yl)N,N,N,N-tetramethyl uronium hexafluorophosphate (214 mg, 0.564 mmol) in N,N-dimethylformamide (10 mL) was subjected to microwave irradiation at 100° C. for 10 minutes. The reaction mixture was treated with strong cation exchange column chromatography and purified with acidic reverse phase HPLC to afford the title compound (94.7 mg).
MS (ESI) m/z 534.5 [M+H]+

The following compounds were prepared in a similar manner:
42B: 3-((4-(4-(3-(Cyclopropylmethyl)ureido)-3-fluorobenzoyl)piperazin-1-yl)methyl)-N-(pentan-3-yl)benzamide 2,2,2-trifluoroacetate

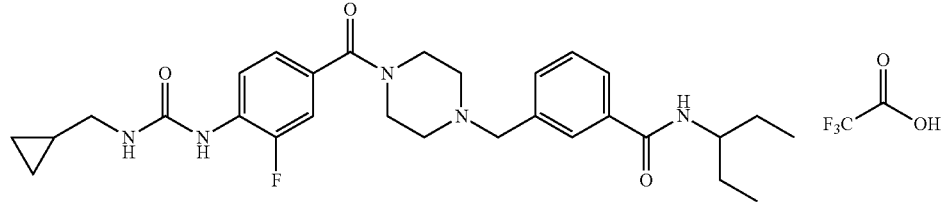

MS (ESI) m/z 524.75 [M+H]+

42C: N-Cyclohexyl-3-((4-(4-(3-(cyclopropylmethyl)ure-ido)-3-fluorobenzoyl)piperazin-1-yl)methyl)benzamide 2,2,2-trifluoroacetate

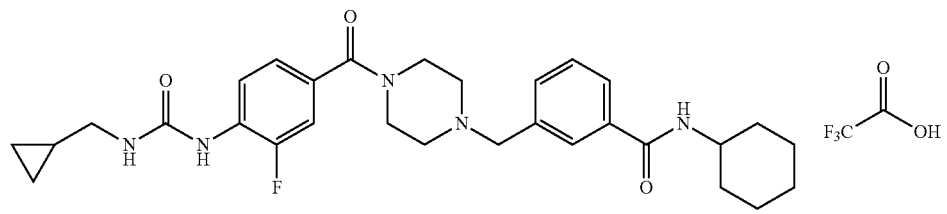

MS (ESI) m/z 536.7 [M+H]⁺

42D: 3-((4-(4-(3-(Cyclopropylmethyl)ureido)-3-fluorobenzoyl)piperazin-1-yl)methyl)-N-(pyridin-2-ylmethyl)benzamide bis(2,2,2-trifluoroacetate)

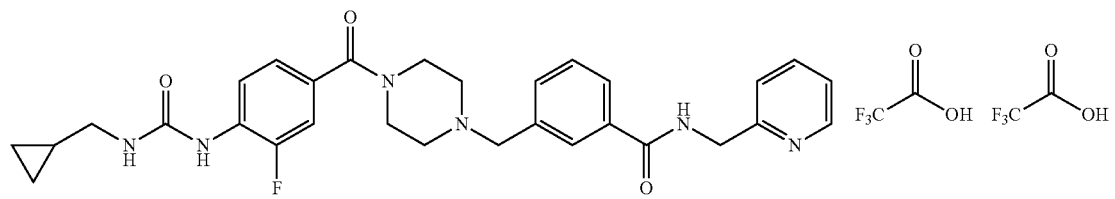

MS (ESI) m/z 555.5 [M+H]⁺

42E: 3-((4-(4-(3-(Cyclopropylmethyl)ureido)-3-fluorobenzoyl)piperazin-1-yl)methyl)-N-phenylbenzamide 2,2,2-trifluoroacetate

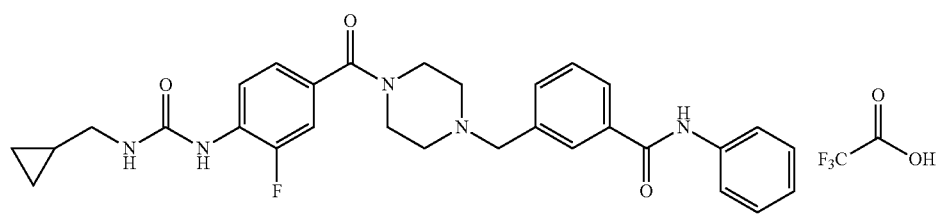

MS (ESI) m/z 530.5 [M+H]⁺

42F: 3-((4-(4-(3-(Cyclopropylmethyl)ureido)-3-fluorobenzoyl)piperazin-1-yl)methyl)-N-(214-difluorobenzyl)benzamide 2,2,2-trifluoroacetate

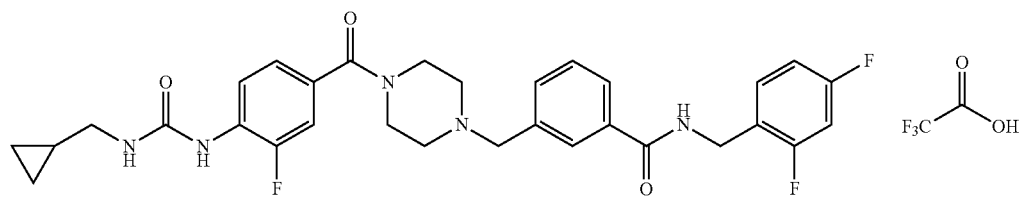

MS (ESI) m/z 580.3 [M+H]⁺

42G: N-(1-Cyanocyclopentyl)-3-((4-(4-(3-(cyclopropylmethyl)ureido)-3-fluorobenzoyl)piperazin-1-yl)methyl)benzamide

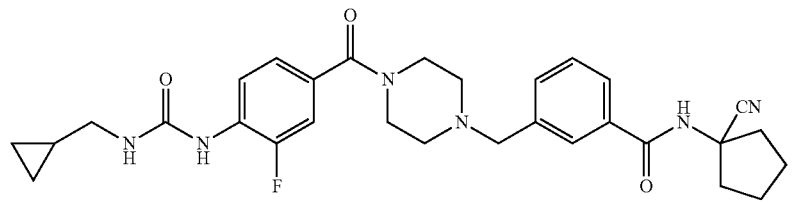

MS (ESI) m/z 547.5 [M+H]+

51M: 3-((4-(4-(3-(Cyclopropylmethyl)ureido)-3-fluorobenzoyl)piperazin-1-yl)methyl)-N-(2-methylbut-3-yn-2-yl)benzamide

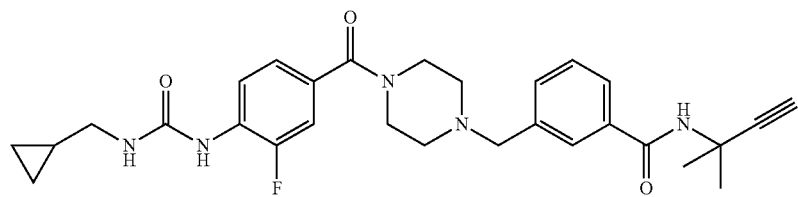

MS (ESI) m/z 520.5 [M+H]+

42H: N-(2-Cyanopropan-2-yl)-3-((4-(4-(3-(cyclopropylmethyl)ureido)-3-fluorobenzoyl)piperazin-1-yl)methyl)benzamide

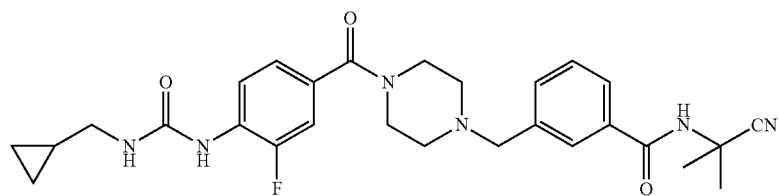

MS (ESI) m/z 521.3 [M+H]+

42I: 3-((4-(4-(3-(Cyclopropylmethyl)ureido)-3-fluorobenzoyl)piperazin-1-yl)methyl)-N-(2-cyclopropylpropan-2-yl)benzamide

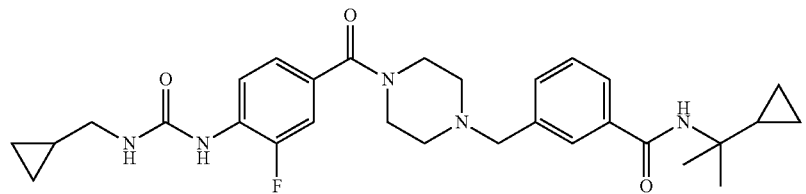

MS (ESI) m/z 536.5 [M+H]+

42J: trans-3-((4-(4-(3(Cyclopropylmethyl)ureido)-3-fluorobenzoyl)piperazin-1-yl)methyl)-N-(2-phenylcyclopropyl)benzamide

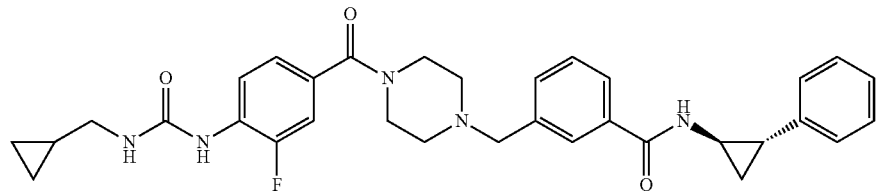

MS (ESI) m/z 570.5 [M+H]+

42K: 3-((4-(4-(3-(Cyclopropylmethyl)ureido)-3-fluorobenzoyl)piperazin-1-yl)methyl)-N-((5-methylisoxazol-3-yl)methyl)benzamide

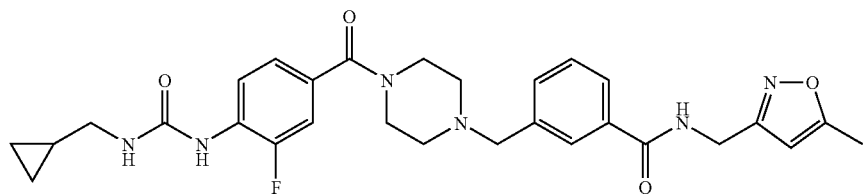

MS (ESI) m/z 549.3 [M+H]+

42L: 3-((4-(4-(3-(Cyclopropylmethyl)ureido)-3-fluorobenzoyl)piperazin-1-yl)methyl)-N-(tetrahydro-2H-pyran-4-yl)benzamide 2,2,2-trifluoroacetate

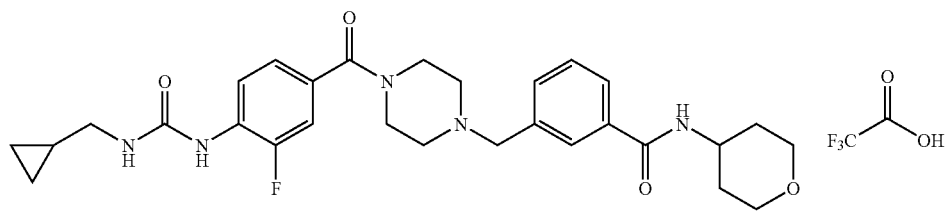

MS (ESI) m/z 538.7 [M+H]+

42M: 3-((4-(4-(3-(Cyclopropylmethyl)ureido)-3-fluorobenzoyl)piperazin-1-yl)methyl)-N-(thiazol-2-yl)benzamide 2,2,2-trifluoroacetate

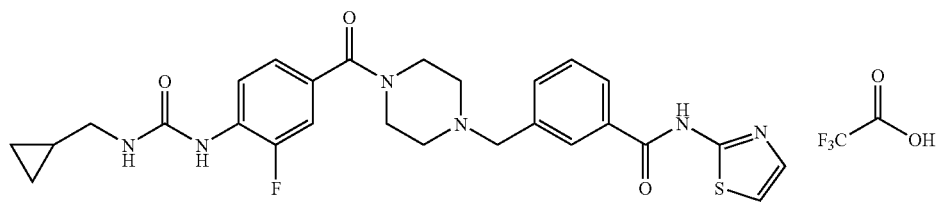

MS (ESI) m/z 537.5 [M+H]+

42N: N-(Cyano(phenyl)methyl)-3-((4-(4-(3-(cyclopropylmethyl)ureido)-3-fluorobenzoyl)piperazin-1-yl)methyl)benzamide

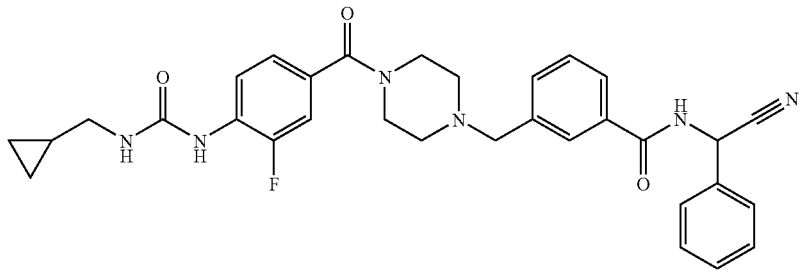

MS (ESI) m/z 569.5 [M+H]+

Example 43

1-(4-(1-(3-((1-(Hydroxymethyl)cyclopentyl)caramoyl)benzyl)piperazine-4-carbony)phenyl)-3-phenylurea 2,2,2-trifluoroacetate

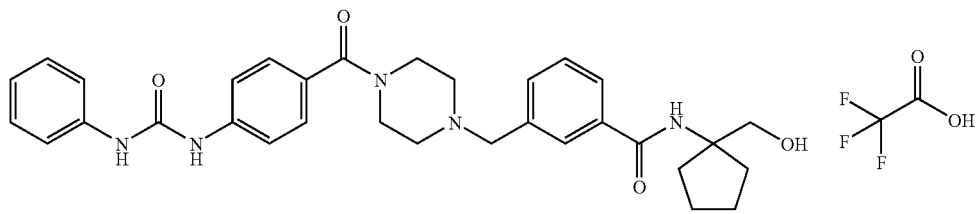

A: Methyl 3-(piperazin-1-ylmethyl)benzoate bis(2,2,2-trifluoroacetate)

B: Methyl 3-((4-(4-(3-phenylureido)benzoyl)piperazin-1-yl)methyl)benzoate

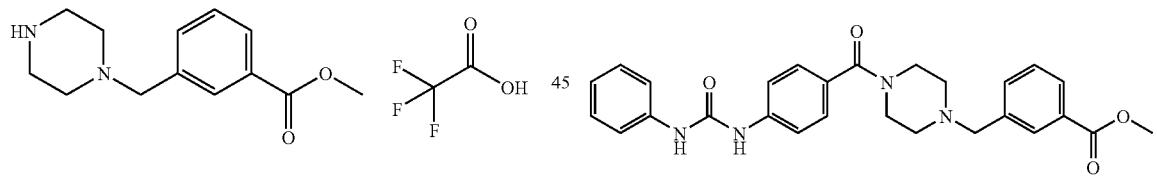

Tert-butyl 4-(3-(methoxycarbonyl)benzyl)piperazine-1-carboxylate (1.25 g, 3.74 mmol) was stirred with a 4/1 solution of dichloromethane/trifluoroacetic acid (20 mL) for 1 hour at room temperature. The solution was then concentrated under vacuum to afford the title compound (1.73 g). MS (ESI) m/z 235.1 [M+H]$^+$ To a solution of ethyl 4-(3-phenylureido)benzoate (1.00 g, 3.90 mmol) in N,N-dimethylform-amide (20 mL) was added methyl 3-(piperazin-1-ylmethyl)benzoate bis(2,2,2-trifluoroacetate) (1.25 g, 2.70 mmol), N-ethyl-N-isopropylpropan-2-amine (0.94 mL, 5.40 mmol), 1H-benzo[d][1,2,3]triazol-1-ol (0.40 g, 2.97 mmol, HOBT) and 1-ethyl-3-(3-dimethylaminopropyl)carbodiimide hydrochloride (0.57 g, 2,97 mmol, EDCl). The mixture was stirred overnight at room temperature and then concentrated under vacuum. The residue was taken up in ethyl acetate and washed with water (×2) and then saturated aqueous sodium chloride. The organic phase was dried on magnesium sulfate, filtered, concentrated under vacuum. Silica chromatography (10-40% ethyl acetate in n-hexanes) and recrystallisation from methanol gave the title compound (1.02 g).

MS (ESI) m/z 473.1 [M+H]$^+$

C: 3-((4-(4-(3-Phenylureido)benzoyl)piperazin-1-yl)methyl)benzoic Acid

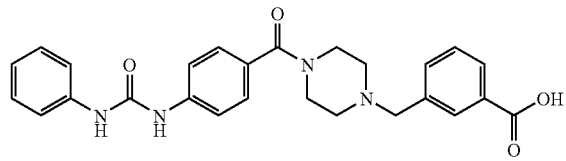

Methyl 3-((4-(4-(3-phenylureido)benzoyl)piperazin-1-yl)methyl)benzoate (0.47 g, 1 mmol) was suspended in a mixture of water (5 mL)/1,4-dioxane (15 mL) and treated with lithium hydroxide mono-hydrate (0.168 g, 4 mmol). The mixture was stirred at room temperature for 60 hours and was filtered over fluted paper. The filtrate was concentrated under vacuum and then acidified with 1M hydrochloric acid. The mixture was extracted with ethyl acetate (×4) and the combined organic layers were dried on magnesium sulfate, filtered and concentrated under vacuum to give the title compound (0.47 g).

MS (ESI) m/z 459.0 [M+H]$^+$

D: 1-(4-(1-(3-((1-(Hydroxymethyl)cyclopentyl)caramoyl)benzyl)piperazine-4-carbonyl)phenyl)-3-phenylurea 2,2,2-trifluoroacetate A mixture of 3-((4-(4-(3-phenylureido)benzoyl)piperazin-1-yl)methyl)benzoic acid (25 mg, 0.055 mmol), 1-amino-1-cyclopentanemethanol (18.8 mg, 0.163 mmol), O-(7-azabenzotriazol-1-yl)-N,N,N,N-tetramethyl uronium hexafluorophosphate (31 mg, 0.082 mmol) and N,N-dimethylformamide (0.2 mL) was stirred at room temperature overnight. The reaction mixture was diluted with methanol (2 mL) and purified by acidic reverse phase HPLC yielding the title compound (12.4 mg).

MS (ESI) m/z 556.1 [M+H]$^+$

The following compound was prepared in a similar manner:

43B: 1-(4-(1-(3-((2-Methoxyphenyl)carbamoyl)benzyl)piperazine-4-carbonyl)phenyl)-3-phenylurea 2,2,2-trifluoroacetate

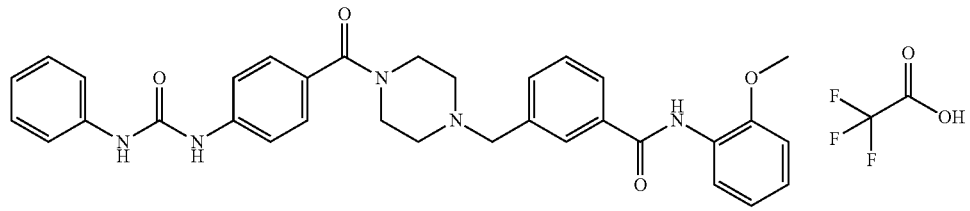

MS (ESI) m/z 564.1 [M+H]$^+$

Example 44

3-((4-(4-(3-Cyclobutylureido)benzoyl)piperazin-1-yl)methyl)-N-(1,1,1-trifluoro-2-methylpropan-2-yl)benzamide

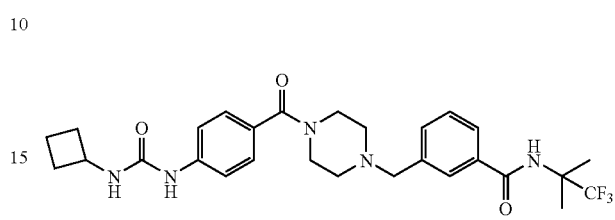

A: tert-Butyl 4-(4-(3-cyclobutylureido)benzoyl)piperazine-1-carboxylate

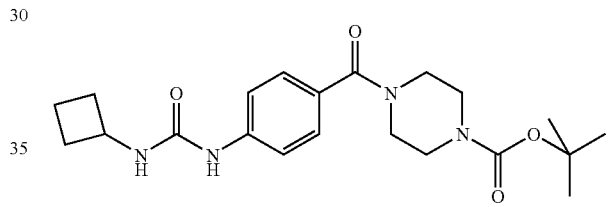

A flask was charged with 4-(3-cyclobutylureido)benzoic acid (51.3 mmol, 12.023 g), triethyl-amine (129 mmol, 18 mL, 13.07 g) and dichloromethane (75 mL) and cooled to 0° C. tert-Butyl piperazine-1-carboxylate (51.3 mmol, 9.56 g) was then added and the reagents were stirred together for 10 minutes at 0° C. before 1-propanephosphonic acid cyclic anhydride (64.2 mmol, 38.0 mL, 40.8 g, 50% solution in ethyl acetate) was slowly added. The reaction mixture was allowed to warm slowly to room temperature. After 5 hours stirring, the reaction was poured into a flask containing water (100 mL) and brine (20 ml). The mixture was then stirred and left to stand overnight. The resulting precipitate was collected by vacuum filtration, washed with cold water and dried under B:
1-Cyclobutyl-3-(4-(piperazine-carbonyl)phenyl)urea

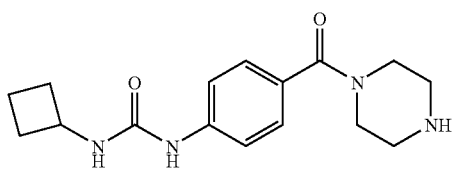

tert-Butyl 4-(4-(3-cyclobutylureido)benzoyl)piperazine-1-carboxylate (48.7 mmol, 19.6 g) was dissolved in a mixture of dichloromethane (125 ml) and acetonitrile (10 mL). After complete dissolution, trifluoroacetic acid (269 mmol, 20 mL, 30.7 g) was added over 10 minutes. The reaction was stirred until no trace of starting material remained. The reaction was neutralised with sodium hydrogen carbonate, filtered and concentrated under vacuum to generate a white solid. The desired product was isolated by continuous extraction of this material using soxhlet apparatus with dichloromethane as elutant. The organic phase was concentrated under vacuum to yield the title compound as a white powder (14.34 g). MS (ESI) m/z 303.5[M+H]$^+$ C: 3-(Chloromethyl)-N-(1,1,1-trifluoro-2-methylpropan-2-yl)benzamide 3-(Chloromethyl)benzoyl chloride (38.5 mmol, 5.48 mL, 7.29 g) was dissolved in dichloromethane (100 mL) and stirred. To this was added a mixture of 1,1,1-trifluoro-2-methylpropan-2-amine (39.3 mmol, 5 g) and triethylamine (59.0 mmol, 8.22 mL, 5.97 g) (dropwise) and stirring continued for 2 hours. The reaction was diluted with dichloromethane and this organic mixture was washed with saturated sodium chloride, water, and saturated sodium chloride. The organic phase was dried with sodium sulfate, filtered and concentrated under vacuum. The residue was purified by silica chromatography (eluting with dichloromethane) to give the title compound (5 g).
MS (ESI) m/z 280.1 [M+H]$^+$ D: 3-((4-(4-(3-Cyclobutylureido)benzoyl)piperazin-1-yl)methyl)-N-(1,1,1-trifluoro-2-methylpropan-2-yl)benzamide To 1-cyclobutyl-3-(4-(piperazine-1-carbonyl)phenyl)urea (0.165 mmol, 50 mg) in tetrahydrofuran (1654 µl) was added 3-(chloromethyl)-N-(1,1,1-trifluoro-2-methylpropan-2-yl)benzamide (0.182 mmol, 50.9 mg) and triethylamine (0.496 mmol, 69.1 µl, 50.2 mg). The reaction was heated to reflux and stirred for 30 minutes then acetonitrile (0.5 mL) and sodium iodide (catalytic amount) were added. After 3 hours stirring, ethyl acetate was added and the organic mixture was washed with water and saturated sodium chloride. The organic phase was dried with sodium sulfate, filtered and concentrated under reduced pressure. This material was lyophilised to give the title compound (81 mg). MS (ESI) m/z 546.5 [M+H]$^+$ Example 45

3-((4-(4-(3-Neopentylureido)benzoyl)piperazin-1-yl)methyl)-N-(1,1,1-trifluoro-2-methylpropan-2-yl)benzamide

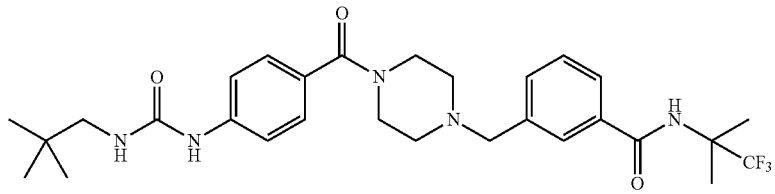

A: tert-Butyl 4-(3-(1,1,1-trifluoro-2-methylpropan-2-ylcarbamoyl)benzyl)piperazine-1-carboxylate 3-(Chloromethyl)-N-(1,1,1-trifluoro-2-methylpropan-2-yl)benzamide (3.10 mmol, 868 mg), tert-butyl piperazine-1-carboxylate (3.10 mmol, 578 mg), sodium iodide (3.10 mmol, 465 mg) and triethylamine (3.10 mmol, 0.433 mL) were all combined in actetonitrile (28 ml) and heated to reflux for 2 hours. After this time the reaction mixture was allowed to cool and ethyl acetate and water were added. The organic layer was separated, dried and concentrated under vacuum to yield the title compound (1.3 g).
MS (ESI) m/z 430.5 [M+H]$^+$ B: 3-(Piperazin-1-ylmethyl)-N-(1,1,1-trifluoro-2-methylpropan-2-yl)benzamide tert-Butyl 4-(3-(1,1,1-trifluoro-2-methylpropan-2-ylcarbamoyl)benzyl)piperazine-1-carboxylate (0.792 mmol, 340 mg) wsa dissolved in dichloromethane (3 mL) and trifluoroacetic acid (7.92 mmol, 0.588 ml, 903 mg) added. After 2 hours stirring, the mixture was taken up in dichloromethane, loaded on to a strong cation exchange column (5 g) and washed with dichloromethane/methanol. Elution of the column with 2M ammonia in methanol gave the title compound (260 mg). MS (ESI) m/z 330.3 [M+H]$^+$ C: 3-((4-(4-Aminobenzoyl)piperazin-1-yl)methyl)-N-(1,1,1-trifluoro-2-methylpropan-2-yl)benzamide To a stirred mixture of 3-(piperazin-1-ylmethyl)-N-(1,1,1-trifluoro-2-methylpropan-2-yl)benzamide (3.07 mmol, 1.01 g), 4-aminobenzoic acid (3.07 mmol, 0.421 g) and triethylamine (6.13 mmol, 0.855 mL, 0.621 g) in dichloromethane (30.7 mL) was added 1-propanephosphonic acid cyclic anhydride (6.13 mmol, 3.63 ml, 3.90 g, 50% solution in ethyl acetate). After 2 hours stirring, dichloromethane was added and the organic mixture was washed with saturated sodium hydrogen carbonate, water, and saturated sodium chloride.

The organic phase was dried with sodium sulfate, filtered and concentrated to yield the title compound (640 mg).
MS (ESI) m/z 449.5 [M+H]+

D: 3-((4-(4-(3-Neopentylureido)benzoyl)piperazin-1-yl)methyl)-N-(1,1,1-trifluoro-2-methylpropan-2-yl)benzamide 3((4-(4-Aminobenzoyl)piperazin-1-yl)methyl)-N-(1,1,1-trifluoro-2-methylpropan-2-yl)benzamide (0.129 mmol, 58 mg) and 4-nitrophenylchloroformate (0.142 mmol, 29 mg) were stirred together in dichloromethane (1 mL) for 16 hours. After this time neopentylamine (0.259 mmol, 32 µL) was added. The volatiles were removed under vacuum and this residue was purified by silica chromatography to yield the title compound (50 mg). MS (ESI) m/z 562.5 [M+H]+

The following compounds were prepared in a similar manner:
45B: 3-((4-(4-(3-Butylureido)benzoyl)piperazin-1-yl)methyl)-N-(1,1,1-trifluoro-2-methylpropan-2-yl)benzamide

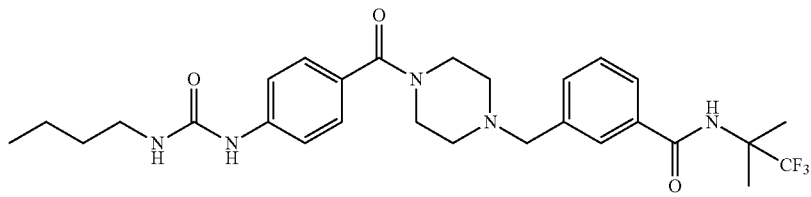

MS (ESI) m/z 548.5 [M+H]+
45C: 3-((4-(4-(34Isobutylureido)benzoyl)piperazin-1-yl)methyl)-N-(1,1,1-trifluoro-2-methylpropan-2-yl)benzamide

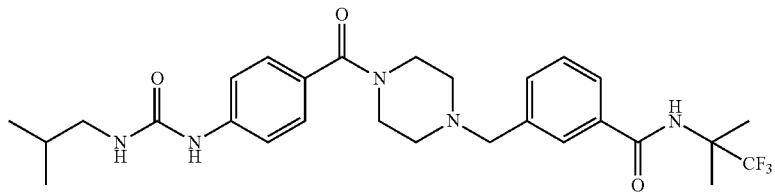

MS (ESI) m/z 548.5 [M+H]+

Example 46

3-((4-(3-Fluoro-4-(3-neopentylureido)benzoyl)piperazin-1-yl)methyl)-N-(1,1,1-trifluoro-2-methylpropan-2-yl)benzamide

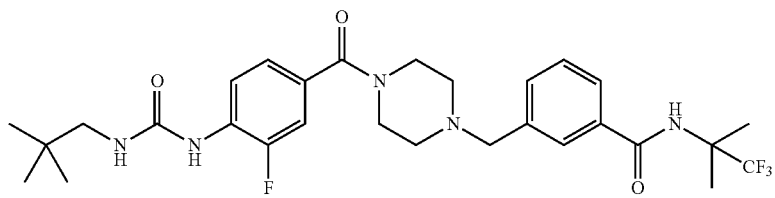

A: 3-((4-(4-Amino-3-fluorobenzoyl)piperazin-1-yl)methyl)-N-(1,1,1-trifluoro-2-methylpropan-2-y)benzamide

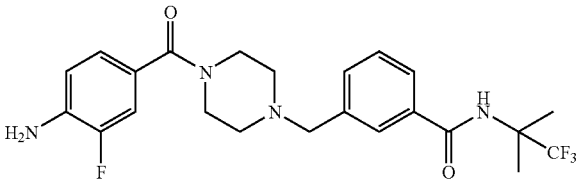

3-(Piperazin-1-ylmethyl)-N-(1,1,1-trifluoro-2-methylpropan-2-yl)benzamide (1.518 mmol, 0.5 g), 4-amino-3-fluorobenzoic acid (1.518 mmol, 0.235 g) and triethylamine (3.80 mmol, 0.529 mL, 0.384 g) were dissolved in dichloromethane (15.18 mL) and stirred for 5 minutes. 1-Propanephosphonic acid cyclic anhydride (3.04 mmol, 1,799 mL, 1.932 g, 50% solution in ethyl acetate) was added dropwise and the reaction mixture was allowed to stir for 1 hour. Dichloromethane was added and the organic mixture was washed with saturated sodium hydrogen carbonate, water, and saturated sodium chloride. The organic phase was dried with sodium sulfate, filtered and concentrated to yield the title compound (500 mg). MS (ESI) m/z 467.4 [M+H]+

B: 3-((4-(3-Fluoro-4-(3-neopentylureido)benzoyl)piperazin-1-yl)methyl)-N-(1,1,1-trifluoro-2-methyl-propan-2-yl)benzamide 3-((4-(4-Amino-3-fluorobenzoyl)piperazin-1-y)methyl)-N-(1,1,1-trifluoro-2-methylpropan-2-yl)benzamide (0.480 mmol, 224 mg) and 4-nitrophenylchloroformate (0.528 mmol, 108 mg) were stirred together in dichloromethane (2 mL) for 16 hours. Neopentylamine (2.4 mol, 300 µL) was added and the volatiles were removed under vacuum. The residue was purified by silica chromatography to yield the title compound (184 mg). MS (ESI) m/z 580.1 [M+H]+

The following compounds were prepared in a similar manner:

46B: 3-((4-(4-(3-(Cyclopropylmethyl)ureido)-3-fluorobenzoyl)piperazin-1-yl)methyl)-N-(1,1,1-trifluoro-2-methyl-propan-2-yl)benzamide hydrochloride

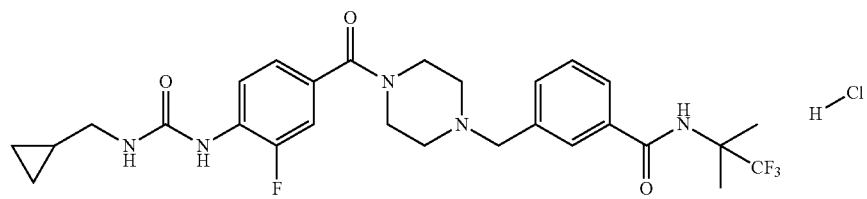

MS (ESI) m/z 564.1 [M+H]+

Example 47

N-Cyclobutyl-3-((4-(3-fluoro-4-(3-neopentylureido)benzoyl)piperazin-1-yl)methyl)benzamide

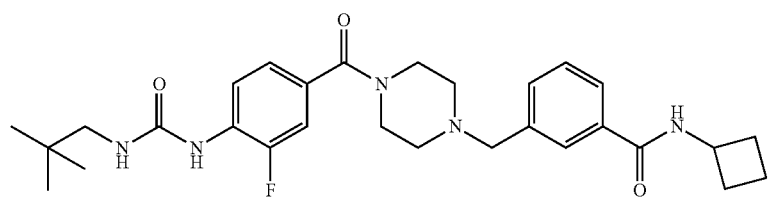

A: tert-Butyl 4-(3-(cyclobutylcarbamoyl)benzyl)piperazine-1-carboxylate

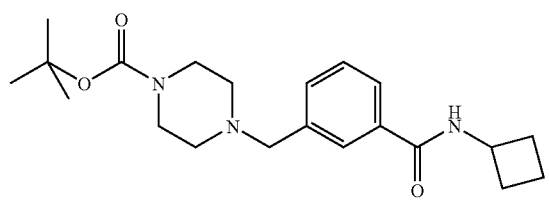

A stirred suspension of tert-butyl piperazine-1-carboxylate (8.94 mmol, 1.665 g), 3-(chloromethyl)-N-cyclobutylbenzamide (8.94 mmol, 2 g), potassium carbonate (17.88 mmol, 2.471 g) and sodium iodide (0.894 mmol, 0.134 g) in acetonitrile (50 ml) was heated at 80° C. for 3 hours. The reaction mixture was diluted with ethyl acetate and water. The organic layer was separated, dried (magnesium sulfate) and concentrated under reduced pressure to give the title compound (3.3 g). MS (ESI) m/z 374.4 ([M+H]+).

B: N-Cyclobutyl-3-(piperazin-1-ylmethyl)benzamide

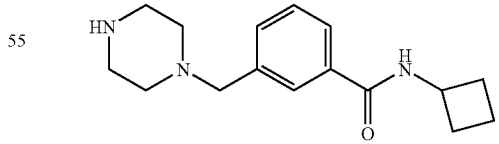

To a stirred solution of tert-butyl 4-(3-(cyclobutylcarbamoyl)benzyl)piperazine-1-carboxylate (8.84 mmol, 3.3 g) in dichloromethane (10 mL) was added trifluoroacetic acid (5 ml). The reaction mixture was stirred for 24 hours then concentrated under reduced pressure. Purification by strong cat-

C: 3-((4-(4-Amino-3-fluorobenzoyl)piperazin-1-yl)methyl)-N-cyclobutylbenzamide

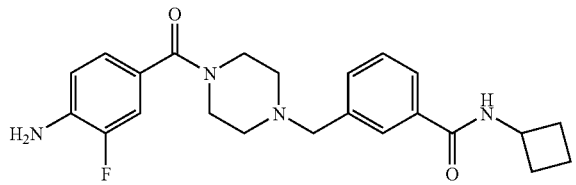

To a solution of N-cyclobutyl-3-(piperazin-1-ylmethyl)benzamide (8.78 mmol, 2.4 g), 4-amino-3-fluorobenzoic acid (8.78 mmol, 1.362 g) and triethylamine (26.3 mmol, 3.67 mL, 2.67 g) in dichloromethane (50 mL) was added 1-propanephosphonic acid cyclic anhydride (13.17 mmol, 7.84 mL, 8.38 g, 50% solution in ethyl acetate). The reaction was stirred for 1 hour then was diluted with ethyl acetate/sodium hydrogen carbonate (aqueous). The organic layer was separated, dried (magnesium sulfate) and concentrated under reduced pressure to give the title compound (2.4 g).

MS (ESI) m/z 411.5 [M+H]$^+$

D: N-Cyclobutyl-3-((4-(3-fluoro-4-(3-neopentylureido)benzoyl)piperazin-1-yl)methyl)benzamide To a stirred solution of bis(trichloromethyl) carbonate (0.331 mmol, 98 mg) in dichloromethane (10 mL) was added a solution of 3-((4-(4-amino-3-fluorobenzoyl)piperazin-1-yl)methyl)-N-cyclobutylbenzamide (0.974 mmol, 400 mg) and N-ethyl-N-isopropylpropan-2-amine (2.144 mmol, 0.354 mL, 277 mg) in dichloromethane (10 mL) (dropwise). The reaction mixture was stirred for 1 hour then 2,2-dimethylpropan-1-amine (1.169 mmol, 0.137 mL, 102 mg) was added. The reaction mixture was stirred for 20 hours. Chromatography on silica (eluting with dichloromethane to dichloromethane/methanol (1% to 3%)) gave the title compound (266 mg).

MS (ESI) m/z 524.7 [M+H]$^+$

Example 48

(R)—N-sec-Butyl-3-((4-(3-fluoro-4-(3-neopentylureido)benzoyl)piperazin-1-yl)methyl)benzamide

A: (R)—N-sec-Butyl-3-(chloromethyl)benzamide

A solution of (R)-butan-2-amine (14.77 mmol, 1.478 mL, 1,081 g) and triethylamine (15.48 mmol, 2.157 mL, 1.566 g) in dichloromethane was added dropwise to a stirred solution of 3-(chloromethyl)benzoyl chloride (14.07 mmol, 2 mL, 2.66 g) in dichloromethane at room temperature. Upon complete addition the reaction was stirred for 2 hours, after which time the solvent was removed under vacuum and ethyl acetate (100 mL) added. The organic solution was then washed with water (200 mL), dried over sodium sulphate and concentrated under vacuum to give the title compound (2.47 g) as a cream solid. MS (ESI) m/z 226.3[M+H]$^+$

B: (R)-tert-Butyl 4-(3-(sec-butylcarbamoyl)benzyl)piperazine-1-carboxylate

A suspension of tert-butyl piperazine-1-carboxylate (5.32 mmol, 0.990 g), (R)—N-sec-butyl-3-(chloromethyl)benzamide (5.32 mmol, 1.2 g), potassium carbonate (10.63 mmol, 1.469 g) and sodium iodide (0.532 mmol, 0.080 g) in acetonitrile (50 mL) were heated at 80° C. for 3 hours. The reaction mixture was diluted with ethyl acetate and water. The organic layer was separated, dried (magnesium sulfate) and concentrated under reduced pressure to give the title compound (2 g). MS (ESI) m/z 376.5 [M+H]$^+$

C: (R)—N-sec-Butyl-3-(piperazin-1-ylmethyl)benzamide

To a stirred solution of (R)-tert-butyl 4-(3-(sec-butylcarbamoyl)benzyl)piperazine-1-carboxylate (5.33 mmol, 2 g) in dichloromethane (10 mL) was added trifluoroacetic acid (5 mL). The reaction mixture was stirred for 24 hours then was concentrated under reduced pressure. Purification by strong cation exchange column chromatography gave the title compound (1.4 g). MS (ESI) m/z 276.3 ([M+H]$^+$).

D: (R)-3-((4-(4-amino-3-fluorobenzoyl)piperazin-1-yl)methyl)-N-sec-butylbenzamide To a solution of (R)—N-sec-butyl-3-(piperazin-1-ylmethyl)benzamide (5.08 mmol, 1.4 g), 4-amino-3-fluorobenzoic acid (5.08 mmol, 0.789 g) and triethylamine (15.25 mmol, 2.126 mL, 1.543 g) in dichloromethane (80 mL) was added 1-propanephosphonic acid cyclic anhydride (7.63 mmol, 2.270 mL, 2.426 g, 50% solution in ethyl acetate). The reaction mixture was stirred for 1 hour then was diluted with ethyl acetate and potassium carbonate (aqueous). The organic layer was separated, dried (magnesium sulfate) and concentrated under reduced pressure. Chromatography on silica (eluting with ethyl acetate to ethyl acetate/methanol (5%)) gave the intermediate (R)-3-((4-(4-amino-3-fluorobenzoyl)piperazin-1-yl)methyl)-N-sec-butylbenzamide (1.2 g).

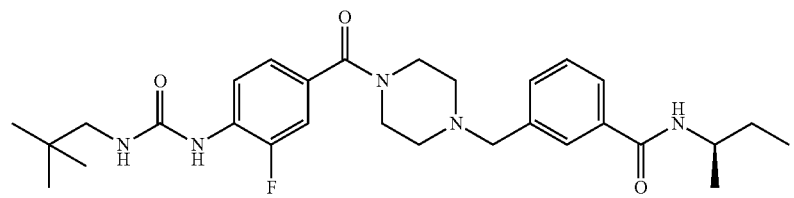

E: (R)—N-sec-Butyl-3-((4-(3-fluoro-4-(3-neopentylureido)benzoyl)piperazin-1-yl)methyl)benzamide To a stirred solution of bis(trichloromethyl) carbonate (0.989 mmol, 0.294 g) in dichloromethane (30 mL) was added (R)-3-((4-(4-amino-3-fluorobenzoyl)piperazin-1-yl)methyl)-N-sec-butylbenzamide (2.91 mmol, 1.2 g) and N-ethyl-N-isopropylpropan-2-amine (6.40 mmol, 1.058 mL, 0.827 g) in dichloromethane (30 mL). The reaction mixture was stirred for 1 hour then 2,2-dimethylpropan-1-amine (3.49 mmol, 0.408 ml, 0.304 g) was added. After 2 hours stirring, the crude material was purified by acidic reverse phase LC/MS then by silica chromatography to give the title compound (25 mg).
MS (ESI) m/z 526.3 [M+H]$^+$ Example 49

3-((4-(4-(3-(Cyclopropylmethyl)ureido)-3-fluorobenzoyl)piperazin-1-yl)methyl)-N-(3,3-difluorocyclobutyl)benzamide

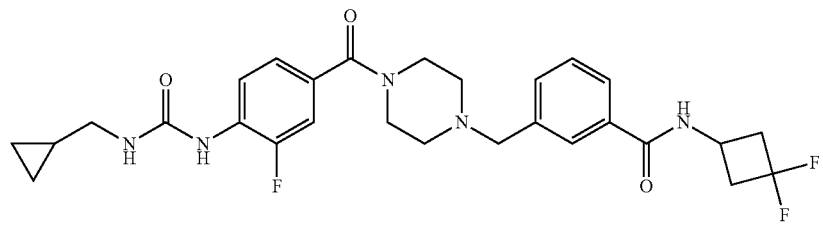

A: 3-(Chloromethyl)-N-(3,3-difluorocyclobutyl)benzamide 3-(Chloromethyl)benzoyl chloride (13.93 mmol, 2.63 g) was stirred in dichloromethane (50 ml) at 0° C. Triethylamine (41.8 mmol, 5.81 ml, 4.23 g) and 3,3-difluorocyclobutanamine hydrochloride (13.93 mmol, 2 g) were combined in dichloromethane and added dropwise. The reaction mixture was allowed to warm to room temperature and stir overnight. The reaction mixture was washed with water, dried over sodium sulfate and concentrated under vacuum to afford the title compound (3.33 g). MS (ESI) m/z 260.3 [M+H]$^+$ B: tert-Butyl 4-(3-(3,3-difluorocyclobutylcarbamoyl)benzyl)piperazine-1-carboxylate

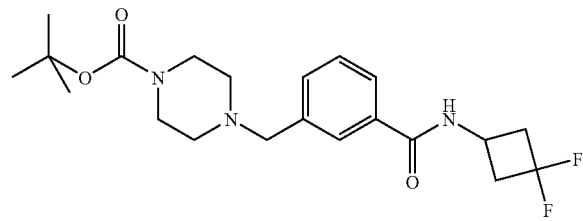

3-(Chloromethyl)-N-(3,3-difluorocyclobutyl)benzamide (12.82 mmol, 3.33 g), tert-butyl piperazine-1-carboxylate (12.82 mmol, 2.388 g), potassium carbonate (38.5 mmol, 5.32 g) and sodium iodide (2.56 mmol, 0.384 g) were combined and heated at reflux in acetonitrile (50 ml) for 2 hours. The solvent was removed under reduced pressure and the residue taken up in dichloromethane, washed with water, dried over sodium sulfate and concentrated under vacuum to afford the title compound (5.179 g).
MS (ESI) m/z 410.3 [M+H]$^+$ C: N-(3,3-Difluorocyclobutyl)-3-(piperazin-1-ylmethyl)benzamide

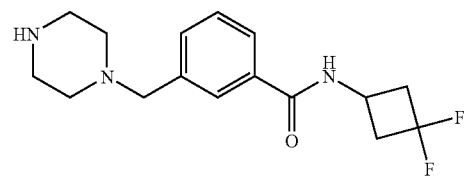

tert-Butyl 4-(3-(3,3-difluorocyclobutylcarbamoyl)benzyl)piperazine-1-carboxylate (12.65 mmol, 5.179 g) was stirred at room temperature in dichloromethane (10 mL)/trifluoroacetic acid (10 mL) for 1 hour with sonication. The solvent was removed under vacuum and the resulting residue was purified by strong cation exchange column chromatography to afford the title compound (3.19 g). MS (ESI) m/z 310.4 [M+H]$^+$ D: 3-((4-(4-Amino-3-fluorobenzoyl)piperazin-1-yl)methyl)-N-(3,3-difluorocyclobutyl)benzamide

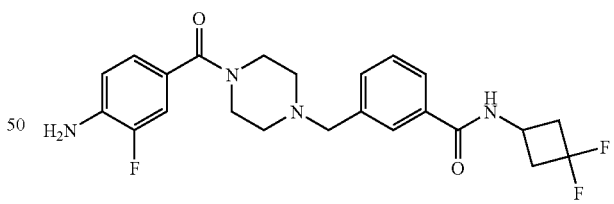

N-(3,3-Difluorocyclobutyl)-3-(piperazin-1-ylmethyl)benzamide (5.14 mmol, 1.59 g), 4-amino-3-fluorobenzoic acid (5.14 mmol, 0.797 g) and triethylamine (15.42 mmol, 2.143 mL, 1.560 g) were stirred in dichloromethane (30 mL) at room temperature. 1-Propanephosphonic acid cyclic anhydride (7.71 mmol, 4.59 mL, 4.91 g, 50% solution in ethyl acetate) was added dropwise and the reaction stirred for 1 hour. The reaction mixture was concentrated under vacuum and the residue taken up in ethyl acetate. The organic phase was washed with saturated sodium hydrogen carbonate solution, dried over sodium sulfate and concentrated under vacuum to afford the title compound (1.255 g). MS (ESI) m/z 447.5 [M+H]$^+$

E: 3-((4-(4-(3-(Cyclopropylmethyl)ureido)-3-fluorobenzoyl)piperazin-1-yl)methyl)-N-(3,3-difluorocyclobutyl)benzamide A mixture of 3-((4-(4-amino-3-fluorobenzoyl)piperazin-1-yl)methyl)-N-(3,3-difluorocyclobutyl)benzamide (0.224 mmol, 0.1 g) and N-ethyl-N-isopropylpropan-2-amine (0.672 mmol, 0.111 mL, 0.087 g) in dichloromethane were added dropwise to a stirred solution of bis(trichloromethyl) carbonate (0.083 mmol, 0.025 g) in dichloromethane (10 mL). The reaction mixture was allowed to stir for 30 minutes at room temperature. Cyclopropylmethylamine (0.448 mmol, 0.039 mL, 0.032 g) was added and the reaction mixture allowed to stir for a further 2 hours. The reaction mixture was washed with water and the organic phase was concentrated under vacuum. The resulting residue was purified by acidic reverse phase HPLC and converted to the free base to afford the title compound (28 mg). MS (ESI) m/z 544.5 [M+H]$^+$

Example 50

N-(1-Cyano-1-cyclopropylethyl)-3-((4-(4-(3-(cyclopropylmethyl)ureido)-3-fluorobenzoyl)piperazin-1-yl)methyl)benzamide

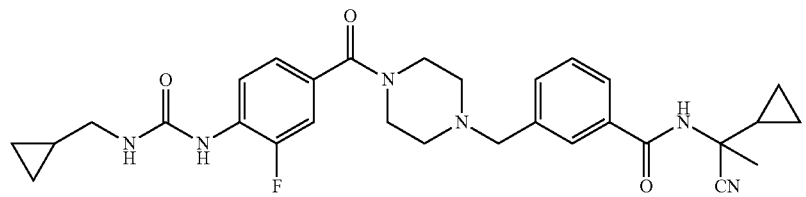

A: 3-(Chloromethyl)-N-(1-cyano-1-cyclopropylethyl)benzamide 3-(Chloromethyl)benzoyl chloride (9.08 mmol, 1.290 ml, 1.716 g) and triethylamine (27.2 mmol, 3.79 mL, 2.76 g) were stirred in dichloromethane (10 mL) at 0° C. 2-Amino-2-cyclopropylpropanenitrile (9.08 mmol, 1 g) was added dropwise and the reaction allowed to warm to room temperature and stir for 1 hour. The reaction mixture was washed with water and the organic phase concentrated under vacuum to afford the title compound (1.451 g). MS (ESI) m/z 263.1 [M+H]$^+$

B: 3-((4-(4-Amino-3-fluorobenzoyl)piperazin-1-yl)methyl)-N-(1-cyano-1-cyclopropylethyl)benzamide

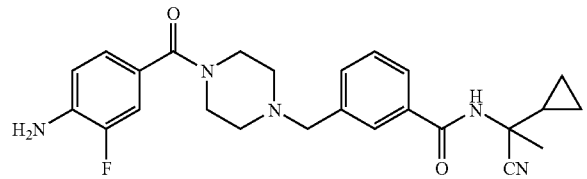

(4-Amino-3-fluorophenyl)(piperazin-1-yl)methanone (2.74 mmol, 0.612 g), 3-(chloromethyl)-N-(1-cyano-1-cyclopropylethyl)benzamide (2.74 mmol, 0.72 g), sodium iodide (0.548 mmol, 0.082 g) and potassium carbonate (8.22 mmol, 1.136 g) were combined in acetonitrile (25 mL) and heated to reflux for 2 hours. The reaction was concentrated under reduced pressure and the resulting residue taken up in dichloromethane and washed with water. The organic phase was dried over sodium sulfate and concentrated under vacuum. The residue was purified by silica column chromatography (eluting with dichloromethane to 4% methanol/dichloromethane) to afford the title compound (195 mg). MS (ESI) m/z 450.3 [M+H]$^+$

C: N-(1-Cyano-1-cyclopropylethyl)-3-((4-(4-(3-(cyclopropylmethyl)ureido)-3-fluorobenzoyl)-piperazin-1-yl)methyl)benzamide 3-((4-(4-Amino-3-fluorobenzoyl)piperazin-1-yl)methyl)—N-(1-cyano-1-cyclopropyl-ethyl)benzamide (49 mg, 0.109 mmol) was stirred In dichloromethane at room temperature. 4-Nitrophenylchloroformate (22 mg, 0.109 mmol) was added and the reaction mixture stirred for 30 minutes. Cyclopropylmethylamine (23 mg, 0.327 mmol) was added and the reaction allowed to stir for 30 minutes at room temperature. The reaction was concentrated under reduced pressure and the resulting residue purified by silica column chromatography to afford the title compound (25 mg). MS (ESI) m/z 547.5 [M+H]$^+$

Example 51

Radioligand Competition Binding Scintillation Proximity Assay

This assay is used to evaluate the potency of compounds in their ability to compete with the binding of the agonist radioligand [$^3$H] T0901317. This assay utilises purified ligand binding domain (LBD) of Liver X Receptor alpha (LXRα) fused to glutathione-S-transferase (GST) tagged protein (LXRα-LBD-GST) and scintillation proximity assay (SpA) technology to determine binding affinities (pKi) of compounds at the ligand binding domain (LBD) of the human nuclear hormone receptor LXRα.

Protocol for expression of human LXRα-LBD-GST:

The ligand binding domain (LBD) of Liver X Receptor alpha (LXRα) was amplified by PCR and sub-cloned into the prokaryotic expression vector pGEX-4T-1 (GE Healthcare). Expression of LXRα from the pGEX-4T-1 plasmid in E. coli resulted in the production of a recombinant glutathione-S-transferase (GST) LXRα-LBD fusion protein. E. coli (containing the plasmid were propagated, induced, and harvested by centrifugation. The bacterial pellet was resuspended in lysis buffer (50 mM tris(hydroxymethyl)-aminomethane (TRIS)-pH 8.0, 100 mM sodium chloride (NaCl), 1 mM ethylene-diaminetetraacetic acid (EDTA), one tablet of proteinase inhibitor cocktail complete/EDTA free (Roche) (per 50 ml of buffer). The mixture was sonicated on ice with a Branson sonifier. The suspension was centrifuged and dithiothreitol (DTT) added to the supernatant to obtain a final concentration of 25 mM. Recombinant human LXRα-LBD- GST protein was purified from the resulting supernatant by affinity chromatography on Glutathione-Sepharose Fast flow (Amersham), and receptor was eluted with buffer containing glutathione (50 mM tris pH 8.0, 2 mM DTT, 10 mM glutathione). Protein was stored in 20 mM N-2-hydroxyethylpiperazine-N'-2-ethanesulfonic Acid (HEPES), 2 mM DTT, 10% glycerol at −80° C.

Binding to LXRαLBD

For each assay, an aliquot of recombinant human LXRα-LBD-GST protein diluted to 0.5 μg/mL was incubated in a final volume of 100 μl SpA buffer (10 mM potassium hydrogen phosphate anhydrous [$K_2HPO_4$], 10 mM potassium phosphate monobasic [$KH_2PO_4$], 2 mM EDTA, 50 mM NaCl, 1 mM DTT, 2 mM 3-[(3-cholamidopropyl)dimethylammonio]-1-propanesulfonate (CHAPS)) containing Protein-A coupled, scintillant filled YtSi SpA beads (GE Healthcare), to a final concentration of 1 mg/ml and Goat anti-GST antibody (GE Healthcare) to a final concentration of 5 μg/ml. T0901317 was used as a reference in this assay with a $K_d$ of 10 nM. To the assay 50 nM [3H] T0901317 (50 Ci/mmol), ± test compound was added and incubated at 15° C. on a plate shaker for 2 hr. After incubation, the assay plates are read on a Packard TopCount. The pKi value for T0901317 in this assay is: pKi 7.8±0.2. T0901317 at a concentration of 1 μM was used as the maximum binding control. Active compounds show pKi values > 5.5 and preferred compounds show pKi values of >7 in this assay.

LXRα Transactivation assay

Intracellular agonist activity was measured in vitro using recombinant Chinese hamster ovary K1 (CHO.K1) cells stably expressing human Estrogen receptor α/Liver X receptor a chimeric receptor protein from a eukaryotic expression construct and a natural estrogen responsive element (ERE)-containing luciferase reporter construct. The ERα/LXRα chimeric receptor protein contains the human LXRα receptor ligand binding domain (LBD) fused to the human ERα receptor DNA binding domain (DBD). In this assay compounds that can bind to the LBD of the human LXRα receptor, are able to activate the ERα/LXRα chimeric receptor protein intracellularly. Following activation, the ERαDBD can induce ERE-mediated luciferase expression via a natural estrogen responsive element present in the rat oxytocin promotor luciferase construct. Using this system a LXR agonist-induced luciferase assay was generated using T0901317 as the agonist control.

Constructs

Expression constructs were prepared by inserting the ligand binding domain (LBD) of human LXRα of human LXRα cDNA adjacent to the human ERα transcription factor DNA binding domain (DBD) to create pNGV1.ERαDBD-LXRαLBD. The pNGV1 mammalian expression construct (EMBL nucleotide sequence database file ASPNGV1, acc. # X99274) carries a selection marker for Neomycin (G418). The ERα responsive rat oxytocin (RO) was used to generate the promoter construct, pROLUC, and contains several copies of the ERα response element (ERE) placed adjacent to the luciferase reporter gene. Construction of the promoter construct was based on the rat oxytocin gene regulatory region (position −363/+16) as a HindII/Mbol restriction enzyme fragment linked to the firefly luciferase encoding sequence. See Ivell and Richter., *Proc Natl Acad Sci USA*. 7:2006-2010 (1984). A stable CHO.K1 cell Sine expressing both pNGV1.ERαDBD-LXRαLBD and pROLUC was generated following transfection and selection of positive expressing clones using Neomycin. The best cell line (CHO.K1 LXRα) was selected on the basis of agonist window in response to 3 μM T0901317 and stability of response up to 20 passages.

Assay of Agonist Activity of Test Compounds in Lxrα Trans-activation Assay.

CHO.K1 LXRα cells were seeded at a density of 25000 cells/well in 96 well plates in 200 μl of Dulbecco's Modified Eagle Medium (phenol red free) containing 5% charcoal treated bovine calf serum at 37° C. in a humidified atmosphere of 5% $CO_2$. After 6 h, compounds were characterised by incubation with cells for 16 h across a concentration range. T0901317 at a concentration of 3 μM was used as the maximum agonist control. Luciferase activity was determined using a Luciferase assay kit (Perkin Elmer) by addition of lysis buffer to each well and light emission measured using a Packard Topcount reader. The $pEC_{50}$ value for T0901317 in this assay is: $pEC_{50}=7.0\pm0.3$. Agonist activities of test compounds were compared against the maximum agonist control. Preferred compounds of the invention were shown to have LXRα agonist activity using this assay protocol.

The invention claimed is:

1. A N-benzyl,N'-arylcarbonylpiperazine derivative having the general formula I

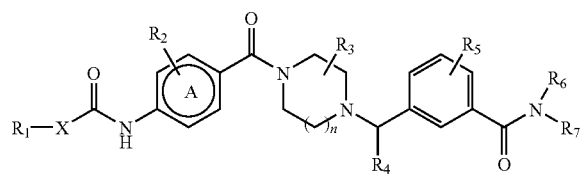

Formula I wherein n is 1 or 2;

A is a 6-membered aromatic ring optionally containing 1 or 2 nitrogen atoms;

X is $NR_8$, O or a bond;

$R_1$ is H, $(C_{1-8})$alkyl optionally substituted with halogen, $(C_{1-4})$alkyloxy, $(C_{1-4})$alkyloxycarbonyl, $(C_{3-8})$cycloalkyl, OH, $CF_3$, cyano or $NR_9R_{10}$, $(C_{2-6})$alkenyl, $(C_{2-6})$alkynyl, $(C_{3-8})$-cycloalkyl, phenyl optionally substituted with $(C_{1-4})$alkyl, $(C_{1-4})$alkyloxy, halogen, CN, $CF_3$, $OCF_3$ or $NO_2$, a 5- or 6-membered saturated heterocyclic group containing 1 or 2 heteroatoms selected from O and S, or a 5- or 6-membered heteroaryl group containing 1-3 heteroatoms selected from O, S and N optionally substituted with $(C_{1-4})$alkyl, $(C_{1-4})$-alkyloxy, halogen or $CF_3$; or $R_1$ is $(C_{1-3})$alkyl substituted with phenyl optionally substituted with $(C_{1-4})$alkyl, $(C_{1-4})$-alkyloxy, halogen or with 2 substituents at adjacent positions forming O—($CH_2$)n-O, wherein n is 1 or 2, a 5- or 6-membered heteroaryl group containing 1-3 heteroatoms selected from O, S and N optionally substituted with $(C_{1-3})$alkyl, $(C_{1-3})$ alkyloxy or halogen, or a 5- or 6-membered saturated heterocyclic group containing 1 or 2 heteroatoms selected from O, S and N optionally substituted with $(C_{1-4})$alkyl, $(C_{1-4})$-alkyloxy, oxo, OH or halogen; or when X is $NR_8$, $R_1$ may together with $R_8$ and the N to which they are bonded form a 4-8 membered ring optionally containing a further heteroatom selected from O and S and which ring is optionally substituted with OH, $(C_{1-4})$alkyl, $(C_{1-4})$alkyloxy or halogen;

$R_2$ optionally represents 1-3 substituents independently selected from $(C_{1-4})$alkyl, $(C_{1-4})$-alkyloxy, $CF_3$ and halogen;

R₃ optionally represents 1-4 substituents independently selected from $(C_{1-4})$alkyl and $(C_{1-4})$alkyl substituted by OH or 1 or more halogens;

R₄ is H or $(C_{1-6})$alkyl;

R₅ optionally represents 1-3 substituents independently selected from $(C_{1-3})$alkyl, $(C_{1-3})$alkyloxy and halogen;

R₆ is H, $(C_{1-6})$alkyl optionally substituted with halogen, CF₃ or CN, $(C_{3-6})$cycloalkyl optionally containing a heteroatom selected from O and S, and optionally substituted by CN or phenyl, $(C_{3-6})$cycloalkyl$(C_{1-4})$alkyl, or a 5- or 6-membered (hetero)aryl group, optionally linked through a methylene group, and optionally substituted with $(C_{1-4})$alkyl, $(C_{1-4})$alkyloxy, $(C_{1-4})$alkylsulfonyl, halogen, CN, CF₃, CF₃O or NO₂;

R₇ is H or $(C_{1-3})$alkyl;

R₈, when present, is H or $(C_{1-3})$alkyl; or

R₈ together with R₁, and the N to which they are bonded form a 4-8 membered ring optionally containing a further heteroatom selected from O and S and which ring is optionally substituted with OH, $(C_{1-3})$alkyl, $(C_{1-3})$alkyloxy or halogen;

R₉ and R₁₀ are independently selected from H, $(C_{1-3})$alkyl or $(C_{1-3})$alkylcarbonyl; or R₉ and R₁₀ together with the N to which they are bonded form a 4-8 membered ring optionally containing a further heteroatom selected from O and S;

or a pharmaceutically acceptable salt thereof.

2. The N-benzyl,N'-arylcarbonylpiperazine derivative of claim 1, wherein X is NH and n is 1.

3. The N-benzyl,N'-arylcarbonylpiperazine derivative of claim 2, wherein A is phenyl.

4. The N-benzyl,N'-arylcarbonylpiperazine derivative of claim 3, wherein R₁ is $(C_{1-8})$alkyl optionally substituted with $(C_{3-8})$cycloalkyl, $(C_{2-6})$alkenyl, $(C_{3-8})$cycloalkyl or phenyl optionally substituted with halogen.

5. The N-benzyl,N'-arylcarbonylpiperazine derivative of claim 4, wherein R₃ is absent or represents methyl, and wherein R₅ is absent or represents halogen.

6. The N-benzyl,N'-arylcarbonylpiperazine derivative of claim 5, wherein R₆ is $(C_{1-6})$alkyl optionally substituted with CF₃, and R₇ is H.

7. The N-benzyl,N'-arylcarbonylpiperazine derivative of claim 1 which is selected from the group consisting of N-tert-butyl-3-((4-(4-(3-(cyclopropylmethyl)ureido)benzoyl)piperazin-1-yl)methyl)benzamide;

N-tert-butyl-3-((4-(4-(3-neopentylureido)benzoyl)piperazin-1-yl)methyl)benzamide;

N-tert-butyl-3-((4(3-fluoro-4-(3-neopentylureido)benzoyl)piperazin-1-yl)methyl)benzamide;

N-tert-butyl-3-((4-(3-fluoro-4-(3-cyclobutylureido)benzoyl)piperazin-1-yl)methyl)benzamide;

N-tert-butyl-3-((4-(4-(3-(cyclopropylmethyl)ureido)-3-fluorobenzoyl)piperazin-1-yl)methyl)benzamide;

N-tert-butyl-3-((4-(3-fluoro-4-(3-isobutylureido)benzoyl) piperazin-1-yl)methyl)benzamide;

N-tert-butyl-3-((4-(3-fluoro-4-(3-isopentylureido)benzoyl)piperazin-1-yl)methyl)benzamide;

N-tert-butyl-3-((4-(4-(3-(cyclobutylmethyl)ureido)-3-fluorobenzoyl)piperazin-1-yl)methyl)benzamide;

N-tert-butyl-3-((4-(4-(3-butylureido)-3-fluorobenzoyl)piperazin-1-yl)methyl)benzamide N-tert-butyl-3-((4-(4-(3-(2-cycopropylethyl)ureido)-3-fuorobenzoyl)piperazin-1-yl)methyl)benzamide;

3-((4-(4-(3-neopentylureido)benzoyl)piperazin-1-yl)methyl)-N-(1,1,1-trifluoro-2-methylpropan-2-yl)benzamide;

3-((4-(4-(3-butylureido)benzoyl)piperazin-1-yl)methyl)-N-(1,1,1-trifluoro-2-methylpropan-2-yl)benzamide;

3-((4-(4-(3-isobutylureido)benzoyl)piperazin-1-yl)methyl)-N-(1,1,1-trifluoro-2-methylpropan-2-yl)benzamide;

3-((4-(3-fluoro-4-(3-neopentylureido)benzoyl)piperazin-1 yl)methyl)-N-(1,1,1-trifluoro-2-methylpropan-2-yl)benzamide;

3-((4-(4-(3-(cyclopropylmethyl)ureido)-3-fluorobenzoyl)piperazin-1-yl)methyl)-N-(1,1,1-trifluoro-2-methylpropan-2-yl)benzamide;

N-tert-butyl-3-((4-(3-chloro-4-(3-cyclobutylureido)benzoyl)piperazin-1-yl)methyl)-benzamide;

N-tert-butyl-3-((4-(3-chloro-4-(3-(cyclopropylmethyl)ureido)benzoyl)piperazin-1-yl)methyl)benzamide;

N-tert-butyl-3-((4-(3-chloro-4-(3-neopentylureido)benzoyl)piperazin-1-yl)methyl)benzamide;

N-tert-butyl-3-((4-(3-chloro-4-(3-isobutylureido)benzoyl)piperazin-1-yl)methyl)benzamide;

N-tert-butyl-3-((4-(4-(3-butylureido)-3-chlorobenzoyl)piperazin-1-yl)methyl)benzamide;

N-tert-butyl-3-((4-(3-chloro-4-(3-isopentylureido)benzoyl)piperazin-1-yl)methyl)benzamide;

N-tert-butyl-3-((4-(2,3-difluoro-4-(3-neopentylureido)benzoyl)piperazin-1-yl)methyl)benzamide;

N-tert-butyl-3-((4-(2,3-difluoro-4-(3-isopentylureido)benzoyl)piperazin-1-yl)methyl)benzamide;

N-tert-butyl-3-((4-(4-(3-butylureido)-2,3-difluorobenzoyl)piperazin-1-yl)methyl)benzamide;

N-tert-butyl-3-((4-(2,3-difluoro-4-(3-isobutylureido)benzoyl)piperazin-1-yl) methyl)benzamide;

N-tert-butyl-3-((4-(4-(3-(cyclopropylmethyl)ureido)-2,3-difluorobenzoyl)piperazin-1-yl)methyl)benzamide;

N-tert-butyl-3-((4-(4-(3-cyclobutylureido)-2,3-difluorobenzoyl)piperazin-1-yl)methyl)benzamide;

N-tert-butyl-3-((4-(3-chloro-4-(3-(cyclopropylmethyl)ureido)-2-fluorobenzoyl)piperazin-1-yl)methyl)benzamide;

N-tert-butyl-3-((4-(3-chloro-2-fluoro-4-(3-isobutylureido)benzoyl)piperazin-1-yl)methyl)benzamide;

N-tert-butyl-3-((4-(4-(3-cyclobutylureido)benzoyl)piperazin-1-yl)methyl)-2-fluorobenzamide;

N-tert-butyl-2-fluoro-3-((4-(4-(3-neopentylureido)benzoyl)piperazin-1-yl)methyl)benzamide;

N-cyclobutyl-3-((4-(3-fluoro-4-(3-neopentylureido)benzoyl)piperazin-1-yl)methyl)benzamide; and (R)—N-sec-butyl-3-((4-(3-fluoro-4-(3-neopentylureido) benzoyl)piperazin-1-yl)methyl)benzamide; or a pharmaceutically acceptable salt thereof.

8. A pharmaceutical composition comprising a N-benzyl, N'-arylcarbonylpiperazine derivative of claim 1 and or a pharmaceutically acceptable salt thereof, and pharmaceutically acceptable auxiliaries.

9. The pharmaceutical composition of claim 8, wherein the N-benzyl,N'-arylcarbonylpiperazine derivative is selected from the group consisting of N-tert-butyl-3-((4-(4-(3-(cyclopropylmethyl)ureido)benzoyl)piperazin-1-yl)methyl)benzamide;

N-tert-butyl-3-((4-(4-(3-neopentylureido)benzoyl)piperazin-1-yl)methyl)benzamide;

N-tert-butyl-3-((4-(3-fluoro-4-(3-neopentylureido)benzoyl)piperazin-1-yl)methyl)benzamide;

N-tert-butyl-3-((4-(3-fluoro-4-(3-cyclobutylureido)benzoyl)piperazin-1-yl)methyl)benzamide;

N-tert-butyl-3-((4-(4-(3-(cyclopropylmethyl)ureido)-3-fluorobenzoyl)piperazin-1-yl)methyl)benzamide;

N-tert-butyl-3-((4-(3-fluoro-4-(3-isobutylureido)benzoyl)piperazin-1-yl)methyl)benzamide;
N-tert-butyl-3-((4-(3-fluoro-4-(3-isopentylureido)benzoyl)piperazin-1-yl)methyl)benzamide;
N-tert-butyl-3-((4-(4-(3-(cyclobutylmethyl)ureido)-3-fluorobenzoyl)piperazin-1-yl)methyl)benzamide;
N-tert-butyl-3-((4-(4-(3-butylureido)-3-fluorobenzoyl)piperazin-1-yl)methyl)benzamide;
N-tert-butyl-3-((4-(4-(3-(2-cyclopropylethyl)ureido)-3-fluorobenzoyl)piperazin-1-yl)methyl)benzamide;
-3-((4-(4-(3-neopentylureido)benzoyl)piperazin-1-yl)methyl)-N-(1,1,1-trifluoro-2-methylpropan-2-yl)benzamide;
3-((4-(4-(3-butylureido)benzoyl)piperazin-1-yl)methyl)-N-(1,1,1-trifluoro-2-methylpropan-2-yl)benzamide;
-3-((4-(4-(3-isobutylureido)benzoyl)piperazin-1-yl)methyl)—N-(1,1,1-trifluoro-2-methylpropan-2-yl)benzamide;
-3-((4-(3-fluoro-4-(3-neopentylureido)benzoyl)piperazin-1-yl)methyl)-N-(1,1,1-trifluoro-2-methylpropan-2-yl)benzamide;
-3-((4-(4-(3-(cyclopropylmethyl)ureido)-3-fluorobenzoyl)piperazin-1-yl)methyl)-N-(1,1,1-trifluoro-2-methylpropan-2-y)benzamide hydrochloride;
N-tert-butyl-3-((4-(3-chloro-4-(3-cyclobutylureido)benzoyl)piperazin-1-yl)methyl)benzamide;
N-tert-butyl-3-((4-(3-chloro-4-(3-(cyclopropylmethyl)ureido)benzoyl)piperazin-1-yl)methyl)benzamide;
N-tert-butyl-3-((4-(3-chloro-4-(3-neopentylureido)benzoyl)piperazin-1-yl)methyl)benzamide;
N-tert-butyl-3-((4-(3-chloro-4-(3-isobutylureido)benzoyl)piperazin-1-yl)methyl)benzamide;
N-tert-butyl-3-((4-(4-(3-butylureido)-3-chlorobenzoyl)piperazin-1-yl)methyl)benzamide;
N-tert-butyl-3-((4-(3-chloro-4-(3-isopentylureido)benzoyl)piperazin-1-yl)methyl)benzamide;
N-tert-butyl-3-((4-(2,3-difluoro-4-(3-neopentylureido)benzoyl)piperazin-1-yl)methyl)benzamide;
N-tert-butyl-3-((4-(2,3-difluoro-4-(3-isopentylureido)benzoyl)piperazin-1-yl)methyl)benzamide;
N-tert-butyl-3-((4-(4-(3-butylureido)-2,3-difluorobenzoyl)piperazin-1-yl)methyl)benzamide;
N-tert-butyl-3-((4-(2,3-difluoro-4-(3-isobutylureido)benzoyl)piperazin-1-yl)methyl)benzamide;
N-tert-butyl-3-((4-(4-(3-(cyclopropylmethyl)ureido)-2,3-difluorobenzoyl)piperazin-1-yl)methyl)benzamide;
N-tert-butyl-3-((4-(4-(3-cyclobutylureido)-2,3-difluorobenzoyl)piperazin-1-yl)methyl)benzamide;
N-tert-butyl-3-((4-(3-chloro-4-(3-(cyclopropylmethyl)ureido)-2-fluorobenzoyl)piperazin-1-y)methyl)benzamide;
N-tert-butyl-3-((4-(3-chloro-2-fluoro-4-(3-isobutylureido)benzoyl)piperazin-1-yl)methyl)benzamide;
N-tert-butyl-3-((4-(4-(3-cyclobutylureido)benzoyl)piperazin-1-yl)methyl)-2-fluorobenzamide;
N-tert-butyl-2-fluoro-3-((4-(4-(3-neopentylureido)benzoyl)piperazin-1-yl)methyl)benzamide;
N-cyclobutyl-3-((4-(3-fluoro-4-(3-neopentylureido)benzoyl)piperazin-1-yl)methyl)benzamide; and
(R)—N-sec-butyl-3-((4-(3-fluoro-4-(3-neopentylureido)benzoyl)piperazin-1-yl)methyl)benzamide; or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,314,091 B2 | Page 1 of 1 |
| APPLICATION NO. | : 12/194146 | |
| DATED | : November 20, 2012 | |
| INVENTOR(S) | : Ho et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 320 days.

Signed and Sealed this
Seventh Day of May, 2013

Teresa Stanek Rea
*Acting Director of the United States Patent and Trademark Office*